(12) United States Patent
Matsuda et al.

(10) Patent No.: US 6,946,283 B2
(45) Date of Patent: *Sep. 20, 2005

(54) GINKGO BILOBA LEVOPIMARADIENE SYNTHASE

(75) Inventors: Seiichi P. T. Matsuda, Houston, TX (US); Hala G. Schepmann, Talent, OR (US)

(73) Assignee: William Marsh Rice University, Houston, TX (US)

(*) Notice: Subject to any disclaimer, the term of this patent is extended or adjusted under 35 U.S.C. 154(b) by 391 days.

This patent is subject to a terminal disclaimer.

(21) Appl. No.: 10/041,007

(22) Filed: Jan. 7, 2002

(65) Prior Publication Data

US 2002/0164736 A1 Nov. 7, 2002

Related U.S. Application Data

(60) Provisional application No. 60/259,881, filed on Jan. 5, 2001.

(51) Int. Cl.[7] .......................... C12N 15/60; C12N 1/15; C12N 5/10
(52) U.S. Cl. ............... 435/252.3; 435/419; 435/252.33; 435/320.1; 435/254.21; 435/254.22; 435/254.2; 435/233; 435/193; 536/23.2
(58) Field of Search ............................. 435/320.1, 419, 435/252.3, 252.33, 254.21, 254.22, 254.11, 254.2, 233, 193; 536/23.2

(56) References Cited

U.S. PATENT DOCUMENTS

| 4,849,410 A | 7/1989 | Jacobs et al. ................. 514/33 |
| 5,151,352 A | 9/1992 | Nakano et al. ............. 435/123 |
| 5,189,187 A | 2/1993 | Nakano et al. ............. 549/548 |
| 5,241,084 A | 8/1993 | Teng |
| 5,322,688 A | 6/1994 | Schwabe |
| 5,389,370 A | 2/1995 | O'Reilly et al. |
| 5,399,348 A | 3/1995 | Schwabe |
| 5,429,939 A | 7/1995 | Misawa et al. ................ 435/67 |
| 5,473,057 A | 12/1995 | Fenical et al. ............. 536/17.3 |
| 5,512,286 A | 4/1996 | Schwabe |
| 5,589,581 A | 12/1996 | Misawa et al. ............ 536/23.2 |
| 5,599,950 A | 2/1997 | Teng |
| 5,602,184 A | 2/1997 | Myers et al. ................ 514/739 |
| 5,637,302 A | 6/1997 | Bombardelli et al. |
| 5,637,484 A | 6/1997 | Yukimune et al. .......... 435/123 |
| 5,968,789 A | 10/1999 | Yukimune et al. .......... 435/123 |
| 6,235,287 B1 | 5/2001 | Weidner et al. .......... 424/195.1 |

OTHER PUBLICATIONS

Broun, Pierre et al., *Catalytic Plasticity of Fatty Acid Modification Enzymes Underlying Chemical Diversity of Plant Lipids*, Science Magazine 282, pp 1315–1317, Nov. 13, 1998.

Richman, Alex et al., *Diterpene synthesis in Stevia rebaudiana: recruitment and up-regulation of key enzymes from the gibberellin biosynthetic pathway*, The Plant Journal 19(4), pp 411–421, 1999.

Seffernick, Jennifer et al., *Melamine Deaminase and Atrazine Chlorohydrolase: 98 Percent Identical but Functionally Different*, Journal of Bacteriology, vol. 183, No. 8, pp. 2405–2410, Apr. 2001.

(Continued)

Primary Examiner—Rebecca E. Prouty
(74) Attorney, Agent, or Firm—Baker Botts L.L.P.

(57) ABSTRACT

The present invention is directed to nucleic acid sequences of *Ginkgo biloba* diterpene synthases, particularly of a levopimaradiene synthase. More specifically, the invention is directed to a cell of a unicellular organism, such as *Saccharomyces cerevisiae* or *Escherichia coli*, comprising levopimaradiene synthase for the metabolically engineered in vivo biosynthesis of a diterpene and a ginkgolide.

21 Claims, 4 Drawing Sheets

OTHER PUBLICATIONS

Witkowski, Andrzej et al., *Conversion of a β–Ketoacyl Synthase to a Malonyl Decarboxylase by Replacement of the Active–Site Cysteine with Glutamine*, Biochemistry 1999, vol. 38, pp 11643–11650, 1999.

Sousa, Silvino et al., *The AR04 gene of Candida albicans encodes a tyrosine–sensitive DAHP synthase: evolution, functional conservation and phenotype of Aro3p–, Aro4p–deficient mutants*, Microbiology vol. 148, pp 1291–1303, 2002.

Balz, J.P., et al. (1999) Production of ginkgolides and bilobalide by *Ginkgo biloba* plants and tissue cultures. Planta Medica 65(7): 620–626.

Bohlmann, J. et al. (1998) Proc. Natl. Acad. Sci. USA 95, 4126–4133.

Cartayrade, A., et al. (1997) Plant Physiol. Biochem. 35, 859–868.

Corey, E. J., et al. (1987) J. Am. Chem. Soc. 109, 7534–7536.

Corey, E. J., et al. (1988) J. Am. Chem. Soc. 110, 649–651.

Corey, E. J., et al. (1988) Tetrahedron Lett. 29, 3205–3206.

Le Bars, Pl. L. et al. (1997) A placebo–controlled, double–blind, randomized trial of an extract of *Ginkgo biloba* for dementia. North American EGb Study Group. J. Amer. Med. Assoc. 278(16):1327–32.

Neau, E., et al. (1997) Plant Physiol. Biochem. 35, 869–879.

Schwarz, M., et al. (1999) Comp. Nat. Prod. Chem. 2, 367–400.

Albrecht, M., et al., *Synthesis of atypical cyclic and acyclic hydroxy carotenoids in Escherichia coli transformants*, Journal of Biotechnology 58 (1997) 177–185, Sep. 22, 1997.

Bailey, James E., *Toward a Science of Metabolic Engineering*, Science, New Series, vol. 252, Issue 5013, 1668–1675, Jun. 21, 1991.

Basson, Michael E., et al., *Identifying Mutations in Duplicated Functions in Saccharomyces cerevisiae: Recessive Mutations in HMG–CoA Reductase Genes*, Genetics, 117:645–655, Dec. 1987.

Basson, Michael E, *Saccharomyces cerevisiae contains two functional genes encoding 3–hydroxy–3–methylglutaryl–coenzyme A reductase*, Proc. Natl. Acad. Sci. USA 83: 5563–57, 1986.

Corey, E.J., et al., *Isolation of an Arabidopsis thaliana gene encoding cycloartenol synthase by functional expression in a yeast mutant lacking lanosterol synthase by the use of a chromatographic screen*, Proc. Natl. Acad. Sci USA vol. 90, pp. 11628–11632, Dec. 1993.

Crowley, James H., et al., *A Mutation in a Purported Regulatory Gene Affects Control of Sterol Uptake in Saccharomyces cerevisiae*, Journal of Bacteriology, vol. 180, No. 16, p. 4177–4183, Aug. 1998.

Funk, Christoph, et al., *Diterpenoid Resin Acis Biosynthesis in Conifers: Characterization of Two Cytochrome P450–Dependent Monooxygenases and an Aldehyde Dehydrogenase Involved in Abietic Acid Biosynthesis*, Archives of Biochemistry and Biophysics, vol. 308, No. 1, pp. 258–266, Jan. 1994.

Hara, Mitsunobu, et al., *Leinamycin, A New Antitumor Antibiotic From Streptomyces, Producing Organism, Fermentation and Isolation*, The Journal of Antibiotics vol. XLII pp. 1768–1774, Dec. 1989.

Hezari, Mehri, et al., *Purification and Characterization of Taxa–4(5), 11(12)–diene Synthase from Pacific Yew (Taxus brevifolia) that Catalyzes the First Committed Strep of Taxol Biosynthesis*, Archives of Biochemistry and Biophisics, vol. 322, No. 2, pp. 437–444, Oct. 1, 1995.

Jiang, Yu, et al., *BTS1 Encodes a Geranylgeranyl Diphosphate Synthase in Saccharomyces cerevisiae*, The Journal of Biological Chemistry, vol. 270, No. 37, pp. 21793–21799, Sep. 15, 1995.

Kajiwara, Susumu, et al., *Expression of an exogenous isopentenyl diphosphate isomerase gene enhances isoprenoid biosynthesis in Escherichia coli*, Biochem J., 324(Pt 2): 421–6, Jun. 1, 1997.

Kholodenko, Boris N., et al., *Metabolic Design: How to Engineer a Living Cell to Desired Metabolite Concentrations and Fluxes*, Biotechnol Bioeng, 59(2):239–247, Jul. 20, 1998.

LaFever, Roy E., et al., *Diterpenoid Resin Acis Biosynthesis in Conifers: Enzymatic Cyclization of Geranylgeranyl Pyrophosphate to Abietadiene, the Precursor of Abietic Acid*, Archives of Biochemistry and Biophysics, vol. 313. No. 1, pp. 139–149, Aug. 15, 1994.

Leak, Frank W., et al., *In Yeast, upc2—1 Confers a Decrease in Tolerance to LiCl and NaCl, Which Can Be Suppressed by the P–Type ATPase Encoded by ENA2*, DNA and Cell Biology, vol. 18, No. 2, 1999 pp. 133–139, 1999.

Learned, R. Marc, et al., *3–Hydroxy–3–methylglutaryl–coenzyme A reductase from Arabidopsis thaliana is structurally distinct from the yeast and anmal enzymes*, Proc. Natl. Acad. Sci. USA vol. 86, pp. 2779–2783, Apr. 1989.

Lewis, T.L., et al., *Pleiotropic Mutations in Saccharomyces cerevisiae Affecting Sterol Uptake and Metabolism*, Yeast 4(2):93–106, 1988.

Liu, Shuang–Jiang, et al., *A Novel Genetically Engineered Pathway for Synthesis of Poly (Hydroxyalkanoic Acids) in Escherichia coli*, Applied and Environmental Microbiology, vol. 66, No. 2, p. 739–743, Feb. 2000.

Misawa, Norihiko, et al., *Production of B–Caroltene in Zymomonas mobilis and Agrobacterium tumefaciens by Introduction of the Biosynthesis Genes from Erwinia uredovora*, Applied and Environmental Microbiology, vol. 57, No. 6, p. 1847–1849, Jun. 1991.

Misawa, Norihiko, et al., *Metabolic engineering for the production of carotenoids in non–carotenogenci bacteria and yeasts*, Journal of Biotechnology 59 (1998) 169–181.

Misawa, Norihiko, et al., *Expression of a Tomato cDNA Coding for Phytoene Synthase in Escherichia coli, Phytoene Formation In Vivo and In Vitro, and Functional Analysis of the Various Truncated Gene Products*, J. Biochem. 116, 980–985 (1994).

Miura, Yutaka, et al., *Production of Lycopene by the Food Yeast, Candida utilis That Does Not Naturally Synthesize Cartenoid*, Biotechnol Bioeng., 58(2–3): 306–8, Apr. 20, 1998.

Miura, Yutaka, et al., *Production of the Carotenoids Lycopene, B–Caroltene, and Astazanthin in the Food Yeast Candida utilis*, Applied and Environmental Microbiology, vol. 64, No. 4, p. 1226–1229, Apr. 1998.

Ness, Frederique, et al., *SUT1 is a putative Zn[II]2 Cys6–transcription factor whose upregulation enhances both sterol uptake and synthesis in aerobically growing Saccharomyces cerevisiae cells*, Eur. J. Biochem. 268, 1585–1595, Feb. 2001.

Parks, Leo W., et al., *Physiological Implications of Sterol Biosynthesis in Yeast*, Annu. Rev. Microbiol. 49:95–116, 1995.

Parks, Leo W., et al., *Biochemical and Physiological Effects of Sterol Alternations in Yeast–A Review*, Lipids vol. 30 No. 3:227–230, 1995.

Peters, Reuben J., et al., *Abietadiene Synthase from Grand Fir (Abies grandis) Characterization and Mechanism of Action of the "Pseudomature" Recombinant Enzyme*, Biochemistry 39: 15592–15602, Dec. 2000.

Polakowski, T., et al., *Overexpression of a cytoolic hydroxymethylglutaryl–CoA reductase leads to squalene accumulation in yeast*, Appl Microbiol Biotechnol. 49:66–71, 1998.

Ravn, Matthew M., et al., Stereochemistry of the Cyclization–Rearrangement of (+)–Copalyl Diphosphate to (−)–Abietadiene Catalyzed by Recombinant Abietadiene Synthase from *Abies grandis*, Org. Letters Vo. 2, No. 5, p. 573–576, Mar. 2000.

Shimada, Hiroshi, et al., *Increased Carotenoid Production by the Food Yeast Candida utilis through Metabolic Engineering of the Isoprenoid Pathway*, App. and Environ. Microbiology, vol. 64, No. 7, p. 2676–2680, Jul. 1998.

Stephanopoulos, G., *Bioinformatics and Metabolic Engineering*, Metabolic Engineering 2(3): 157–158, 2000.

Stofer Vogel, Brigitte, et al., *Abietadiene Synthase from Grand Fir (Abies grandis) cDNA Isolation, Characterization and Bacterial Expression of a Bifunctional Diterpene Cyclase Involved in Resin Acid Biosynthesis*, J Biological Chemistry, vol. 271, No. 38: 23262–23268, Sep. 20, 1996.

Trapp, Susan C., et al., *Genomic Organization of Plant Terpene Synthases and Molecular Evolutionary Implications*, Genetics, 158(2):811–832, Jun. 2001.

Wang, Chia–Wei, et al., *Engineered Isoprenoid Pathway Enhances Astaxanthin Production in Escherichia coli*, Biotech and Bioeng, vol. 62, No. 2, 235–241, Jan. 20, 1999.

Wildung, Mark R., et al., *A cDNA Clone for Taxadiene Synthase, the Diterpene Cyclase That Catalyzes the Committed Step of Taxol Biosynthesis*, J. of Biological Chem., Vo. 271, No. 16: 9201–9204, Apr. 19, 1996.

Yamano, Shigeyuki, et al., *Metabolic Engineering for Production of B–Carotene and Lycopene in Saccharomyces cerevisiae*, Biosci. Biotech. Biochem., 58(6): 1112–1114, 1994.

(watch out for losing text in table)

Ginkgolides A, B, C, J, M

| Ginkgolide | | | |
|---|---|---|---|
| Ginkgolide A | | | |
| Ginkgolide B | | | |
| Ginkgolide C | | | |
| Ginkgolide J | | | |
| Ginkgolide M | | | |

FIG. 4

GINKGO BILOBA LEVOPIMARADIENE SYNTHASE

FIELD OF THE INVENTION

The present invention is directed to the fields of molecular biology, molecular genetics, and organic chemistry. Specifically, the present invention is directed to the cloning and characterization of at least one *Ginkgo biloba* sequence for biosynthesis of ginkgolides. More specifically, the present invention is directed to the cloning, characterization and expression of *Ginkgo biloba* levopimaradiene synthase.

BACKGROUND OF THE INVENTION

The gymnosperm *Ginkgo biloba*, of the Conopsida class, Ginkgoales order, and Ginkgoaceae family, originated in Eastern China approximately 150 million years ago and is the sole living representative of its order (Schwarz and Arigoni, 1999; Benson, L., 1957; Chaw, et al., 2000; Bowe, et al., 2000). This hardy tree, termed a "living fossil" by Charles Darwin, is well-known for its ability to withstand harsh climate conditions and resist insect infestation (Major, R. T., 1967). The apparent lack of change over millions of years is presumably due to its long time span between generations; reproduction begins after 20 years of age and continues to 1000 years of age.

*G. biloba* is renowned as a potent herbal therapeutic that aids in the revascularization of ischemic tissue through improved microcirculation. *G. biloba* leaf extracts have been used for centuries to treat cerebrovascular and cardiovascular diseases, dementia, tinnitus, arthritis, and vertigo (Itil, et al., 1995; Briskin, D. P., 2000). These beneficial pharmacological effects have been attributed, in part, to the ginkgolides, a unique series of diterpene molecules which are highly specific platelet-activating factor (PAF) receptor antagonists (Hosford et al., 1990). Generation of PAF occurs during anaphylaxis or shock and leads to bronchoconstriction, contraction of smooth muscle, and reduced coronary blood flow, which are often fatal. The isomer known as ginkgolide B demonstrates the highest activity of the diterpenes and antagonizes all known PAF-induced membrane events. Furthermore, the American Medical Association recently endorsed the Chinese herb as a viable alternative to traditional approaches in the treatment of Alzheimer's disease. Recent studies report that the extract delayed the progression of dementia in approximately one third of the patients studied (Le Bars et al., 1997).

Ginkgolides were first isolated from the roots of the Ginkgo tree by Furukawa (1932) and later characterized by K. Nakanishi (1967) and Sakabe (1967); the elucidated structures were named Ginkgolides A, B, C, J, and M. In 1967, K. Okabe also established the presence of the ginkgolides in the leaves of the *Ginkgo* tree. Ginkgolides are biosynthesized from geranylgeranyl diphosphate, the universal diterpene precursor. These molecules contain a caged trilactone structure and display a rare tert-butyl group. Analogs are distinguished by the number and location of hydroxyl group substituents. Recently, the ginkgolides and bilobalide (a pentanorditerpenoid by-product of ginkgolide biosynthesis) were determined to have significant antifeedant activities toward insect larvae (Schwarz, M., 1994; Matsumoto, et al., 1987).

Geranylgeranyl diphosphate (GGDP) (Schwarz and Arigoni, 1999) employed in ginkgolide biosynthesis is derived from isopentenyl diphosphate formed via the deoxyxylulose pathway. The proposed biosynthesis of the ginkgolides is initiated by protonation of GGDP to give labdadienyl diphosphate. Ionization of the allylic diphosphate moiety followed by a 1,4-hydrogen shift, methyl migration, and deprotonation yields levopimaradiene (Schwarz and Arigoni, 1999). The proposed intramolecular hydrogen shift was also observed in the biosynthesis of *Abies grandis* abietadiene synthase (AgAS) (Ravn et al., 1998; Ravn et al., 2000). Oxidation of ring C produces abietatriene, which is then transported from the plastid to the cytoplasm. The aromatic hydrocarbon undergoes further transformation in the endoplasmic reticulum by cytochrome P450-dependent monooxygenases to produce the ginkgolides (Schwarz and Arigoni, 1999) (FIG. 1).

Metabolic regulation studies of diterpene production in *G. biloba* seedlings indicate that ginkgolides are produced in the roots and are subsequently translocated to the leaves. Furthermore, diterpene hydrocarbon precursors were found exclusively in the roots and included levopimaradiene, palustradiene, abietadiene, pimaradiene, and abietatriene. Addition of cytochrome P450-dependent oxygenase inhibitors to the roots of seedlings resulted in full inhibition of oxygenation reactions along the pathway to the diterpenes. Abietatriene, the sole diterpene hydrocarbon obtained, was identified as the immediate precursor to the ginkgolides (Cartayrade et al., 1997; Neau et al., 1997).

Presently, commercial development of the ginkgolides as therapeutic agents has been hampered. Because these diterpenoids contain up to 12 stereocenters, 4 contiguous quaternary carbons, and 3 oxacyclic rings fused to 2 spiro carbocyclic rings, they present a formidable synthetic challenge. In spite of the topological and stereochemical complexity inherent to the ginkgolides, total syntheses of these unusually challenging targets have been achieved. In 1988, the first synthesis of (±)-ginkgolide A (38 steps, <1% overall yield) and (±)-ginkgolide B (35 steps, <1% overall yield) were reported (Corey and Ghosh, 1988; Corey et al., 1988). Furthermore, ginkgolide B was converted to ginkgolide A in 6 steps and approximately 50% yield. More recently, (±)-ginkgolide B was synthesized in 26 steps and 3% total yield (Crimmins et al., 1999). Although strategically impressive, these demanding routes require multiple transformations resulting in low yields that ultimately preclude commercial-scale production of the ginkgolides.

Current commercial ginkgolide production relies exclusively on extraction from Ginkgo trees, which accumulate low levels of the compound. In addition, the demand for this medicinal plant has increased at a rate of 26% per annum with 2,000 tons harvested annually (Masood, E., 1997) *G. biloba* plantations serve as the major source of the herbal extract and provide an average 1 to 7 mg/g dry weight ginkgolide from young trees (Balz, et al., 1999) In an effort to increase diterpenoid content, *G. biloba* seedlings, plants, and trees were treated with metabolic inhibitors that target key branchpoints in isoprenoid biosynthesis downstream of GGPP synthesis (Huh, et al., 1993) Presumably, inhibiting GGPP depleting pathways would increase the available concentration of GGPP, the natural diterpene substrate. Variable results were obtained with cycloartenol synthase inhibitors, ancymidol and AMO-1618. In contrast, application of fluridone (an inhibitor of carotenoid biosynthesis that blocks phytoene desaturation) yielded up to 78% more ginkgolides.

Extraction of the ginkgolides from *G. biloba* is known. U.S. Pat. No. 5,399,348 refers to a method for preparation of *Ginkgo biloba* extract in which the alkylphenol compounds are separated not by using chlorinated aliphatic hydrocarbon, but through a process of precipitation, filtration and multi step liquid-liquid-extractions. U.S. Pat. Nos. 5,399,348; 5,322,688; 5,389,370; 5,389,370; 5,637,302; 5,512,286; 5,399,348; and 5,389,370 are all directed to various methods of preparing a desired *Ginkgo biloba* extract. U.S. Pat. Nos. 5,241,084 and 5,599,950 are directed to methods to convert ginkgolide C to ginkgolide B.

Seeking an alternative, non-synthetic approach to ginkgolide production, a method to clone and functionally express genes involved in their biosynthesis was considered. In 1971, the isoprenoid nature of the ginkgolides was precariously, yet correctly, established using 2-$^{14}$C MVA incorporation experiments conducted with *G. biloba* seedlings. Moreover, the researchers proposed that the unique tert-butyl group arose from S-adenosyl methionine (Nakanishi, et al., 1971). However, a revised biogenetic scheme was put forth as a result of NMR product analyses of isotopically labeled precursors incubated with *G. biloba* embryos (Schwarz, et al., 1999). During the course of these extensive studies, a dichotomy was observed concerning the biosynthesis of IPP by *G. biloba*. Specifically, formation of isopentenyl pyrophosphate (IPP), an isoprene unit possessing a diphosphate moiety, proceeds via the classical MVA pathway in the synthesis of sitosterol, but in the plastids, the deoxyxylulose-5-phosphate (DXP) pathway synthesizes GGPP. Presumably, segregation between the two pathways is due to compartmentalization of the plant cell. IPP responsible for sitosterol formation is restricted to the cytoplasm, and IPP incorporated into ginkgolides originates in the chloroplasts.

*G. biloba* cultures were first established in 1971; however, HPLC analysis failed to detect ginkgolides (Nakanishi, et al., 1971). Two decades later, ginkgolides A and B were detected in undifferentiated cell cultures (<20 ng/g dry weight), albeit by a factor of $10^6$ less than that obtained from leaves of mature trees (Carrier, et al., 1991; Chauret, et al., 1991). Increased ginkgolide content was demonstrated in primary callus and cell suspension cultures (~26% and 47% relative to leaves of mature trees, respectively) were unable to be maintained in secondary cultures (Huh, et al., 1993). Currently, high yield production of the ginkgolides by in vitro cultures of undifferentiated cells has not been achieved (Balz et al., 1999). Transgenic cells were obtained from putative transformed *G. biloba* embryos but ginkgolide concentration was <400 µg/g dry tissue culture (Laurain, et al., 1997). Recently, Dupréet al. (2000) reported a reproducible transformation protocol of *G. biloba* by *Agrobacterium tumefaciens*; however, ginkgolide levels of the transformed cells have not been disclosed.

There are examples in the art in which heterologous diterpene synthases are introduced into and expressed in organisms such as *Escherichia coli*, particularly for the purpose of characterizing activity of a soluble form of the enzyme in the absence of any plastidial targeting sequence (Hill et al., 1996; Peters et al., 2000; Williams et al., 2000). However, the novel levopimaradiene synthase of the present invention provides a solution to a need in the art for methods and compositions to quickly produce large amounts of substantially pure ginkgolides in a cost-effective manner, particularly in an organism capable of a high-yield ginkgolide-producing system.

SUMMARY OF THE INVENTION

One embodiment of the present invention is a purified and isolated nucleic acid sequence encoding a levopimaradiene synthase.

Another embodiment of the present invention is a purified and isolated nucleic acid sequence comprising, SEQ.ID.NO:1, SEQ.ID.NO:32, SEQ.ID.NO:34, SEQ.ID.NO:36 or SEQ.ID.NO:38.

An additional embodiment is a purified and isolated nucleic acid comprising SEQ.ID.NO:34. Another embodiment is a purified and isolated nucleic acid comprising SEQ.ID.NO:36.

Another embodiment of the present invention is an expression vector comprising an isolated and purified nucleic acid sequence encoding a levopimaradiene synthase under control of a promoter operable in a host cell. In a specific embodiment, the promoter is an inducible promoter, and preferably GAL1. In another specific embodiment, the nucleic acid sequence comprises SEQ.ID.NO:1, SEQ.ID.NO:32, SEQ.ID.NO:34, SEQ.ID.NO:36 or SEQ.ID.NO:38.

In yet another specific embodiment of the present invention, the host cell is a prokaryote, and preferably *Escherichia coli*. In another specific embodiment, the host cell is a eukaryote, and in a preferred specific embodiment the eukaryote is a yeast.

Another embodiment of the present invention is an isolated polypeptide having an amino acid sequence of a levopimaradiene synthase.

In another embodiment of the present invention there is an isolated polypeptide comprising an amino acid sequence of SEQ.ID.NO:2, SEQ.ID.NO:33, SEQ.ID.NO:35, SEQ.ID.NO:37 or SEQ.ID.NO:39.

Another embodiment of the present invention is an isolated polypeptide comprising an amino acid sequence of SEQ.ID.NO:35. Further, the present invention embodies an isolated polypeptide comprising an amino acid sequence of SEQ.ID.NO:37.

Another embodiment of the present invention is an expression vector comprising an isolated polynucleotide sequence encoding a polypeptide having an amino acid sequence of a levopimaradiene synthase. In a specific embodiment, the vector further comprises a promoter operatively linked to the polynucleotide sequence. In a further specific embodiment, the promoter is an inducible promoter. In a preferred specific embodiment, the inducible promoter is GAL1.

In another embodiment there is an isolated polynucleotide sequence encoding a polypeptide having an amino acid sequence of SEQ.ID.NO:2, SEQ.ID.NO:33, SEQ.ID.NO:35, SEQ.ID.NO:37 or SEQ.ID.NO:39. In a specific embodiment, the vector further comprises a promoter operatively linked to the polynucleotide sequence. In a further specific embodiment, the promoter is an inducible promoter and preferably GAL1.

In another embodiment of the present invention, there is a unicellular organism comprising a purified and isolated nucleic acid sequence encoding a levopimaradiene synthase. In a specific embodiment, the nucleic acid sequence comprises SEQ.ID.NO:1, SEQ.ID.NO:32, SEQ.ID.NO:34, SEQ.ID.NO:36 or SEQ.ID.NO:38. In a further specific embodiment, the nucleic acid sequence comprises an expression vector. In yet a further specific embodiment, the expression vector comprises an inducible promoter. In a preferred specific embodiment, the inducible promoter is GAL 1.

In another specific embodiment of the present invention, the nucleic acid sequence encoding the levopimaradiene synthase contains a deletion corresponding to an N-terminal sequence. In yet another specific embodiment, the organism is *Saccharomyces, Escherichia coli, Candida albicans* or

*Klyveromyces lactis*. In a preferred specific embodiment, the organism is *Escherichia coli*. In another preferred specific embodiment, the organism is *Saccharomyce cerevisiae*.

Another embodiment of the present invention is a yeast host cell comprising a vector, wherein the vector comprises a purified and isolated nucleic acid sequence comprising SEQ.ID.NO:1, SEQ.ID.NO:32, SEQ.ID.NO:34, SEQ.ID.NO:36, or SEQ.ID.NO:38 wherein said nucleic acid sequence is under control of a promoter operable in the yeast host cell. In a further specific embodiment, the nucleic acid sequence comprises an expression vector.

Yet another embodiment of the present invention is a yeast host cell comprising a vector, wherein the vector comprises an isolated polynucleotide sequence encoding a polypeptide having an amino acid sequence of SEQ.ID.NO:2, SEQ.ID.NO:33, SEQ.ID.NO:35, SEQ.ID.NO:37 or SEQ.ID.NO:39, wherein expression of the polynucleotide is under control of a promoter operable in the yeast host cell. In a further specific embodiment, the vector is an expression vector.

In one embodiment of the present invention there is a plant host cell, wherein the cell comprises an isolated and purified nucleic acid sequence comprising SEQ.ID.NO:1, SEQ.ID.NO:32, SEQ.ID.NO:34, SEQ.ID.NO:36 or SEQ.ID.NO:38, under control of a promoter operable in the yeast host cell. In a specific embodiment, the promoter is an inducible promoter. In another specific embodiment, the plant is *Ginkgo biloba*.

Another embodiment of the present invention there is a unicellular organism comprising an isolated polynucleotide sequence encoding a polypeptide having an amino acid sequence of a levopimaradiene synthase. In a specific embodiment the amino acid sequence comprises SEQ.ID.NO:2, SEQ.ID.NO:33, SEQ.ID.NO:35, SEQ.ID.NO:37 or SEQ.ID.NO:39. In another specific embodiment, the polynucleotide sequence contains a deletion corresponding to an N-terminal sequence of the levopimaradiene synthase.

In a specific embodiment, the unicellular organism is *Saccharomyces, Escherichia coli, Candida albicans*, or *Kluyveromyces lactis*. In other specific embodiments, the unicellular organism is *Saccharomyces cerevisiae* or *Escherichia coli*.

In one embodiment of the present invention there is a method of producing ginkgolide in a cell, comprising the steps of obtaining a cell comprising an isolated and purified nucleic acid sequence encoding a levopimaradiene synthase; culturing said cell under conditions wherein the cell produces ginkgolide; and removing the ginkgolide from the culture of cells. In a specific embodiment, the nucleic acid sequence comprises SEQ.ID.NO:1, SEQ.ID.NO:32, SEQ.ID.NO:34, SEQ.ID.NO:36 or SEQ.ID.NO:38. In a specific embodiment, the cell is *Saccharomyces cerevisiae*. In another specific embodiment, the cell is *Escherichia coli*. In a further specific embodiment, the nucleic acid sequence comprises an expression vector, wherein the expression vector includes an inducible promoter operatively linked to the levopimaradiene synthase coding region.

In another embodiment of the present invention there is a method of producing levopimaradiene in a cell, comprising the steps of obtaining a cell comprising an isolated and purified nucleic acid sequence encoding a levopimaradiene synthase; culturing the cell under conditions wherein the cell produces levopimaradiene; and removing the levopimaradiene from the culture of cells. In a specific embodiment, the nucleic acid sequence comprises SEQ.ID.NO:1, SEQ.ID.NO:32, SEQ.ID.NO:34, SEQ.ID.NO:36 or SEQ.ID.NO:38. In a further specific embodiment, the nucleic acid sequence comprises an expression vector, wherein the expression vector includes an inducible promoter operatively linked to the levopimaradiene synthase coding region.

In another embodiment of the present invention there is a method of producing a ginkgolide in a yeast cell, comprising the steps of obtaining a cell wherein an isolated and purified nucleic acid sequence of SEQ.ID.NO:1, SEQ.ID.NO:32, SEQ.ID.NO:34, SEQ.ID.NO:36 or SEQ.ID.NO:38 under control of a promoter operable in the yeast cell has been added to the yeast cell; culturing the cell under conditions wherein the yeast cell produces the ginkgolide; and removing the ginkgolide from the culture of yeast cells. In a specific embodiment, the nucleic acid sequence further comprises an inducible promoter.

In another embodiment of the present invention there is a method of producing levopimaradiene in a yeast cell, comprising the steps of obtaining a yeast cell wherein an isolated and purified nucleic acid sequence of SEQ.ID.NO:1, SEQ.ID.NO:32, SEQ.ID.NO:34, SEQ.ID.NO:36 or SEQ.ID.NO:38 under control of a promoter operable in the yeast cell has been added to the yeast cell; culturing the yeast cell under conditions wherein the yeast cell produces the levopimaradiene; and removing the levopimaradiene from the culture of yeast cells. In a further embodiment, the nucleic acid sequence and the promoter comprise an expression vector.

In another embodiment of the present invention there is a method of producing levopimaradiene in a yeast cell, comprising the steps of obtaining a yeast cell wherein an isolated polynucleotide sequence encoding a polypeptide having an amino acid sequence of a levopimaradiene synthase under control of a promoter operable in the yeast cell has been added to the yeast cell; culturing the yeast cell under conditions wherein the yeast cell produces the levopimaradiene; and removing the levopimaradiene from the culture of yeast cells.

In a specific embodiment, the promoter is an inducible promoter. In another specific embodiment, the amino acid sequence comprises SEQ.ID.NO:2, SEQ.ID.NO:33, SEQ.ID.NO:35, SEQ.ID.NO:37 or SEQ.ID.NO:39.

Another embodiment of the present invention is a method of producing levopimaradiene in a cell, comprising the steps of obtaining a yeast cell, wherein an isolated and purified nucleic acid sequence of SEQ.ID.NO:1, SEQ.ID.NO:32, SEQ.ID.NO:34, SEQ.ID.NO:36 or SEQ.ID.NO:38 under control of a promoter operable in the yeast cell has been added to the yeast cell and the yeast cell further comprises an increase in the effective amount of geranylgeranyl diphosphate; growing a culture of the yeast cells; and removing the levopimaradiene from the culture of yeast cells.

In another embodiment of the present invention, there is a ginkgolide, wherein said ginkgolide is obtained from production in a unicellular organism comprising a purified and isolated nucleic acid sequence encoding a levopimaradiene synthase.

In another embodiment of the present invention, there is a ginkgolide, wherein said ginkgolide is obtained from production in a unicellular organism comprising a purified and isolated nucleic acid sequence of SEQ.ID.NO:1, SEQ.ID.NO:32, SEQ.ID.NO:34, SEQ.ID.NO:36 or SEQ.ID.NO:38.

Another embodiment of the present invention is a ginkgolide, wherein the ginkgolide is obtained from production in a unicellular organism comprising an expression vector having an isolated and purified nucleic acid sequence encoding a levopimaradiene synthase under control of a promoter operable in the organism.

Another embodiment of the present invention is a ginkgolide, wherein the ginkgolide is obtained from production in a unicellular organism, wherein the organism comprises an isolated polynucleotide sequence encoding a polypeptide having an amino acid sequence of SEQ.ID.NO:2, SEQ.ID.NO:33, SEQ.ID.NO:35, SEQ.ID.NO:37 or SEQ.ID.NO:39.

In another embodiment of the present invention, there is a ginkgolide, wherein said ginkgolide is obtained from the method of producing the ginkgolide in a cell comprising the steps of obtaining a culture of cells wherein at least one cell comprises a purified and isolated nucleic acid sequence encoding a levopimaradiene synthase; culturing the cell under conditions wherein the cell produces the ginkgolide; and removing the ginkgolide from the culture of cells. In a specific embodiment, the nucleic acid sequence comprises SEQ.ID.NO:1, SEQ.ID.NO:32, SEQ.ID.NO:34, SEQ.ID.NO:36 or SEQ.ID.NO:38.

In another embodiment of the present invention, there is a ginkgolide, wherein said ginkgolide is obtained from the method of producing the ginkgolide in a yeast cell, comprising the steps of obtaining a culture of yeast cells, wherein at least one yeast cell comprises a purified and isolated nucleic acid sequence of SEQ.ID.NO:1, SEQ.ID.NO:32, SEQ.ID.NO:34, SEQ.ID.NO:36 or SEQ.ID.NO:38; culturing the yeast cell under conditions wherein the yeast cell produces the ginkgolide; and removing the ginkgolide from the culture of yeast cells.

In another embodiment of the present invention, there is a ginkgolide, wherein said ginkgolide is obtained from production in a unicellular organism which includes an isolated polynucleotide sequence encoding a polypeptide having an amino acid sequence of a levopimaradiene synthase, wherein the polynucleotide sequence comprises a deletion corresponding to an N-terminal sequence; culturing the cell under conditions wherein the cell produces the ginkgolide; and removing the ginkgolide from the culture of cells. In a specific embodiment, the amino acid sequence comprises SEQ.ID.NO:33, SEQ.ID.NO:35, SEQ.ID.NO:37 or SEQ.ID.NO:39.

In an additional embodiment of the present invention, there is a nucleic acid sequence comprising SEQ.ID.NO:5, SEQ.ID.NO:6, SEQ.ID.NO:7, SEQ.ID.NO:8, SEQ.ID.NO:9, SEQ.ID.NO:10, SEQ.ID.NO:11, SEQ.ID.NO:12, SEQ.ID.NO:29, SEQ.ID.NO:30, SEQ.ID.NO:31 or SEQ.ID.NO:40.

In an additional embodiment of the present invention there is a transgenic plant, wherein the plant comprises a purified and isolated nucleic acid sequence encoding a levopimaradiene synthase under control of a promoter operable in the plant. In a specific embodiment, the plant is *Ginkgo biloba*. In another specific embodiment, the nucleic acid sequence comprises SEQ.ID.NO:1, SEQ.ID.NO:32, SEQ.ID.NO:34, SEQ.ID.NO:36 or SEQ.ID.NO:38.

In another specific embodiment, there is a seed of the transgenic plant. In a preferred embodiment, the seed is *Ginkgo biloba*.

Other and further objects, features, and advantages are apparent and eventually more readily understood by reading the following specification and the accompanying drawings forming a part thereof, or any examples of the presently preferred embodiments of the invention given for the purpose of the disclosure.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein:

FIG. 4 illustrates amino acid sequence alignment of plant sesquiterpene and diterpene synthases.

DESCRIPTION OF THE INVENTION

Figure 1:
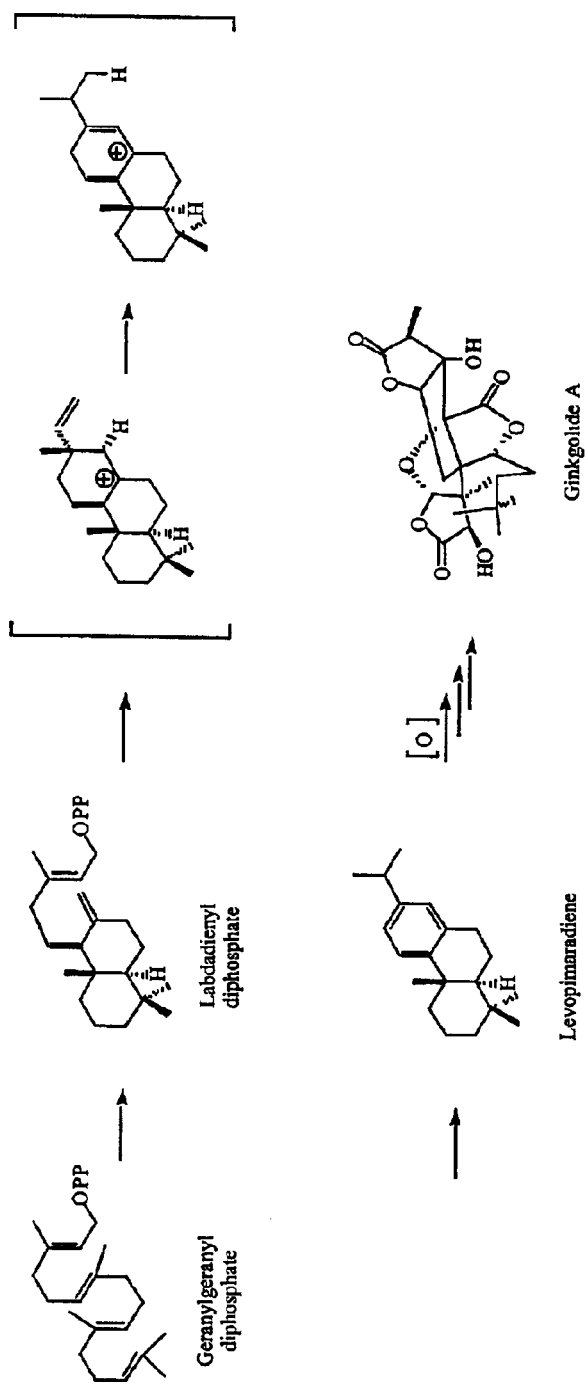
FIG. 1 depicts the biosynthesis of ginkgolide A from geranylgeranyl diphosphate (GGDP).
Figure 2:
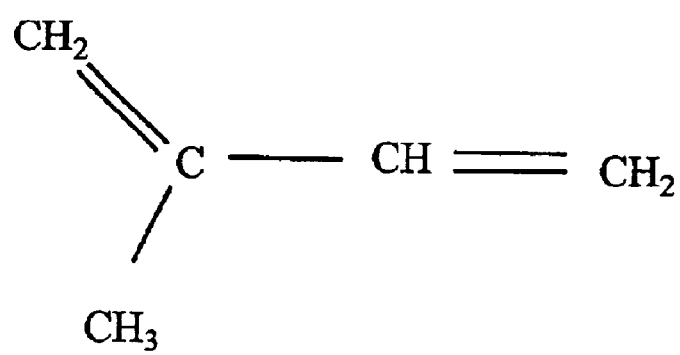
FIG. 2 illustrates the structure of an isoprene unit.

It will be readily apparent to one skilled in the art that various embodiments and modifications may be made in the invention disclosed herein without departing from the scope and spirit of the invention.

As used in the specification, "a" or "an" may mean one or more. As used in the claim(s), when used in conjunction with the word "comprising", the words "a" or "an" may mean one or more than one. As used herein "another" may mean at least a second or more.

The technology of the present invention is related to the invention described in the U.S. Patent Application entitled, "Diterpene-Producing Unicellular Organism" filed on the same day and incorporated by reference herein.

I. Definitions

The term "diterpene" as used herein is defined as a terpene compound comprised of four isoprene units to yield a 20-carbon hydrocarbon structure. The 20 carbon acyclic structure is called geranylgeranyl pyrophosphate (GGPP) or equally correct, geranylgeranyl diphosphate (GGDP). A skilled artisan is aware that diterpenes result from metabolism of GGPP and, thus may, after metabolism, yield a structure possessing one or more rings, one or more double bonds or one or more hydroxyl group. Non-limiting examples of diterpenes are levopimaradiene copalol, abietadiene and abietatriene.

The term "GGDP" as used herein is defined as geranylgeranyl diphosphate. The term may be used interchangeably with geranylgeranyl pyrophosphate (GGPP).

The term "GGPP" as used herein is defined as geranylgeranyl pyrophosphate. The term may be used interchangeably with geranylgeranyl diphosphate (GGDP).

The term "diterpenoid" as used herein is defined as a metabolite of a diterpene. One skilled in the art recognizes that a diterpene is often further transformed and, thus, may possess in an intermediate or final structure, more or less than the starting 20-carbons, one or more functional groups such as, for example, an ether, a carbonyl, an hydroxyl group or an aromatic ring.

The term "ginkgolide" as used herein is defined as a diterpenoid from the *Ginkgo biloba* plant. A skilled artisan is aware that there are at least the following naturally occurring ginkgolides: Ginkgolide A, Ginkgolide B, Ginkgolide C, Ginkgolide M, and Ginkgolide J. A skilled artisan is also aware that there are additionally many derivatives thereof, such as, for example, a ketone (i.e., an acetate) at least one of any of the R groups in FIG. 3. A skilled artisan is aware that functional groups are often altered on a structure to effect characteristics such as, for example, solubility, and is very important in developing, for example, efficacious pharmaceuticals and medicaments.

The term "gymnosperm" as used herein is defined as a plant whose seeds are not enclosed within an ovary. Gymnosperms are contained in four phyla: Cycadophyta, Ginkgophyta, Pinophyta, and Gnetophyta. Examples include ginkgo, cycad, yew and conifer. A skilled artisan is aware of readily accessible databases that provide a comprehensive list of specific examples.

The term "levopimaradiene synthase" as used herein is defined as an enzyme which catalyzes the synthesis of levopimaradiene from geranylgeranyl diphosphate through ionization of the allylic diphosphate moiety of labdadienyl pyrophosphate, followed by 1,4 hydrogen shift, methyl migration, and deprotonation.

II. The Present Invention

Levopimaradiene synthase is useful to produce the ginkgolide precursor levopimaradiene. Potential levopimaradiene production methods of the present invention include in vitro conversion of geranylgeranyl diphosphate (GGDP) and in vivo production (in *Ginkgo* or microorganisms) using biosynthetic GGDP at native levels or in organisms genetically modified to increase the effective amount of geranylgeranyl diphosphate levels. The increase in the effective amount of GGDP allows more substrate (e.g., GGDP) to be available for conversion to levopimaradiene and other enzyme diterpene products without the host organism suffering adverse consequences of low (i.e., below required levels) GGDP levels.

Levopimaradiene synthase overexpression in *Ginkgo* in a specific embodiment allows increased levels of more advanced ginkgolide precursors. In alternative embodiments, additional genes are incorporated for increased quantities of levopimaradiene synthase, thereby leading to increased quantities of levopimaradiene or a ginkgolide. Expression of levopimaradiene synthase, which preferably does not contain a plastidial targeting sequence (see, for example, Peters et al. (2000); Williams et al. (2000)), in organisms that express genes encoding enzymes to metabolize GGDP, whether GGDP is exogenously provided or produced de novo, provide production of ginkgolide or ginkgolide precursors. One such ginkgolide precursor is levopimaradiene.

Levopimaradiene synthase, which directs the first committed step in ginkgolide biosynthesis, was cloned and characterized to ultimately isolate and functionally express genes involved in ginkgolide biosynthesis. This gene is essential to overproduction of ginkgolide using genetically modified organisms. A skilled artisan is aware that if the synthase exhibits low solubility and expression in *Escherichia coli*, *Saccharomyces cerevisiae* or other expression hosts, alternative strains and/or gene truncations are employed.

*Ginkgo biloba* levopimaradiene synthase is a cytosolically-synthesized plastid protein containing an N-terminal sequence that directs translocation of the levopimaradiene to specific plastidial compartments. The signal sequence is then excised by a specific protease, yielding a mature levopimaradiene synthase. The optimal truncation site is determined through, for example, expression studies of the full-length gene and truncated versions, as described herein. The present invention contemplates a levopimaradiene synthase nucleic acid sequence and amino acid sequence that contains a deletion in the N-terminal sequence.

A skilled artisan is aware of standard means in the art to identify other levopimaradiene synthase nucleic acid sequences or other nucleic acid sequences which encode gene products that are functionally interchangeable with levopimaradiene synthase, meaning catalyze production of a deterpene, for example by searching publicly available sequence repositories such as GenBank or commercially available sequence repositories that are readily available. The SEQ.ID.NO:1 nucleic acid sequence is the *Ginkgo biloba* levopimaradiene synthase nucleic acid sequence, which encodes the *Ginkgo biloba* levopimaradiene synthase amino acid sequence (SEQ.ID.NO:2). A GenBank search with SEQ.ID.NO:1, the *Ginkgo biloba* levopimaradiene synthase nucleic acid sequence, identifies the similar sequence *Abies grandis* abietadiene synthase U50768.1 (SEQ.ID.NO:3) that encodes AAB05407 (SEQ.ID.NO:4), which is also in the scope of the present invention. A skilled artisan is aware of other standard methods to clone sequences, such as by library screening through hybridization to similar sequences.

Standard methods and reagents in the field of yeast molecular genetics, particularly regarding *Saccharomyces cerevisiae*, are well known in the art. References for such methods include *Methods in Yeast Genetics*, 2000 *Edition: A Cold Spring Harbor Laboratory Course Manual* (Burke et al., 2000) and *Current Protocols in Molecular Biology*, Chapter 13 (Ausubel et al., 1994), both incorporated by reference herein. A skilled artisan is aware that the *Saccharomyces* species of choice is *S. cerevisiae*, although there are other known species of the genus *Saccharomyces* including *S. italicus, S. oviformis, S. capensis, S. chevalieri, S. douglasii, S. paradoxus, S. cariocanus, S. kudriavzevii, S. mikatae, S. bayanus,* and *S. pastorianus*.

III. Ginkgolides

A ginkgolide is a diterpenoid from the *Ginkgo biloba* plant. Examples include the following naturally occurring ginkgolides Ginkgolide A, Ginkgolide B, Ginkgolide C, Ginkgolide M, Ginkgolide J, in addition to other derivatives such as a substituent(s) effecting solubility but not catalytic activity. A skilled artisan is aware of such moieties and methods to determine effects such as a desired solubility, electronic interaction, coordination and the other such properties without compromising biological activity. Preferable ginkgolides which are generated with the methods and compositions of the present invention include: Ginkgolide A and Ginkgolide B.

Figure 3:
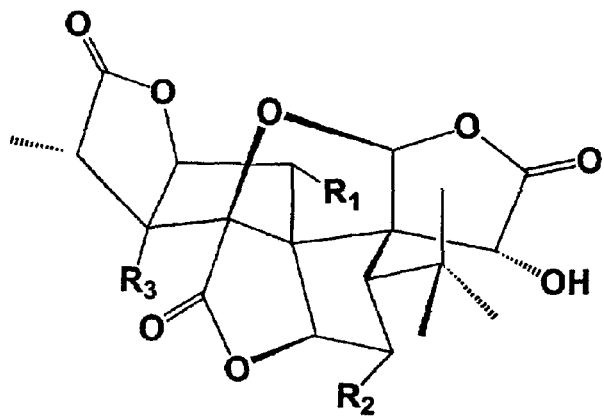
FIG. 3 illustrates the parent ginkgolide chemical structure.

FIG. 3 demonstrates a generic ginkgolide structure with non-limiting examples of substitutents for $R_1$, $R_2$, $R_3$ and $R_4$ given in the chart.

IV. Nucleic Acid-Based Expression Systems

A. Vectors

The term "vector" is used to refer to a carrier nucleic acid molecule into which a nucleic acid sequence is inserted for introduction into a cell where it is replicated. A nucleic acid sequence is in one instance "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al, 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors, in one instance, contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," "under control of a promoter operable in" and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter is referred to as "endogenous." Similarly, an enhancer may be one naturally associated with a nucleic acid sequence, located either downstream or upstream of that sequence. Alternatively, certain advantages are gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference). Furthermore, it is contemplated the control sequences that direct transcription and/or expression of sequences within non-nuclear organelles such as mitochondria, chloroplasts, and the like, is be employed as well.

Naturally, it is important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that is activated in response to a specific stimulus.

TABLE 1

| Promoter/Enhancer | Promoter and/or Enhancer References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α$_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 1-continued

Promoter and/or Enhancer

| Promoter/Enhancer | References |
|---|---|
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al, 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al, 1996).

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons are either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements are, in one instance, linked to heterologous open reading frames. Multiple open reading frames are transcribed together, each separated by an IRES, creating polycistronic messages. By virtue of the IRES element, each open reading frame is accessible to ribosomes for efficient translation. Multiple genes are efficiently expressed using a single promoter/enhancer to transcribe a single message (see U.S. Pat. Nos. 5,925,565 and 5,935,819, herein incorporated by reference).

3. Multiple Cloning Sites

Vectors include, in some instances, a multiple cloning site (MCS), which is a nucleic acid region that contains multiple restriction enzyme sites, any of which are used in conjunction with standard recombinant technology to digest the vector. (See Carbonelli et al, 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Polyadenylation Signals

In expression, one typically includes a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements serve to enhance message levels and/or to minimize read through from the cassette into other sequences.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) is employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product, such as a levopimaradiene synthase. Further examples of selectable and screenable markers are well known to one of skill in the art, such as amino acid markers including, but not limited to, uracil, leucine, tryptophan and histidine biosynthetic genes. A host that is auxotrophic for the amino acid biosynthetic gene used as a selectable marker allows ready screening for transformer cells comprising the nucleic acid sequence of interest.

B. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell is, in most instances, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they are obtained through, for example, the American Type Culture Collection (ATCC), which is an organization that serves as an archive for living cultures and genetic materials. An appropriate host is determined by one of skill in the art based on the vector backbone and the desired result. A plasmid or cosmid, for example, is introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as $E.$ $coli$ LE392 are used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Another such host cell is a cell that accumulates an increase in the amount of geranylgeranyl diphosphate that is biosynthesized de novo. An example of such a microorganism is described in co-pending application "Diterpene-producing unicellular organism", filed on the same day as the instant application. The increase in the amount of substrate for levopimaradiene synthase (e.g., geranylgeranyl diphosphate) allows a proportional increase in levopimaradiene production.

C. Expression Systems

Numerous expression systems exist that comprise at least a part or all of the compositions discussed above. Prokaryote- and/or eukaryote-based systems are employed for use with the present invention to produce nucleic acid sequences, or their cognate polypeptides, proteins and peptides. Many such systems are commercially and widely available.

The insect cell/baculovirus system produce a high level of protein expression of a heterologous nucleic acid segment, such as described in U.S. Pat. Nos. 5,871,986, 4,879,236, both herein incorporated by reference, and which are bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its $E.$ $coli$ pET Bacterial Expression System. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

V. Nucleic Acid Detection

In addition to their use in directing the expression of levopimaradiene synthase proteins, polypeptides and/or peptides, the nucleic acid sequences disclosed herein have a variety of other uses. For example, they have utility as probes or primers for embodiments involving nucleic acid hybridization.

A. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One generally prefers to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence. h For applications requiring high selectivity, one typically desires to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions are rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions are readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it is advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that are employed to provide a detection means that is visibly or spectrophotometrically detectable, to identify specific hybridization with complementary nucleic acid containing samples.

In general, it is envisioned that the probes or primers described herein are useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences are also contemplated. Primers are provide in double-stranded and/or single-stranded form, although the single-stranded form is preferred.

Pairs of primers designed to selectively hybridize to nucleic acids corresponding to levopimaradiene synthase are contacted with the template nucleic acid under conditions that permit selective hybridization. Depending upon the desired application, high stringency hybridization conditions are selected that only allow hybridization to sequences that are completely complementary to the primers. In other embodiments, hybridization occurs under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product is detected or quantified. In certain applications, the detection is performed by visual means. Alternatively, the detection involves indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR ™ amplification procedure is performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that are used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, is also used as an amplification method in the present invention. In this method, a replicative sequence of RNA that has a region complementary to that of a target is added to a sample in the presence of an RNA polymerase. The polymerase copies the replicative sequence which then are detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which is used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products are cut out and eluted from the gel for further manipulation. Using low melting point agarose gels, the separated band is removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products are exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that are used in the practice of the instant invention are disclosed in U.S. Pat. Nos. 5,840,873, 5,843,640, 5,843,651, 5,846,708, 5,846, 717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening are used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that are used in the practice of the present invention are disclosed in U.S. Pat. Nos. 5,849,483, 5,851,770, 5,866,337, 5,925,525 and 5,928,870, each of which is incorporated herein by reference in its entirety.

VI. Site-Directed Mutagenesis

Structure-guided site-specific mutagenesis (also called site-directed mutagenesis) represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as E. coli polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as E. coli cells, and clones are selected that include recombinant vectors bearing the mutated sequence arrangement.

Comprehensive information on the functional significance and information content of a given residue of protein is best be obtained by saturation mutagenesis in which all 19 amino acid substitutions are examined. The shortcoming of this approach is that the logistics of multiresidue saturation mutagenesis are daunting (Warren et al, 1996, Brown et al., 1996; Zeng et al., 1996; Burton and Barbas, 1994; Yelton et al., 1995; Jackson et al., 1995; Short et aL, 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

VII. Levopimaradiene Synthase Nucleic Acids

A. Nucleic Acids and Uses Thereof

Certain aspects of the present invention concern at least one levopimaradiene synthase nucleic acid. In certain aspects, the at least one levopimaradiene synthase nucleic acid comprises a wild-type or mutant levopimaradiene synthase nucleic acid. In particular aspects, the levopimaradiene synthase nucleic acid encodes for at least one transcribed nucleic acid. In certain aspects, the levopimaradiene synthase nucleic acid comprises at least one transcribed nucleic acid. In particular aspects, the levopimaradiene synthase nucleic acid encodes at least one levopimaradiene synthase protein, polypeptide or peptide, or biologically functional equivalent thereof. In other aspects, the levopimaradiene synthase nucleic acid comprises at least one nucleic acid segment of SEQ.ID.NO:1, or at least one biologically functional equivalent thereof, for example SEQ.ID.NO:32, SEQ.ID.NO:34, SEQ.ID.NO:36, or SEQ.ID.NO:38.

A skilled artisan is aware that a nucleic acid sequence of the present invention may be contained on an episome, such as a plasmid or other vector, or may be on a chromosome of an organism, or both.

The present invention also concerns the isolation or creation of at least one recombinant construct or at least one recombinant host cell through the application of recombinant nucleic acid technology known to those of skill in the art or as described herein. The recombinant construct or host cell may comprise at least one levopimaradiene synthase nucleic acid, and may express at least one levopimaradiene synthase protein, polypeptide or peptide, or at least one biologically functional equivalent thereof.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. No. 5,705,629, each incorporated herein by reference. A non-limiting example of enzymatically produced nucleic acid include one produced by enzymes in amplification reactions such as PCR™ (see for example, U.S. Pat. Nos. 4,683,202 and 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" generally refers to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a levopimaradiene synthase nucleic acid. In particular embodiments the invention encompasses at least one nucleic acid or nucleic acid segment complementary to the sequence set forth in SEQ.ID.NO:1, SEQ.ID.NO:32, SEQ.ID.NO:34, SEQ.ID.NO:36, and/or SEQ.ID.NO:38. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent(s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally forms one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, carboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 carbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like. Purine and pyrimidine derivatives and mimics are well known in the art.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar (Kornberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein.

A non-limiting example of a nucleic acid comprising such nucleoside or nucleotide derivatives and mimics is a "polyether nucleic acid", described in U.S. Pat. No. 5,908,845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm et al., Nature 1993, 365, 566; PCT/EP/

01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA may to a target sequence has applications the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. Pat. No. 5,891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 117,363, filed Sep. 3, 1993, describes several alkylamino functionalities and their use in the attachment of such pendant groups to oligonucleosides. U.S. application Ser. No. 07/943,516, filed Sep. 11, 1992, and its corresponding published PCT application WO 94/06815, describe other novel amine-containing compounds and their incorporation into oligonucleotides for, inter alia, the purposes of enhancing cellular uptake, increasing lipophilicity, causing greater cellular retention and increasing the distribution of the compound within the cell.

Additional non-limiting examples of nucleosides, nucleotides or nucleic acids comprising 5-carbon sugar and/or backbone moiety derivatives or mimics are well known in the art.

In certain aspect, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly plant cells, and more particularly *Ginkgo biloba* cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from *Ginkgo biloba* would be an "isolated *Ginkgo biloba* nucleic acid", and the like.

Of course, more than one copy of an isolated nucleic acid may be isolated from biological material, or produced in vitro, using standard techniques that are known to those of skill in the art. In particular embodiments, the isolated nucleic acid is capable of expressing a protein, polypeptide or peptide that has diterpene synthase activity, such as levopimaradiene synthase activity. In other embodiments, the isolated nucleic acid comprises an isolated levopimaradiene synthase gene.

Herein certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In other particular aspects, the gene comprises a levopimaradiene synthase nucleic acid, and/or encodes a levopimaradiene synthase polypeptide or peptide coding sequences. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As is understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest, in this case the levopimaradiene synthase gene(s), forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment", are smaller fragments of a nucleic acid, such as for non-limiting example, those that encode only part of the levopimaradiene synthase peptide or polypeptide sequence. Thus, a "nucleic acid segment" may comprise any part of the levopimaradiene synthase gene sequence(s), of from about 2 nucleotides to the full length of the levopimaradiene synthase peptide or polypeptide encoding region. In certain embodiments, the "nucleic acid segment" encompasses the full length levopimaradiene synthase gene(s) sequence. In particular embodiments, the nucleic acid comprises any part of the SEQ.ID.NO:1 sequence(s), of from about 2 nucleotides to the full length of the sequence disclosed in SEQ.ID.NO:1.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). The length overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ.ID.NO:1. A nucleic acid construct may be about 3, about 5, about 8, about 10 to about 14, or about 15, about 20, about 30, about 40, about 50, about 100, about 200, about 500, about 1,000, about 2,000, about 3,000, about 5,000, about 10,000, about 15,000, about 20,000, about 30,000, about 50,000, about 100,000, about 250,000, about 500,000, about 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It is readily understood that "intermediate lengths" and "intermediate ranges", as used herein, means any length or range including or between the quoted values (i.e. all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 1,001, about 1002, etc,; about 50,001, about 50,002, etc; about 750,001, about 750,002, etc.; about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

In particular embodiments, the invention concerns one or more recombinant vector(s) comprising nucleic acid sequences that encode a levopimaradiene synthase protein, polypeptide or peptide that includes within its amino acid sequence a contiguous amino acid sequence in accordance with, or essentially as set forth in, SEQ.ID.NO:2, corresponding to Ginkgo biloba levopimaradiene synthase. In particular aspects, the recombinant vectors are DNA vectors.

The term "a sequence essentially as set forth in SEQ.ID.NO:2" means that the sequence substantially corresponds to a portion of SEQ.ID.NO:2 and has relatively few amino acids that are not identical to, or a biologically functional equivalent of, the amino acids of SEQ.ID.NO:2. Accordingly, a sequence that has between about 70% and about 80%; or more preferably, between about 81% and about 90%; or even more preferably, between about 91% and about 99%; of amino acids that are identical or functionally equivalent to the amino acids of SEQ.ID.NO:2 is a sequence that is "essentially as set forth in SEQ.ID.NO:2". Thus, "a sequence essentially as set forth in SEQ.ID.NO:1" encompasses nucleic acids, nucleic acid segments, and genes that comprise part or all of the nucleic acid sequences as set forth in SEQ.ID.NO:1, wherein the sequence that has between about 70% and about 80%; or more preferably, between about 81% and about 90%; or even more preferably, between about 91% and about 99%; of amino acids that are identical or functionally equivalent to the nucleic acids of SEQ.ID.NO:1.

The term "biologically functional equivalent" is well understood in the art and is further defined in detail herein. A nucleic acid sequence encoding a polypeptide that performs an equivalent function to the polypeptide of amino acid SEQ.ID.NO:2 is a sequence that is a "biologically functional equivalent" protein, polypeptide or peptide. Likewise, the nucleic acid sequence encoding the biologically functional equivalent polypeptide is also contemplated within the scope of the invention.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon is altered to any of the corresponding codons described without altering the encoded polypeptide. Such nucleic acid variations are "silent variations" and represent one species of conservatively modified variation. Every nucleic acid sequence herein which encodes a polypeptide also describes every possible silent variation of the nucleic acid. One of ordinary skill recognizes that each codon in a nucleic acid (except AUG, which is ordinarily the only codon for methionine; and UGG, which is ordinarily the only codon for tryptophan) is modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill recognizes that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 is so altered. Thus, for example, 1, 2, 3, 4, 5, 7, or 10 alterations are made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

In certain other embodiments, the invention concerns at least one recombinant vector that include within its sequence a nucleic acid sequence essentially as set forth in SEQ.ID.NO:1. In particular embodiments, the recombinant vector comprises DNA sequences that encode protein(s), polypeptide(s) or peptide(s) exhibiting levopimaradiene synthase activity.

It also understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of SEQ.ID.NO:1 are nucleic acid sequences that are "essentially as set forth in SEQ.ID.NO:1".

It also understood that this invention is not limited to the particular nucleic acid of SEQ.ID.NO:1 or amino acid sequences of SEQ.ID.NO:2. Recombinant vectors and isolated nucleic acid segments may therefore variously include these coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present invention encompass biologically functional equivalent levopimaradiene synthase proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine levopimaradiene synthase protein, polypeptide or peptide activity at the molecular level.

Fusion proteins, polypeptides or peptides may be prepared, e.g., where the levopimaradiene synthase-coding regions are aligned within the same expression unit with other proteins, polypeptides or peptides having desired functions. Non-limiting examples of such desired functions of expression sequences include purification or immunodetection purposes for the added expression sequences, e.g., proteinaceous compositions that may be purified by affinity chromatography or the enzyme labeling of coding regions, respectively.

Encompassed by the invention are nucleic acid sequences encoding relatively small peptides or fusion peptides, such as, for example, peptides of from about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, to about 100 amino acids in length, or more preferably, of from about 15 to about 30 amino acids in length; as set forth in SEQ.ID.NO:2 and also larger polypeptides up to and including proteins corresponding to the full-length sequences set forth in SEQ.ID.NO:2.

As used herein an "organism" may be a prokaryote, eukaryote, virus and the like. As used herein the term "sequence" encompasses both the terms "nucleic acid" and "proteinaceous" or "proteinaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

VIII. Methods for Plant Transformation

Suitable methods for plant transformation for use with the current invention are believed to include virtually any method by which DNA is introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384,253, specifically incorporated herein by reference in its entirety), by agitation with silicon carbide fibers (Kaeppler et al, 1990; U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), and the like. Through the application of techniques such as these, maize cells as well as those of virtually any other plant species may be stably transformed, and these cells developed into transgenic plants. In certain embodiments, acceleration methods are preferred and include, for example, microprojectile bombardment and the like.

A transgenic plant may require seed propagation, and in such instances, a seed of the transgenic plant embodies the recombinant gene therein. In the case of Ginkgo, the genetic content of the seeds is particularly enriched for ginkgolide production. Thus, the seed of a transgenic plant is characterized by increased amounts of a ginkgolide and is a reasonable means to propagate the transgenic plant that is the resource for the sought-after ginkgolide.

A. Electroporation

Where one wishes to introduce DNA by means of electroporation, it is contemplated that the method of Krzyzek et al. (U.S. Pat. No. 5,384,253, incorporated herein by reference in its entirety) is particularly advantageous. In this method, certain cell wall-degrading enzymes, such as pectin-degrading enzymes, are employed to render the target recipient cells more susceptible to transformation by electroporation than untreated cells. Alternatively, recipient cells are made more susceptible to transformation by mechanical wounding.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

B. Microprojectile Bombardment

A preferred method for delivering transforming DNA segments to plant cells in accordance with the invention is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which is used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

C. Agrobacterium-mediated Transformation

Agrobacterium-mediated transfer is a widely applicable system for introducing genes into plant cells because the DNA is introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; Zhang et al., 1997; U.S. Pat. No. 5,591,616, specifically incorporated herein by reference in its entirety), wheat (McCormac et al., 1998), barley (Tingay et al., 1997; McCormac et al., 1998), and maize (Ishidia et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed $T_i$ genes are used for the transformations. In those plant strains where Agrobacterium-mediated transformation is efficient, it is the method of choice because of the facile and defined nature of the gene transfer.

D. Other Transformation Methods

Transformation of plant protoplasts is achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Fujimara et al., 1985; Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that are not successfully regenerated from protoplasts, other ways to introduce DNA into intact cells or tissues are utilized. For example, regeneration of cereals from immature embryos or explants are effected as described (Vasil, 1989). Also, silicon carbide fiber-mediated transformation is used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cell are punctured. This technique has been used successfully with, for example, the monocot cereals maize (PCT Application WO 95/06128, specifically incorporated herein by reference in its entirety; Thompson, 1995) and rice (Nagatani, 1997).

An embodiment of the present invention is to produce significant amounts of ginkgolide precursors and/or ginkgolide in vivo in Ginkgo or microorganisms such as *Saccharomyces cerevisiae, Escherichia coli, Candida albicans*, and the like. Cell suspension cultures of *Ginkgo biloba* are known in the art (Balz et al., 1999; Fiehe et al., 2000).

In a preferred embodiment, ginkgolide precursors and/or ginkgolides are produced in vivo by expressing a nucleic acid sequence which encodes *Ginkgo biloba* levopimaradiene synthase, which is a rate-limiting step in the ginkgolide biosynthesis. In another preferred embodiment, the expression is upregulated, or "overexpressed" compared to native levels in wild type. A skilled artisan is aware how to achieve overexpression, such as by controlling regulation of the *Ginkgo biloba* levopimaradiene synthase with a strong promoter, examples of which are known in the art. In another preferred embodiment, the promoter is an inducible promoter, such as GAL1.

EXAMPLES

The following examples are included to demonstrate preferred embodiments of the invention. It should be appreciated by those skilled in the art that the techniques disclosed in the examples which follow represent techniques discovered by the inventor to function well in the practice of the invention, and thus is considered to constitute preferred modes for its practice. However, those of skill in the art should, in light of the present disclosure, appreciate that many changes made in the specific embodiments which are disclosed and maintain a like or similar result without departing from the concept, spirit and scope of the invention. More specifically, it is apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Methods-Plant Materials, Substrates, and Reagents

*Ginkgo biloba* "white nut" seeds were purchased from Dynasty Supermarket (Houston, Tex.). The seeds were stored at 4° C. for several days before sowing. Embryos were cultivated under aseptic conditions in an agar medium supplemented with D-glucose, L-glutamine, and Heller's salts at room temperature in the dark for four to six weeks (Schwarz, 1994). Synthesis of geranylgeranyl was performed as indicated in Ruan (1999) and Coates et al. (1978). Synthesis of geranylgeranyl diphosphate was performed as indicated by Corey et al. (1972), Davisson et al. (1985), and Davisson et al. (1986). Levopimarol was synthesized from levopimaric acid (Helix Biotech; New Westminster, British Columbia, Canada) according to procedures of Abad et al. (1985), Gigante et al. (1999), and Ayer and Talamas (1988). (6E,10E)-Geranyllinalool and pyridinium dichlorochromate were obtained from Fluka. All other reagents were obtained from either Sigma/Aldrich or Fisher Scientific, unless otherwise noted. Dichloromethane, dimethylformamide, methansulfonyl chloride, triethylamine, and toluene were freshly distilled over calcium hydride; tetrahydrofuran was freshly distilled over Na/benzophenone. Ammonium molybdate, ascorbic acid, tetrabutylammonium hydroxide, and citric acid were from ACROS. HP 20 polyaromatic dianion resin (250–850 $\mu$m) was purchased from Supelco.

Example 2

Methods—*G. Biloba* mRNA Isolation, cDNA Library Construction, and Quality Assessment At active growth, embryonic roots were harvested at 33 days (HSG1) and 40 days (HSG2) and snap-frozen in liquid nitrogen. Total RNA was isolated using a modified protocol for total RNA isolation from pine trees (Chang et al., 1993) in which an acidic phenol/chloroform (1:1) extraction was included prior to ethanol precipitation. Poly(A)+ RNA was selected with oligo(dT)cellulose (Life Technologies MessageMaker Poly(A)+ Syringe Kit) and purified using Sephadex gel chromatography (Boehringer Mannheim Mini Quick Spin RNA Column) according to manufacturer's instructions. cDNA libraries were prepared using the SuperScript™ Plasmid System for cDNA Synthesis and Plasmid Cloning (Life Technologies). cDNA constructs (SalI/Not I) were subcloned into both the *E. coli* expression vector pSPORT1 and the centromeric yeast shuttle vector pRS316GAL (Liu and Krizek, 1992). The resultant plasmids were transformed by electroporation into ElectroMax™ DH10B Cells (Life Technologies). The number of transformants in each library varied from $4.8 \times 10^5$ to $3.2 \times 10^6$ with approximate insert size ranging from 200 to 2600 bp.

Complementation experiments were conducted to determine the quality of the libraries. *G. biloba* cDNA library HSG2 (10 $\mu$g) in pRS316GAL was transformed into the auxotrophic *S. cerevisiae* strain JBY575 (MATa ura3-52-trpl-$\Delta$63 leu2-3,112 his3-$\Delta$200 ade2 Gal$^+$) (Corey et al., 1996) using the lithium acetate method (Ito et al., 1983), plated onto synthetic complete medium lacking uracil and supplemented with 2% glucose and 1.5% agar, and grown at 30° C. A total of $1.6 \times 10^5$ colonies were screened. Prototrophic clones were selected for growth by replica plating onto synthetic complete medium lacking leucine, tryptophan, or histidine and supplemented with 2% galactose and 1.5% agar, and incubated at 30° C. The frequency of complementing cDNA was 1 in every 17,778 to 40,000 for LEU2, 1 in every 20,000 to 32,000 for TRP1, and 1 in every 22,800 to 32,000 for HIS3.

Example 3

Methods—Levopimaradiene Synthase Gene Cloning

PCR degenerate primers were designed according to sequence similarity between gymnosperm terpene synthases

*Abies grandis* abietadiene synthase (SEQ.ID.NO:3), *Abies grandis* E-α-bisabolene synthase (GenBank Accession No. AF006195; SEQ.ID.NO:13 or GenBank Accession No. AF006194; SEQ.ID.NO:14; corresponding to the amino acid sequence in GenBank Accession No. AAC24192.1; SEQ.ID.NO:15 or AAC24191.1; SEQ.ID.NO:16, respectively), *Abies grandis* δ-selinene synthase (GenBank Accession No. U92266; SEQ.ID.NO:17; corresponding to the amino acid sequence in GenBank Accession No. AAC05727. 1; SEQ.ID.NO:18); *Abies grandis* γ-humulene synthase (GenBank Accession No. U92267; SEQ.ID.NO:19; corresponding to the amino acid sequence in GenBank Accession No. AAC05728. 1; SEQ.ID.NO:20), *Abies grandis* pinene synthase (GenBank Accession No. U87909; SEQ.ID.NO:21; corresponding to the amino acid sequence in GenBank Accession No. AAB71085.1; SEQ.ID.NO:22); *Abies grandis* (−)-4S-limonene synthase (GenBank Accession No. AF006193; SEQ.ID.NO:23; corresponding to the amino acid sequence in GenBank Accession No. AAB70907.1; SEQ.ID.NO:24); *Abies grandis* myrcene synthase (GenBank Accession No. U87908; SEQ.ID.NO:25; corresponding to the amino acid sequence in GenBank Accession No. AAB71084.1; SEQ.ID.NO:26); *Abies grandis* (−)-limonene/(−)-alpha-pinene synthase (agc11) (GenBank Accession No. AF139207; SEQ.ID.NO:27; corresponding to the amino acid sequence in GenBank Accession No. AAF61455.1; SEQ.ID.NO:28); and *Taxus brevifolia* taxadiene synthase (SEQ.ID.NO:41).

PCR reactions were conducted on 50 μL scale containing 200 ng cDNA, 5.0 μL 10×PC2 buffer (500 mM Tris-HCl, pH=9.1, 160 mM (NH4)2SO4, 35 mM MgCl$_2$), 4.0 μL 2.5 mM dNTPs, and 5.0 μL (20 pmol/μL) forward and reverse degenerate primers. The program employed a 4 min 95° C. hot-start after which 0.5 μL Taq DNA Polymerase (5.0 Units/μL, Fisher Biotech) was added to the PCR reaction, followed by 40 cycles with 1 min annealing using a temperature gradient from 68° C. to 48° C. (−0.5° C./cycle), 3 min extension at 72° C., and 45 second denaturation at 95° C. The program was terminated with a 5 min extension at 72° C. An aliquot of each reaction (5 μL) was analyzed on 2% agarose gel. The first round of PCR reactions employed the degenerate forward primer HSG1FP (5'-GCNTAYGAYACNGCNTGGGT-3'; SEQ.ID.NO:29). Combination with HSG6RP (5'-GCYTKRTANGTYTTNGTRTC-3'; SEQ.ID.NO:30) resulted in a 1907 bp fragment (HSG97), which was re-amplified, gel purified (QIAGEN), quantitated, and ligated into pGEM-T vector (50 ng/μL, Promega).

Conventional abbreviations are used in the primer sequences, wherein N is any base, K is G or T, Y is a pyrimidine, and R is a purine. The remainder of the sequence was obtained with specific primers HSG97.3FP (5'-ATGTGGTGGACTGGCAAGAG-3'; SEQ.ID.NO:5) and HSG97.3RP (5'-TAAAGATCGTCCAGAATAAC-3'; SEQ.ID.NO:6). A 1372 bp segment was excised with DraI and BsrG I. The DNA fragment (25 ng) was radiolabeled with α-$^{32}$P-dCTP using random oligonucleotide primers to probe 3.0×10$^5$ colonies (cDNA library HSG2E) by colony hybridization (Ausubel et al., 1999).

A total of 10 colonies were obtained, for which an additional round of screening yielded 47 hybridizing colonies. Six colonies were investigated further and restriction enzyme mapping indicated that three clones corresponded to the size of the expected full-length cDNA. Sequence analysis with forward primer T7 and reverse primer SP6 indicated that these genes were putative diterpene cyclases based on homology to *Abies grandis* abietadiene synthase. All three clones exhibited identical 5' and 3' ends, therefore, one was selected for gene characterization.

Primers HSG100.1FP (5'-AACTGCCAGATGGCTCGTGG-3'; SEQ.ID.NO:7) and HSG100.2FP (5'-GGTGGAGTATGCTATAAAGT-3'; SEQ.ID.NO:8) were used along with HSG97.3FP to obtain the remaining sequence. Sequence data revealed that a 2681 bp cDNA (HSG100/pSPORT1) had been cloned, however, the initiation codon was absent. RNA ligase mediated rapid amplification of cDNA ends (FirstChoice™ RLM-RACE Kit, Ambion) was employed with outer gene specific primer HSG150OGS (5'-CAGAGCCGTCAATTGACGGAATTC-3'; SEQ.ID.NO:9) and inner gene specific primer HSG150IGS (5'-CATCGACGCTTGATTTCGATGTCG-3'; SEQ.ID.NO:10) to obtain the N-terminal sequence. The full-length clone (2705 bp) encoded an 873 amino acid open reading frame of 2622 bp with a predicted molecular weight of 100,289. Sequence alignment using the Clustal method indicated a 60% identity to *Abies grandis* abietadiene synthase, 46% to *Abies grandis* bisabolene synthase, and 41% to *Taxus brevifolia* taxadiene synthase (FIG. 4).

Figure 4:
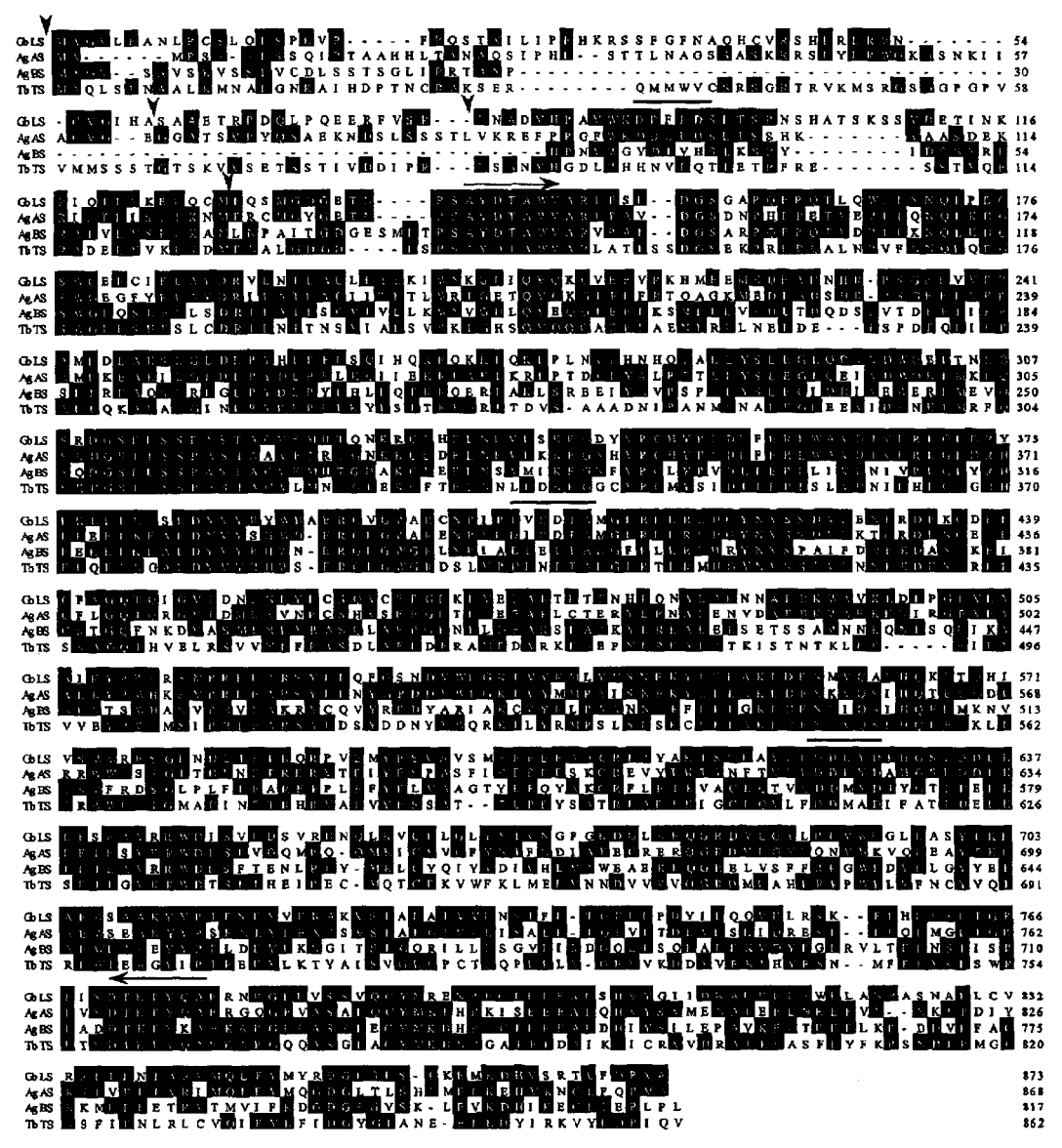

Sequence alignment in FIG. 4 was prepared with MegAlign (DNAStar, Madison, Wis.) using the Clustal method. Amino acid residues identical in at least three of the four synthases are shaded; hyphens indicate gaps inserted to maximize sequence alignment. Lines indicate aspartate-rich motifs, arrows designate regions targeted by degenerate PCR primers, and arrowheads identify N-terminal cleavage sites.

GbLS is *Ginkgo biloba* levopimaradiene synthase; AgAs is *Abies grandis* abietadiene synthase; AgBS is *Abies grandis* bioabolene synthase; and TbTS is *Taxus brevifolia* taxadiene synthase.

Example 4
Methods—cDNA Expression and Enzymatic Assay

Site-directed mutagenesis of HSG100/pSPORT1 with primers Ala$^2$ (5'-TTGCAAAGAGCACCCCAGCCATTTT-TTTTGTCGACACCCGGGAATTCCGGACCGGT-3'; SEQ.ID.NO:11), Ser$^{61}$ (5'-TGGACGAGTCTCTGCAGC-TGACATTTTTTTTGTCGACCAATTCCATCTCAGC-CTT-3'; SEQ.ID.NO:12), Leu$^{80}$ (5'-TGATAATCCGCAT-TAAGCATTTTTTTTGTCGACTCCTCCTGTGGAAG-CTGAT-3'; SEQ.ID.NO:31), and Phe$^{129}$ (5'-TCGCCCA-TGGACTGAAACATTTTTTTTGTCGACTTCACCAA-TGTCTGGATTCT-3'; SEQ.ID.NO:40) was employed to incorporate a SalI restriction site and a methionine initiation codon immediately upstream of Ala$^2$, Ser$^{61}$, Leu$^{80}$, and Phe$^{129}$. The plastid targeting sequence (e.g., N-terminal sequence) was removed by sequential digest with SalI followed by NotI.

In specific embodiments, the Ala$^2$ mutant amino acid sequence (SEQ.ID.NO:33) is encoded by the nucleic acid sequence SEQ.ID.NO:32; the Ser$^{61}$ mutant amino acid sequence (SEQ.ID.NO:35) is encoded by the nucleic acid sequence of SEQ.ID.NO:34; the Leu$^{80}$ mutant amino acid sequence (SEQ.ID.NO:37) is encoded by the nucleic acid sequence of SEQ.ID.NO:36; and the Phe$^{129}$ mutant amino acid sequence (SEQ.ID.NO:39) is encoded by the nucleic acid sequence of SEQ.ID.NO:38. In a specific embodiment, an N-terminal truncation at any point in the amino acid sequence up to and including amino acid 129. In specific embodiments, alternative truncations are generated at the following sites: Cys$^{55}$, Glu$^{74}$, Glu$^{76}$, or Val$^{88}$, wherein the truncation site occurs just prior to the indicated amino acid (for example, between Asn$^{54}$ and Cys$^{55}$). A skilled artisan is aware that sequences having N-terminal truncations preferably have an ATG start codon included.

A. Expression in a Prokaryote

The desired plasmids were prepared by ligating the mutated gene insert into the similarly digested vectors pET32c(+) (Novagen; Madison, Wis.) and pRS426GAL (Hua, 2000), a multiple copy yeast expression vector. These plasmids was expressed in *E. coli* BL21(DE3) (Novagen; Madison, Wis.). *E. coli* cells were grown in Luria-Bertani medium supplemented with 100 µg/mL ampicillin at 37° C. with shaking to $OD_{600}$ ~0.6. The following parameters were tested: isopropyl 1-thio-β-D-galactopyranoside (IPTG) concentration (50, 100, 250, 500, and 1000 µM); and temperature and time (20° C. for 2, 3, 4, 6, 21 hours, 22° C. for 6, 8, 16, 19, 22, 45 hours, and 30° C. for 3, 6 hours). The following assay conditions were tested to obtain maximum diterpene product yield: 30 mM HEPES (N-2-hydroxyethylpiperazine-N'-4-butanesulfonic acid), pH 6.9, 7.2, 7.6, 8.0; 30 mM Tris(tris(hydroxymethyl)aminomethane hydrochloride), pH 7.4, 7.8, 8.2; 1, 5, 10% glycerol; 1, 3, 5, 10, 20 mM DTT (dithiothreitol); 20 mM β-mercaptoethanol; 2, 5, 8% Triton X-100; 5% Tween 80; 0, 2, 7.5, 20, 50 mM $MgCl_2$; 0, 30, 500, 1000 µM $MnCl_2$; 2, 10, 13.3, 20, 40, 80, 200 µM GGDP; and 23° C. and 32° C. assay temperatures.

Optimal soluble protein production and diterpene yield were obtained with the following conditions. Cell cultures were induced with 1 mM IPTG at 20° C. with shaking for 6 hours and lysed by sonication in 30 mM HEPES, pH 7.2, 5 mM DTT, and 5% glycerol. The soluble fraction of the lysate (100 mg/mL) was incubated with 20 µM GGDP in 30 mM HEPES, pH 7.2, 5 mM DTT, 5% glycerol, 2 MM $MgCl_2$, and 500 µM $MnCl_2$ overnight at 32° C.

Levopimaradiene synthase was also tested for activity towards 200 µM geranyl diphosphate and farnesyl diphosphate. Cell cultures were induced and lysed as noted above. The soluble fraction of the lysate was incubated overnight at 32° C. with 200 µM substrate in 30 mM HEPES, pH 7.2, 5 mM DTT, 5% glycerol, 2 mM $MgCl_2$ and 500 µM $MnCl_2$, and overlaid with hexane (1 mL).

B. Expression in a Eukaryote

Expression in *S. cerevisiae* JBY575, which represents wild-type yeast, was observed. JBY575 cells transformed with pRS426GAL inserted with the putative levopimaradiene synthase were grown in synthetic complete medium lacking uracil and supplemented with 2% glucose and 1.5% agar at 30° C. to saturation and induced with galactose for 48 hours. Cells were harvested, resuspended in lysis buffer, and mixed by vortexing over glass beads. The lysate was assayed with 60 µM GGDP in the presence and absence of 0.2% and 5% Triton X-100.

All in vitro reactions were extracted 3× with hexane and dried over $MgSO_4$. The reaction was further extracted twice with diethyl ether and dried over $MgSO_4$. Thereafter, the crude lysate was suspended in 100 mM Tris, pH 8.0 containing 2.9 units/mg apyrase (a dephosphorylating agent) and 10 units/µL calf intestinal alkaline phosphatase, incubated at 30° C. for 3 hours, and extracted with diethyl ether as noted above (Croteau and Cane, 1985). The crude reaction mixtures were eluted over $SiO_2$, concentrated, and analyzed by GC and GC/MS.

Gas chromatography spectra were obtained on a Hewlett Packard 6890 Series GC System equipped with an $Rt_x$-5 capillary column (Restek, 30 m×0.25 mm i.d., 0.10 µm $d_f$). The following separation conditions and temperature program were employed: injector port 250° C., FID 250° C., split ratio 39:1, helium flow 20 cm/s (0.6 mL/min), 150° C. hold 5 min, increase to 250° C. (5° C./min), hold 5 min. GC/MS spectra were obtained on a Hewlett-Packard 5890A instrument with a 30-m DB-5ms column (J&W Scientific Inc., 0.25 mm i.d., 0.10 µm df). The following separation conditions and temperature program were employed: injector port 280° C., transfer lines: 280° C., helium flow at 30 cm/s (1 mL/min) with splitless injection at 150° C. hold 3 min, increase to 250° C. (5° C./ min), hold 5 min. Mass spectra (m/z 50 to 500) were obtained on a VG ZAB-HF reverse-geometry double-focusing instrument at 70 eV with an electron-impact ion source (200° C.). Accelerating voltage was set to 8 kV and the resolution was 1000 (10% valley).

Example 5

Levopimaradiene Standard-Synthesis and Structural Confirmation

Levopimarol (95.0 mg, 0.33 mmol) was dissolved in 3.7 mL dichloromethane and 92 µL triethylamine then cooled to 0° C. Methanesulfonyl chloride (31 µL, 0.39 mmol) was added dropwise via syringe. The reaction was monitored by thin layer chromatography (TLC) (1:1 chloroform:diethyl ether) and quenched after 15 min with ice-cold saturated aqueous sodium bicarbonate. The solution was extracted with dichloromethane (3×), washed with $H_2O$, dried with $MgSO_4$, filtered, and concentrated. (Cambie et al., 1990) The crude material was purified by preparative TLC (1 mm $SiO_2$, 1:1 chloroform:diethyl ether) yielding 75.1 mg levo-8,12-dien-18-yl methanesulfonate (62.4% yield, $R_f$ 0.96). 1H NMR ($CDCl_3$, 400 MHz) δ5.54 (q, J=1.8 Hz, 1H, H-14), 5.15 (t, J=4.3 Hz, 1H, H-12), 3.97 (d, J=9.4 Hz, 1H, H-18), 3.73 (d, J=9.4 Hz, 1H, H-18), 3.00 (s, 3H, $CH_3SO_2$), 2.38–2.28 (m, 3H, H-7α, H-11α, H-11β), 2.19–2.03 (m, 3H), 1.76 (dt, 1H), 1.61–1.52 (m, 3H), 1.47–1.34 (m, 4H), 1.27–1.21 (m, 1H), 0.97 (d, 6H, H-16, H-17), 0.91 (s, 3H), 0.88 (s, 3H).

Under an inert atmosphere, the mesylate (21.5 mg, 0.06 mmol) was dissolved in tetrahydrofuran in a Schlenk flask equipped with a cold finger. Excess lithium triethylborohydride (263 µL, 1 M in tetrahydrofuran, 0.26 mmol) was added dropwise to the solution, the reaction was stirred at reflux for 6 hours and monitored by TLC (6:1 hexane:diethyl ether). The reaction was quenched with ice-cold H2O, extracted with hexane (3×), dried with $MgSO_4$, filtered over a silica plug, and concentrated. (Walter, 1988) GC analysis indicated that an 85:15 mixture of levopimaradiene:abietatriene had been obtained in 41.3% yield (6.6 mg). The isomeric mixture was separated by argentic TLC (Li et al., 1995) ($SiO_2$—$AgNO_3$, 3 developments with 85:15 hexane:diethyl ether) giving pure abietatriene ($R_f$ 0.96) (Kutney and Han, 1996) and pure levopimaradiene ($R_f$ 0.92) as identified by de novo characterization based on $^1H$, COSY-DEC, $^{13}C$, DEPT-135, HSQC, and HMBC NMR, and GC/MS analyses.

$^1H$ NMR ($CDCl_3$, 500 MHz, 25° C.) δ5.518 (q, J=1.8 Hz, 1H, H-14), 5.141 (br tq, J=4.3, 1.3 Hz, 1H, H-12), 2.338 (ddd, J=13.3, 4.5, 2.2 Hz, 1H, H-7β), 2.323, 2.307 (m, 2H, H-11α, H-11β), 2.145 (septet of q, J=6.8, 1.3 Hz, 1H, H-15), 2.075 (br td, J=13.2, 5.2 Hz, 1H, H-7α), 2.021 (ddt, J=11.5, 8.6, 1.8 Hz, 1H, H-9α), 1.737 (dtd, J=12.9, 3.4, 1.6 Hz, 1H, H-1β), 1.697 (ddt, J=12.7, 5.4, 2.7 Hz, 1H, H-6α), 1.519 (dt, J=13.5, 3.4 Hz, 1H, H-2α), 1.444 (m, 1H, H-2β), 1.386 (m, 1H, H-3β), 1.368 (qd, J=12.8, 4.5 Hz, 1H, H-6β), 1.149 (tdd, J=13.2, ~4.0, 0.8 Hz, 1H, H-3α), 1.045 (dd, J=12.5, 2.8 Hz, 1H, H-5α), 0.975 (d, J=6.8 Hz, 6H, H-16, H-17), 0.866 (td, J=~12.7, ~3.4 Hz, 1H, H-1α), 0.862 (s, 3H, H-18), 0.861 (s, 3H, H-20), 0.821 (s, 3H, H-19). Chemical shifts were referenced to $Si(CH_3)_4$ and are accurate to ±0.001. Coupling constants are accurate to ±0.5 Hz.

$^{13}$C NMR (CDCl$_3$, 125 MHz, 25° C.) δ139.46 (C-8), 138.91 (C-13), 118.73 (C-14), 114.87 (C-12), 55.23 (C-5), 49.61 (C-9), 42.21 (C-3), 40.75 (C-10), 37.91 (C-1), 36.15 (C-7), 33.48 (C-20), 33.45 (C-4), 33.26 (C-15), 23.80 (C-6), 22.75 (C-11), 21.80 (C-19), 21.45 (C-17), 21.37 (C-16), 19.00 (C-2), 14.10 (C-18). Chemical shift (±.02 ppm) were referenced to the CDCl$_3$ signal at 77.0 ppm.

GC/MS EI$^+$ m/z (%)=272 [M$^+$] (73), 257 [M—CH$_3$] (13), 229 [M—CH(CH$_3$)$_2$] (7), 148 [M—C$_9$H$_{16}$] (64), 147 (27), 146 (50), 137 [M—C$_{10}$H$_{15}$] (94), 136 (65), 135 (60), 134 (90), 133 (66), 131 (43), 119 (27), 117 (34), 105 (58), 95 (31), 93 (28), 92 (100), 91 [M—C$_{13}$H$_{25}$] (97), 83 (20), 81 (26), 69 (24). GC co-elution of synthetic levopimaradiene with the enzymatic product and GC/MS fragmentation confirmed the identity of the in vitro product diterpene as levopimaradiene.

Example 6

Isolation and Characterization of a Diterpene Cyclase cDNA from *Ginkgo Biloba*

*G. biloba* cDNA libraries were prepared from cultivated embryonic roots. A homology-based approach utilizing PCR was employed to screen the library. Degenerate primers were designed based on conserved sequence regions among gymnosperm terpene synthases. These included *Abies grandis* abietadiene synthase, a bifunctional diterpene synthase that directs both proton-initiated cyclization and ionization of the divalent metal cation-diphosphate ester moiety; and synthases that effect diphosphate ionization to induce cyclization, including the diterpene *Taxus brevifolia* taxadiene synthase; the sesquiterpenes *Abies grandis* bisabolene synthase, selinene synthase, and humulene synthase; and the monoterpenes *Abies grandis* pinene synthase, limonene synthase, and myrcene synthase. Seven forward and eight reverse degenerate primers identifying eight regions of high sequence homology were designed. The combination of HSG1FP with HSG6RP resulted in amplification of a 1907 bp fragment (HSG97), which was determined to have significant sequence homology to higher plant terpene cyclases. A segment of this fragment was $^{32}$P-labeled and used as a hybridization probe for high stringency screening of 3.0×10$^5$ colonies from cDNA library HSG2. A skilled artisan is aware that the cDNA preferably comprises a majority of expressed sequences, which are also preferably full-length, from an organism.

A total of 10 hybridizing colonies were obtained and put through a secondary round of high stringency screening producing an enriched pool of clones. The termini of the three longest cDNAs were sequenced and identified as putative diterpene cyclases based on homology to *Abies grandis* abietadiene synthase. Furthermore, all three clones had identical 5' and 3' ends (approximately 600 bp at each end). One clone was further characterized. Sequence data revealed that a 2681 bp cDNA had been cloned, however, the initiation codon was absent. RNA ligase mediated rapid amplification of cDNA ends ("RACE") was employed to isolate the 5'-untranslated region and the methionine start site. The full-length gene, *Ginkgo biloba* levopimaradiene synthase, a diterpene synthase, was 2705 bp in length and encoded an 873 amino acid open reading frame of 2622 bp with a predicted molecular weight of 100,289 (see FIG. 4).

Example 7

Analysis and Selection of Plastid Targeting Sequence Cleavage Site

Cytosolically synthesized plastid proteins contain N-terminal targeting sequences that direct their translocation to specific plastidial compartments. Proteolysis of the signal sequence occurs by a specific protease, yielding the mature protein. Plastid transit peptides typically range between 30 to 80 amino acids in length; are rich in hydroxlated amino acids, basic amino acids, and small hydrophobic residues; and display low contents of tyrosine and acidic residues. For purposes of heterologous expression, wherein native processing peptidases are not present, cleavage of the signal sequence may be required prior to expression to avoid formation of inclusion bodies. In general, cleavage sites are distinguished by a decreased frequency of serine residues and a corresponding increase in the frequency of tyrosine and acidic amino acids. In a majority of higher eukaryotes, arginine is found at positions −2 and −6 to −10 relative to the cleavage site. Furthermore, a consensus motif of (Val/Ile)-X-(Ala/Cys)↓Ala (wherein the downward arrow (↓) indicates the site of bond cleavage) has been identified in a series of stroma-targeting chloroplast transit peptides with known cleavage sites (von Heijne and Nishikawa, 1991; von Heijne and Gavel, 1990; Keegstra and Olsen, 1989).

Analysis of *Ginkgo biloba* levopimaradiene synthase indicated the following representation of amino acid residues: the first tyrosine residue at Y$^{84}$; the first glutamic acid residue at E$^{64}$; the first aspartic acid residue at D68; and a decreased frequency of serine residues between S$^{47}$ and S$^{96}$. Two potential cleavage sites were identified at Ile-His-Ala$^{60}$↓Ser$^{61}$ (with arginine at −9 and −11 relative to the cleavage site) and at Ile-Gln-Cys$^{127}$↓Met$^{128}$ (with arginine at −11 relative to the cleavage site). Submission of *Ginkgo biloba* levopimaradiene synthase to META Predict Protein Chloro P predicted the presence of an N-terminal chloroplast transit peptide with a cleavage site between H$^{59}$-A$^{60}$ (Nielsen et al., 1995). Three truncation sites were selected in consideration of the data presented above: Ala$^{60}$-Ser$^{61}$ (hereafter referred to as Ser$^{61}$), Arg $^{79}$-Leu$^{80}$ (hereafter referred to as Leu$^{80}$), and Cys$^{127}$-Met$^{128}$ (hereafter referred to as Phe$^{129}$).

Recently, successful heterologous expression of truncated levopimaradiene synthases have been reported. Cleavage of the N-terminal 84 residues of *Abies grandis* abietadiene synthase produced active protein (Ravn et al., 2000). Truncation of 79 or fewer residues of *Taxus brevifolia* taxadiene synthase produced functional protein, however, elimination of 93 or more residues resulted in loss of catalytic activity (Williams et al., 2000). Low primary sequence homology is observed between *Ginkgo biloba* levopimaradiene synthase, *Abies grandis* abietadiene synthase, and *Taxus brevifolia* taxadiene synthase prior to residue *Ginkgo biloba* levopimaradiene synthase Trp$^{89}$, 21.5% and 14.0%, respectively. However, significant sequence similarity begins at position Trp$^{89}$, 65.7% and 44.1% respectively. Furthermore, no distinct identity is apparent between these synthases at the truncation sites reported to produce functional protein.

Example 8

Levopimaradiene Synthase Sequence Analysis

Protein analysis of the deduced polypeptide indicated *Ginkgo biloba* levopimaradiene synthase to have high sequence similarity to *Abies grandis* abietadiene synthase (60%), *Abies grandis* bisabolene synthase (46%), and *Taxus brevifolia* taxadiene synthase (41%). Three aspartate-rich motifs and a putative plastidial transit peptide were identified in *Ginkgo biloba* levopimaradiene synthase. An N-terminal DDXID motif (*Ginkgo biloba* levopimaradiene synthase 91–95), also observed in *Abies grandis* abietadiene synthase, may serve to stabilize carbocations and/or direct deprotonation. Crystallographic and mutagenesis studies suggest that the consensus motif, D(I/V)DDTA (*Ginkgo biloba* levopimaradiene synthase 405–410), initiates cyclization of GGDP. Moreover, this aspartate-rich sequence remains highly conserved among synthases that effect proton-initiated cyclization, including copalyl diphosphate synthases, *Abies grandis* abietadiene synthase, *Phaeosphaeria* ent-kaurene synthase, and squalene-hopene cyclases (Bohlman et al, 1998). A carboxy-terminal DDXXD motif (*Ginkgo biloba* levopimaradiene synthase 624–628) resides in kaurene synthases; *Abies grandis* abietadiene synthase; prenyltransferases; and in plant mono-, sesqui-, and diterpene synthases (Bohlman et al., 1998). This domain in a specific embodiment affects binding of the divalent metal ion-diphosphate complex. Crystal structure analysis of tobacco epi-aristolochene synthase identified two $Mg^{2+}$ ions bound at the entrance of the active site by coordination to aspartic acid residues of the DDXXD motif (Starks et al., 1997).

Comparative protein analysis indicated that *Ginkgo biloba* levopimaradiene synthase contained features reminiscent of two distinct catalytic domains, and thereby confirmed it as a bifunctional levopimaradiene synthase. Furthermore, *Ginkgo biloba* levopimaradiene synthase displayed a high degree of homology to conserved amino acid residues of mono-, sesqui-, and diterpene secondary metabolite families (Bohlman et al., 1997). These included the absolutely or highly conserved residues $Ser^{459}$, $Ala^{472}$, $Pro^{713}$, $Cys^{789}$, $Arg^{414, 417, 587, 610, 766}$; the acidic residues $Asp^{363, 624, 625, 628, 770, 851}$ and $Glu^{466, 567, 592, 703, 717}$; and the aromatic residues $His^{419}$, $Phe^{431, 438, 585, 663}$, $Tyr^{523, 594, 700, 847}$, and $Trp^{89, 574, 646, 706}$. Three significant deviations in the *Ginkgo biloba* levopimaradiene synthase sequence included a highly conserved histidine which corresponds to *Ginkgo biloba* levopimaradiene synthase $Tyr^{373}$, an absolutely conserved proline which corresponds to *Ginkgo biloba* levopimaradiene synthase $Arg^{655}$, and an absolutely conserved acidic amino acid which corresponds to *Ginkgo biloba* levopimaradiene synthase $Gly^{672}$.

Example 9

Protein Expression and Optimization of In Vitro Enzymatic Activity

Site-directed mutagenesis was employed to insert a SalI site followed by seven adenines and a methionine start codon at $Ala^2$, $Ser^{61}$, $Leu^{80}$, and $Phe^{129}$. Following removal of the 5'-untranslated region and plastid targeting sequence, the desired plasmids were prepared by ligation with pET32c (+) (a bacterial expression system containing a thioredoxin tag designed for maximal production of soluble protein) and pRS426GAL (a multiple copy yeast expression system). The levopimaradiene synthase was expressed in the *E. coli* strain BL21(DE3) and the wild-type *S. cerevisiae* strain JBY575, respectively. *E. coli* cells were grown in Luria-Bertani medium supplemented with ampicillin and induced with IPTG. SDS-PAGE analysis indicated that protein production increased with time and reached maximum accumulation by 21 hours. However, recombinant protein resided mainly in the insoluble fractions of the lysate, indicating that it was likely encapsulated in an inclusion body. Attempts to improve protein solubility by variation of IPTG concentrations between 50 to 1000 mM were unsuccessful. However, employing an induction temperature of 20° C. produced functionally soluble protein.

The skilled artisan recognizes that lysis and assay conditions should be optimized. Examples of parameters that can be adjusted to optimize conditions include altering buffer, pH, reductant, reductant concentration, metal cofactors, cofactor concentrations, glycerol concentrations, substrate concentrations, and assay temperatures. Levopimaradiene synthase activity proved to be independent of magnesium but required manganese cofactor for catalysis. Maximum soluble protein production and diterpene yield were obtained with the following conditions. Cell cultures were induced with 1 mM IPTG at 20° C. with shaking for 6 hours and lysed by sonication in 30 mM HEPES, pH 7.2, 5 mM DTT, and 5% glycerol. The soluble fraction of the lysate (100 mg/1 mL) was incubated with 20 μM GGDP in 30 mM HEPES, pH 7.2, 5 mM DTT, 5% glycerol, 2 mM $MgCl_2$, and 500 μM $MnCl_2$ overnight at 32° C. Yeast expression was induced with galactose at 30° C. for 48 hours and the cells were lysed and assayed according to the conditions noted.

The extent of N-terminal truncation affected catalytic activity in both expression hosts. Bacterial expression of *Ginkgo biloba* levopimaradiene synthase truncated at $Ala^2$, $Ser^{61}$, and $Leu^{80}$ produced levopimaradiene as the exclusive diterpene hydrocarbon, however, $Phe^{129}$ failed to produce detectable levels of any diterpene. Highest expression levels were obtained with the $Ser^{61}$ truncation (approximately 1% turnover of GGDP) and lowest levels were obtained with $Ala^2$, with approximately 80% difference in activity. Yeast expression of $Ser^{61}$ and $Leu^{80}$ yielded levopimaradiene as the sole diterpene. However, both the $Ala^2$ and $Phe^{129}$ truncated genes failed to produce observable levels of any diterpene product. Controls performed in parallel did not yield levopimaradiene. *E. coli* expression and incubation with geranyl diphosphate and farnesyl diphosphate did not produce any identifiable terpenes by GC or GC/MS. However, a skilled artisan is aware of parameters which may be optimized and/or additional sequences which may be employed to detect and/or increase synthesis of levopimaradiene synthase.

Example 10

Product Characterization

Due to the low levels of levopimaradiene production, a synthetic standard to confirm product identification was utilized. Levopimaric acid was obtained from Helix Biotech and converted to levopimarol according to literature procedures, with care employed to minimize exposure to oxygen and heat. Reaction of the alcohol with mesyl chloride and triethylamine followed by silica gel purification resulted in a 62% yield of the mesylate derivative. The ester was reduced with Super-Hydride® to yield a 41% mixture of levopimaradiene:abietatriene (85:15). Argentic chromatography effected the separation of the hydrocarbons; levopimaradiene was identified by NMR and GC/MS analysis. Co-elution on GC and identical GC/MS fragmentation of the biosynthetic hydrocarbon with the synthetically prepared levopimaradiene confirmed identification of the enzyme product to be levopimaradiene.

Molecular biology techniques were employed to confirm the presence of levopimaradiene as a rapidly metabolized intermediate. The bifunctional enzyme directs a multi-step mechanistic sequence in which GGDP is cyclized to labdadienyl diphosphate which undergoes allylic ionization of the ester moiety followed by hydrogen shift, methyl migration, and deprotonation yielding levopimaradiene.

Example 11

Expression In Vivo in Yeast that Accumulate GGDP

A skilled artisan recognizes that it is preferable to increase the amount of substrate provided for in the production of levopimaradiene to ultimately increase ginkgolide yields. Thus, the invention preferably includes an increase in the amount of effective geranylgeranyl diphosphate, which is upstream in the ginkgolide biosynthetic pathway. A skilled artisan recognizes that an effective amount of geranylgeranyl diphosphate is that which is subject to metabolism in the isoprene biosynthetic pathway. A skilled artisan is aware that an increase in GGDP occurs in multiple ways, such as by providing GGDP exogenously or by increasing its production through transgenic and/or bioengineering means. GGDP is increased by the methods and compositions of the invention described in the U.S. Patent Application entitled, "Diterpene-Producing Unicellular Organism" filed on the same day and incorporated by reference herein.

The yeast strain of the copending application employed was EHY18 (Hart, E., 2001) which was further transformed with multiple-copy yeast expression vectors comprising an isolated and purified nucleic acid sequence of GbLS or derivatives thereof, which are described herein under control of the GAL1 inducible promoter. Yeast cells were grown to saturation in 5 mL ScD-Leu-Ura at 30° C. Cells were harvested (1300×g, 2 min, 25° C.) and resuspended in 500 $\mu$L sterile Milli-Q $H_2O$ (2×). The washed cells were resuspended in 5 mL sterile Milli-Q $H_2O$. An aliquot of the culture (5 $\mu$L) was added to a 25 mL Corex tube containing pre-prepared 2×resin and 5 mL ScG-Leu-Ura (4% galactose) and shaken at 30° C. for 6 days. Resin was collected by filtration through a Kontes chromatography column (1.7 cm diameter) and rinsed with dI $H_2O$ until eluent was clear. The resin was incubated in 2 mL ethanol for several minutes, eluted, and repeated 2×. The combined eluents were dissolved in approximately 3 mL dI $H_2O$ and extracted (3×) with 3 mL hexane. The combined extracts were concentrated under a stream of nitrogen. GC analysis (quantitation extrapolated from 0.2 mg/mL longifolene external standard) indicated the following product profile (obtained from triplicate measurement of three cultures): 0.61±0.20 mg/L levopimaradiene, 0.04±0.01 mg/L abietadiene, 0.15±0.05 mg/L abietatriene, 0.16±0.13 mg/L (+)-copalol, and 1.79±0.90 mg/L geranylgeraniol. GC/MS fragmentation confirmed the identity of each compound.

A large scale culture (1-L) was prepared by growing the yeast cells to saturation in 5 mL ScD-Leu-Ura at 30° C. Cells were harvested (1300×g, 2 min, 25° C.) and resuspended in 500 $\mu$L sterile Milli-Q $H_2O$ (2×). The washed cells were resuspended in 5 mL sterile Milli-Q $H_2O$. An aliquot of the culture (1 mL) was added to a 2 L flask containing 1-L ScG-Leu-Ura (4% galactose) and 88.27 g resin in 120 mL Milli-Q $H_2O$ (pre-prepared). The resin was eluted with ethanol (3×100 mL with 20 min incubation periods), which was subsequently extracted (6×) with hexane. The combined extracts were dried over magnesium sulfate, filtered, and concentrated under reduced pressure. GC analysis (quantitation extrapolated from 0.2 mg/mL longifolene external standard) indicated the following product profile (obtained from triplicate measurement): 0.29±0.04 mg/L levopimaradiene, 0.04±0.02 mg/L abietadiene, 0.13±0.04 mg/L abietatriene, 0.11±0.02 mg/L (+)-copalol, and 0.56±0.03 mg/L geranylgeraniol. GC/MS analyses confirmed the production of the above noted diterpenes, which included hydrocarbons and an alcohol.

Example 12

Optimization of Levopimaradiene Production

Similar to levopimaradiene synthase activity in *E. coli*, catalytic activity in EHY18 was affected by the N-terminal truncation of GbLS. Expression of wild-type levopimaradiene synthase and its truncated counterparts Ser61 and Leu80 produced (+)-copalol, levopimaradiene, abietadiene, and abietatriene. Co-elution on GC and identical GC/MS fragmentation of the biosynthetic alcohol with synthetic (+)-copalol allowed the unequivocal identification of the enzyme product as (+)-copalol. GC analysis of the expressed GbLS Phe129 indicated no diterpene alcohol or hydrocarbon formation. Highest diterpene production was obtained with the Ser61 and Leu80 truncated constructs (Ser61≧Leu80) and was approximately four times greater than that observed for the wild-type synthase. Negative controls performed in parallel (expressing EHY18) did not yield levopimaradiene, abietadiene, abietatriene, or (+)-copalol.

Further optimization studies employed the Ser61 construct. Factors influencing diterpene production included induction period and concentration of galactose and resin in the inducing medium. Highest diterpene yields were observed with 4% galactose and 0.70 g resin/5 mL culture medium. Expression for 6 days, in the above noted induction medium, resulted in a net yield of ~0.8 mg/L diterpene hydrocarbons and ~0.2 mg/L (+)-copalol, as determined by GC quantitation.

Expression of GbLS in EHY18 resulted in a three- to six-fold increase in levopimaradiene yield relative to the bacterial expression system previously employed. In addition, expression of GbLS in EHY18 afforded abietatriene, the immediate hydrocarbon precursor of the ginkgolides. The ability to enhance levopimaradiene production in a yeast cell having an increased effective amount of geranylgeranyl diphosphate suggests the system is useful in the isolation of the first oxygenase involved in ginkgolide biosynthesis. Lastly, identification of (+)-copalol represents the first observation of the free intermediate of (+)-copalyl pyrophosphate by a bifunctional diterpene catalyst and supports previous data implicating (+)-copalyl pyrophosphate as a precursor to levopimaradiene (Peters et al., 2000; Schwarz and Arigoni, 1999).

Bacterial expression optimization includes standard manipulations known in the art to overcome problems such as low solubility and low expression levels. For instance, a skilled artisan is aware that different *E. coli* expression systems, including commercially available vectors and strains, are utilized to produce higher amounts of soluble protein. An example of a vector includes pSBET (Schenk et al., 1995), which is particularly useful for heterologous expression in *Escherichia coli* of plant genes that often have a significant number of arginine residues. The vector is particularly well-suited to *Escherichia coli* BL21 (DE3) (Sambrook et al., 1989). Also, many different *E. coli* strains are known in the art and may be used, such as LE392 cells, DH5α cells, or SURE™ (Stratagene; La Jolla, Calif.) cells.

Example 13

Cloning Ginkgolide Biosynthetic Genes

Difficulties in RNA extraction from recalcitrant gymnosperm tissue have been noted (Chang, et al., 1993; Lewinsohn, et al., 1994). High levels of polysaccharides in gymnosperm tissue and oxidation of polyphenols during extraction resulted in contaminated and/or degraded RNA. With respect to *G. biloba* tissue, studies indicate that mature ginkgo seeds are comprised of approximately 35% water-soluble polysaccharides (Arahira, et al., 1994). However, successful construction of a *Ginkgo biloba* cDNA library, as described herein, has overcome this problem.

In a specific embodiment, nucleic acid sequences encoding other enzymes in the ginkgolide biosynthesis pathway are obtained. In a specific embodiment, a cDNA library, such as for *E. coli* or *S. cerevisiae*, comprising *Ginkgo biloba* sequences are exposed to an *E. coli* or *S. cerevisiae* cell, respectively, wherein the cell also comprises the levopimaradiene synthase sequence, and the presence of a desired downstream product is assayed. In a specific embodiment, the GC and/or GC/MS profile of the product is known and its presence is determined. In a further specific example, the nucleic acid sequence for a dehydrogenase, which generates formation of abietatriene, is cloned by assaying pools of cells harboring levopimaradiene synthase and identifying by chromatography (i.e., GC or GC/MS) the pool in which abietatriene is produced. Once a pool is identified, this pool is broken down into its constituents which are assayed in smaller pools and/or individually to identify the cell containing the clone expressing the desired nucleic acid sequence.

In an embodiment of the present invention, a first ginkgolide biosynthetic gene downstream of levopimaradiene synthase is provided in a cell comprising the levopimaradiene synthase, wherein both the first downstream gene and the levopimaradiene synthase are expressed concomitantly. In a specific embodiment, the cell provides biosynthesis of a ginkgolide biosynthetic intermediate that is a first derivative of levopimaradiene, such as abietatriene. A further embodiment is the subsequent cloning of a second downstream ginkgolide biosynthetic gene, which allows biosynthesis of a different ginkgolide biosynthetic intermediate upon expression in a cell comprising the levopimaradiene synthase, the first downstream ginkgolide biosynthetic gene and the second ginkgolide biosynthetic gene; this cell demonstrates biosynthesis of a ginkgolide biosynthetic intermediate that is a second derivative of the first derivative (e.g., abietatriene) of levopimaradiene. Other such embodiments are contemplated in which levopimaradiene, produced by a cell that expresses the *Ginkgo biloba* levopimaradiene synthase and conservatively modified variants, serves as an intermediate in biosynthesis of a diterpenoid, and preferably a ginkgolide.

Example 14

SUMMARY OF THE PRESENT INVENTION

Levopimaradiene synthase, which directs the first committed step in ginkgolide biosynthesis, was cloned and functionally characterized as part of a program to isolate and express genes involved in the biosynthesis of the ginkgolides. A *Ginkgo biloba* cDNA library was prepared from embryonic roots and screened utilizing a homology-based approach employing degenerate primers with high sequence similarity to gymnosperm terpene synthases. Polymerase chain reaction amplification provided a 1907 bp fragment, which was employed to probe the library. Colony hybridization and rapid amplification of cDNA ends yielded a full-length clone with a 2622 bp open reading frame encoding a predicted protein sequence of 873 amino acids with an estimated molecular weight of 100,289. Protein analysis indicated that a bifunctional terpene cyclase had been isolated with high sequence identity to *Abies grandis* abietadiene synthase (60%), *Abies grandis* bisabolene synthase (46%), and *Taxus brevifolia* taxadiene synthase (41%). Additionally, the amino acid sequence contained a putative N-terminal plastidial transit peptide and three aspartate-rich regions.

Functional expression in *Escherichia coli* of the full-length cDNA and corresponding truncations at $Ser^{61}$ and $Leu^{80}$ provided enzymatic activity capable of cyclizing geranylgeranyl diphosphate to levopimaradiene, as confirmed by GC/MS analysis. Expression of the truncated $Phe^{129}$ gene product resulted in complete loss of enzymatic activity. Functional expression in wild-type *Saccharomyces cerevisiae* of the $Ser^{61}$ and $Leu^{80}$ truncations yielded levopimaradiene synthase activity, albeit in lower yields than with the bacterial system, whereas the full-length and $Phe^{129}$ clones failed to produce detectable levels of biosynthetic product. Isolation and characterization of levopimaradiene synthase represents the first confirmation of an enzyme involved in ginkgolide biosynthesis.

An engineered yeast strain has been employed to achieve increased levopimaradiene production levels. An approximate three-fold to six-fold increase in levopimaradiene yield was obtained relative to the previously employed bacterial and yeast expression systems. In addition, production of abietatriene, the direct hydrocarbon progenitor of the ginkgolides, was realized.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference herein.

PATENTS

U.S. Pat. No. 5,302,523, issued Apr. 12, 1994.
U.S. Pat. No. 5,322,783, issued Jun. 21, 1994.
U.S. Pat. No. 5,384,253, issued Jan. 24, 1995.
U.S. Pat. No. 5,464,765, issued Nov. 7, 1995.
U.S. Pat. No. 5,508,184, issued Apr. 16, 1996.
U.S. Pat. No. 5,538,877, issued Jul. 23, 1996.
U.S. Pat. No. 5,538,880, issued Jul. 23, 1996.
U.S. Pat. No. 5,550,318, issued Aug. 27, 1996.
U.S. Pat. No. 5,563,055, issued Oct. 8, 1996.
U.S. Pat. No. 5,591,616, issued Jan. 7, 1997.
U.S. Pat. No. 5,610,042, issued Mar. 11, 1997.
U.S. Pat. No. 5,840,873, issued Nov. 24, 1998
U.S. Pat. No. 5,843,640, issued Dec. 1, 1998
U.S. Pat. No. 5,843,650, issued Dec. 1. 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999

U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 199
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641
PCT Application WO 9217598
PCT Application WO 94/09699
PCT Application WO 95/06128
PCT Application WO 95/06128

NON-PATENTED LITERATURE

Abad, A., Arno, M., Domingo, L. R., and Zaragoza, R. J. (1985) Tetrahedron 41, 4937–4940.
Abdullah et al., Biotechnology, 4:1087, 1986.
Ayer, W. A., and Talamas, F. X. (1988) Can. J. Chem. 66, 1675-1685.
Ausubel, F. M., Brent, R., Kingston, R. E., Moore, D. D., Seidam, J. G., Smith, J. A., and Struhl, K. (1999) Curr. Prot. Mol. Biol. Wiley-Interscience, New York, N.Y.
Balz, J. P., Courtois, D., Drieu, J., Drieu, K., Reynoird, J. P., Sohier, C., Teng, B. P., Touche, A., Petiard, V. (1999) Production of ginkgolides and bilobalide by *Ginkgo biloba* plants and tissue cultures. Planta Medica 65(7): 620–626.
Bates, "Genetic transformation of plants by protoplast electroporation," Mol Biotechnol., 2(2):135–145, 1994.
Battraw and Hall, "Stable transformation of sorghum-bicolor protoplasts with chimeric neomycin phosphotransferase II and beta glucuronidase genes," Theor. App. Genet., 82(2):161–168, 1991.
Becker et al., "Fertile transgenic wheat from microprojectile bombardment of scutellar tissue," Plant J., 5(2):299–307, 1994.
Bhattacharjee; An; Gupta, J. Plant Bioch. and Biotech. 6, (2):69–73. 1997.
Bohlman, J., Meyer-Gauen, G., and Croteau, R. (1998) Proc. Natl. Acad. Sci. USA 95, 4126–4133.
Bower et al., The Plant Journal, 2:409–416. 1992.
Buising and Benbow, "Molecular analysis of transgenic plants generated by microprojectile bombardment: effect of petunia transformation booster sequence," Mol. Gen. Genet., 243:71–81, 1994.
Callis et al., Genes Dev., 1:1183–1200, 1987.
Cambie, R. C., Rutledge, P. S., Ryan, G. R., Strange, G. A., and Woodgate, P. D. (1990) Aust. J. Chem. 43, 867–881.
Cartayrade, A., Neau, E., Sohier, C., Balz, J-P.; Carde, J-P., and Walter, J. (1997) Plant Physiol. Biochem. 35, 859–868.
Casas et al., "Transgenic sorghum plants via microprojectile bombardment," Proc. Natl. Acad. Sci. USA, 90(23):11212–11216, 1993.
Chang, S., Puryear, J., and Cairney, J. (1993) Plant Mol. Bio. Rep. 11, 113–116.
Christou; Murphy; Swain, Proc. Nat'l Acad. Sci. USA, 84(12):3962–3966, 1987.
Coates, R. M., Ley, D. A., and Cavender, P. L. (1978) J. Org. Chem. 43, 4915–4922.
Corey, E. J., Kim, C. U., and Takeda, M. (1972) Tetrahedron Lett. 42, 4339–4342.
Corey, E. J., and Su, W-g. (1987) J. Am. Chem. Soc. 109, 7534–7536.
Corey, E. J., Kang, M-c., Desai, M. C., Ghosh, A. K., and Houpis, I. N. (1988) J. Am. Chem. Soc. 110, 649–651.
Corey, E. J., and Ghosh, A. K., (1988) Tetrahedron Lett. 29, 3205–3206.
Corey, E. J., Matsuda, S. P. T., Baker, C. H., Ting, A. Y., Cheng, H. (1996) Biochem. Biophys. Res. Commun. 219, 327–331.
Crimmins, M. T., Pace, J. M., Nantermet, P. G., Kim-Meade, A. S., Thomas, J. B., Watterson, S. H., and Wagman, A. S. (1999) J. Am. Chem. Soc. 121, 10249–10250.
Croteau, R., and Cane, D. E. (1985) Methods Enxymol. 110, 383–405.
Davisson, V. J., Woodside, A. B., and Poulter, C. D. (1985) M. Enzymol. 110, 130–144.
Davisson, V. J., Woodside, A. B., Neal, T. R., Stremler, K. E., Muehlbacher, M., and Poulter, C. D. (1986) J. Org. Chem. 51, 4768–4779.
D'Halluin et al., "Transgenic maize plants by tissue electroporation," Plant Cell, 4(12):1495–1505, 1992.
Fiehe, K., Arenz, A., Drewke, C., Hemscheidt, T., Williamson, R. T., Leistner, E. (2000) Biosynthesis of 4'-O-Methylpyridoxine (Ginkgotoxin) from primary precursors. J. Nat. Prod. 63:185–189.
Fromm et al., Nature, 312:791–793, 1986.
Fromm et al., "Stable transformation of maize after gene transfer by electroporation," Nature, 319:791–793, 1986.
Gerhardt G., Rogalla K., Jaeger J. (1990) Drug therapy of disorders of cerebral performance. Randomized comparative study of dihydroergotoxine and *Ginkgo biloba* extract. Fortschr Med Jun 30;108(19):384–8.
Ghosh-Biswas et al., "Transgenic Indica rice (*Oryza sativa* L.) plants obtained by direct gene transfer to protoplasts," J. Biotechnol., 32(1):1–10, 1994.
Gigante, B., Santos, C, Fonseca, T., Curto, M. J. M., Luftmann, H., Bergander, K., and Berberan-Santos, M. N. (1999) Tetrahedron 55, 6175–6182.
Hagio et al., "Stable transformation of sorghum cell cultures after bombardment with DNA coated microprojectiles," Plant Cell Rep., 10(5):260–264, 1991.
Hart, E. In *Chemistry*, Rice University: Houston, 2001, p. 142.

He et al., Plant Cell Reports, 14 (2–3):192–196, 1994.

Hensgens et al., "Transient and stable expression of gusA fusions with rice genes in rice, barley and perennial ryegrass," Plant Mol. Biol., 22(6):1101–1127, 1993.

Hiei et al., "Transformation of rice mediated by agrobacterium tumefaciens," Plant Mol. Biol., 35(1–2):205–218, 1997.

Hill, A. M., Cane, D. E., Mau, C. J. D., West, C. A. High level expression of Ricinus comunis casbene synthase in *Escherichia coli* and characterization of the recombinant enzyme. (1996) Arch. Biochem. Biophys. 336(2): 283–289.

Hosford, D. J., Domingo, M. T., Chabrier, P. E., and Braquet, P. (1990) Methods Enzymol. 187, 433–446.

Hou and Lin, Plant Physiology, 111:166, 1996.

Hua, L. (2000) Ph.D. Dissertation, Rice University, Houston, Tex.

Ishida et al., "High efficiency transformation of maize (*Zea mays* L.) mediated by *Agrobacterium tumefaciens*," Nat Biotechnol., 14:745–50, 1996.

Ito, H., Fukuda, Y., Murata, K., and Kimura, A. (1983) J. Bacteriol. 153, 163–168.

Kaeppler et al., Plant Cell Reports 9: 415–418, 1990.

Kaeppler et al., "Silicon carbide fiber-mediated stable transformation of plant cells," Theor. Appl. Genet., 84(5–6):560–566, 1992.

Keegstra, K., and Olsen, L. J. (1989) Annu. Rev. Plant Physiol. Plant Mol. Biol. 40, 471–501.

Klee et al., Bio-Technology, 3(7):637–642, 1985.

Knittel et al., Plant Cell Reports, 14(2–3):81–86, 1994.

Kutney, J. P., and Han, K. (1996) Rec. Trav. Chim. Pays-Bas 115, 77–93.

Le Bars P L, Katz M M, Berman N, Itil T M, Freedman A M, Schatzberg A F. (1997) A placebo-controlled, double-blind, randomized trial of an extract of *Ginkgo biloba* for dementia. North American EGb Study Group. J. Amer. Med. Assoc. 278(16): 1327–32.

Lazzeri, "Stable transformation of barley via direct DNA uptake. Electroporation- and PEG-mediated protoplast transformation," Methods Mol. Biol., 49:95–106, 1995.

Lee et al., Korean J. Genet., 11(2):65–72, 1989.

Li, T.-S., Li, J.-T., and Li, H.-Z. (1995) J. Chromatogr., A 715, 372–375.

Liu, H., and Krizek, J. (1992) Genetics 132, 665–673.

Lorz et al., Mol Gen Genet, 199:178–182, 1985.

Maas et al., "Preparation and transformation of monocot protoplasts," Methods Cell Biol., 50:383–399, 1995.

Marcotte et al., Nature, 335:454, 1988.

McCabe, Martinell, Bio-Technology, 11 (5):596–598, 1993.

McCormac et al., Euphytica, v. 99 (1) p. 17–25:. 1998.

Nagatani et al., "DNA delivery into rice cells and transformation using silicon carbide whiskers," Biotech. Tech., 11(7):471–473, 1997.

Nakanishi, K. Pure Appl. Chem. 7. 89 (1967).

Nakanishi, K. Tetrahedron Letter, 4. 299 (1967).

Neau, E., Cartayrade, A., Balz, J-P., Carde, J-P., and Walter, J. (1997) Plant Physiol. Biochem. 35, 869–879.

Nielsen, H., Engelbrecht, J., Brunak, S., and von Heijne, G. (1997) Protein Eng. 10, 1–6.

Omirulleh et al., "Activity of a chimeric promoter with the doubled CaMV 35S enhancer element in protoplast-derived cells and transgenic plants in maize." Plant Mol. Biol., 21:415–28, 1993.

Okabe, K. et al. J. Chem. Soc.(5) 2201 (1967).

Peters, R. J., Flory, J. E., Jetter, R., Ravn, M. M., Lee, H.-J., Coates, R. M., Croteau, R. B. (2000) Abietadiene synthase from Grand Fir (*Abies grandis*): characterization and mechanism of action of the "Pseudomature" recombinant enzyme. Biochem. 39:15592–15602.

Potrykus et al., Mol. Gen. Genet., 199:183–188, 1985.

Ravn, M. M., Coates, R. M., Jetter, R., and Croteau, R. (1998) Chem. Commun. 21–22.

Ravn, M. M., Coates, R. M., Flory, J. E., Peters, R. J., and Croteau, R. (2000) Org. Letts. 2, 573–576.

Rhodes et al., "Transformation of maize by electroporation of embryos," Methods Mol. Biol., 55:121–131, 1995.

Ritala et al., "Fertile transgenic barley to particle bombardment of immature embryos," Plant Mol. Biol., 24(2):317–325, 1994.

Rogers et al., Methods Enzymol., 153:253–277, 1987.

Ruan, B. (1999) Ph.D. Dissertation, Rice University, Houston, Tex., 1999.

Sambrook, Fritsch, Maniatis, In: *Molecular Cloning: A Laboratory Manual*, Vol. 1, Cold Spring Harbor Laboratory Press, Cold Spring Harbor, N.Y., Ch. 7,7.19–17.29, 1989.

Schenk, P. M., Baumann, S., Mattes, R., Steinbiss, H. (1995) BioTechniques 19:196–200.

Schwarz, M. (1994) Ph.D. Dissertation, E. T. H., Zurich, Switzerland, 1994.

Schwarz, M., and Arigoni, D. (1999) Comp. Nat. Prod. Chem. 2, 367–400.

Shimoni et al., "A recombinant protein of two high molelcular weight glutenins alters gluten polymer formation in transgenic wheat," J. Biol. Chem., 272:15488–15495, 1997.

Singsit et al., "Expression of a *Bacillus thuringiensis* cryIA (c) gene in transgenic peanut plants and its efficacy against lesser cornstalk borer," Transgenic Res., 6:169–76, 1997.

Starks, C. M., Back, K., Chappell, J., and Noel, J. P. (1997) Science 277, 1815–1820.

Takumi and Shimada, "Variation in transformation frequencies among six common wheat cultivars through particle bombardment of scutellar tissues," Genes Genet. Sys., 72:63–69, 1997.

Thompson et al., "Maize transformation utilizing silicon carbide whiskers: A review," Euphytica, 85(1–3):75–80, 1995.

Tingay et al., The Plant Journal v. 11 (6) p. 1369–1376. 1997.

Tomes et al., "Transgenic tobacco plants and their progeny derived by microprojectile bombardment of tobacco leaves," Plant Mol. Biol., 14:261–8, 1990.

Torbet et al., "Transformation of oat using mature embryo-derived tissue cultures," Crop Science, 38:226–231, 1998.

Torbet et al., "Use of paromomycin as a selective agent for oat transformation," Plant Cell Reports, 14:635–640, 1995.

Toriyama et al., Theor Appl. Genet., 73:16, 1986.

Tsukada; Kusano; Kitagawa, Plant Cell Physiol., 30(4) 599–604, 1989.

Uchimiya et al., Mol. Gen. Genet., 204:204, 1986.

Van Eck; Blowers; Earle, Plant Cell Reports, 14(5):299–304, 1995.

Vasil et al., Plant Physiol., 91:1575–1579, 1989.

von Heijne, G., and Nishikawa, K. (1991) FEBS 278, 1–3.

von Heijne, G., and Gavel, Y. (1990) FEBS 261, 455–458.

Walter, J. (1988) Thèse d'Etat, Université Bordeaux I, Bordeaux, France.

Williams, D. C., Wildung, M. R., Jin, A. Q., Dalal, D., Oliver, J. S., Coates, R. M., and Croteau, R. (2000) Archives Biochem. Biophys. 379, 137–146.

Yamada et al., Plant Cell Rep., 4:85, 1986.

Zhang et al., "Agrobacterium-mediated transformation of elite indica and japonica rice cultivars," Mol. Biotechnol., 8(3):223–231, 1997.

Zheng and Edwards, "Expression of resistance to barley stripe mosaic virus in barley and oat protoplasts," J. Gen. Virol., 71:1865–1868, 1990.

Zhou et al., Plant Cell Reports, 12(11).612–616, 1993.

One skilled in the art readily appreciates that the patent invention is well adapted to carry out the objectives and obtain the ends and advantages mentioned as well as those inherent therein. Plant cells, yeast cells, cell cultures, plants, sequences, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A purified and isolated nucleic acid sequence encoding a levopimaradiene synthase and comprising SEQ.ID.NO:36.

2. An expression vector comprising an isolated and purified nucleic acid sequence encoding a levopimaradiene synthase and comprising SEQ.ID.NO:36, the sequence under the control of a promoter operable in a host cell.

3. The expression vector of claim 2, wherein said promoter is an inducible promoter.

4. The expression vector of claim 3, wherein said inducible promoter is GAL1.

5. The expression vector of claim 2, wherein said host cell is a prokaryote.

6. The expression vector of claim 5, wherein said prokaryote is *Escherichia coli*.

7. The expression vector of claim 2, wherein said host cell is a eukaryote.

8. The expression vector of claim 7, wherein said eukaryote is a yeast.

9. An expression vector comprising an isolated polynucleotide sequence encoding a polypeptide having an amino acid sequence of a levopimaradiene synthase and comprising SEQ.ID.NO:37.

10. A unicellular organism comprising a purified and isolated nucleic acid sequence encoding a levopimaradiene synthase and comprising SEQ.ID.NO:36.

11. The unicellular organism of claim 10, wherein said nucleic acid sequence further comprises an expression vector.

12. The unicellular organism of claim 11, wherein said expression vector comprises an inducible promoter.

13. The unicellular organism of claim 12, wherein said inducible promoter is GAL1.

14. The unicellular organism of claim 10, wherein said nucleic acid sequence encoding said levopimaradiene synthase contains a deletion in the N-terminal sequence.

15. The unicellular organism of claim 10, wherein said organism is *Saccharomyces, Escherichia coli, Candida albicans* or *Kluyveromyces lactis*.

16. The unicellular organism of claim 10, wherein said organism is *Escherichia coil*.

17. The unicellular organism of claim 10, wherein said organism is *Saccharomyces cerevisiae*.

18. A yeast host cell comprising a vector, wherein said vector comprises a purified and isolated nucleic acid sequence encoding a levopimaradiene synthase and comprising SEQ.ID.NO:36 under control of a promoter operable in said yeast host cell.

19. A yeast host cell comprising a vector, wherein said vector comprises an isolated polynucleotide sequence encoding a polypeptide having an amino acid sequence of a levopimaradiene synthase and comprising SEQ.ID.NO:37, the polynucleotide sequence under control of a promoter operable in said yeast host cell.

20. A plant host cell comprising an isolated and purified nucleic acid sequence encoding a levopimaradiene synthase and comprising SEQ.ID.NO:36 under control of a promoter operable in said plant host cell.

21. The plant host cell of claim 20, wherein said plant is *Ginkgo biloba*.

* * * * *

SEQUENCE LISTING

<160> NUMBER OF SEQ ID NOS: 41

<210> SEQ ID NO 1
<211> LENGTH: 2705
<212> TYPE: DNA
<213> ORGANISM: ginkgo biloba

<400> SEQUENCE: 1

```
atatttgcct aaacctgcac aaatggctgg ggtgctcttt gcaaatctgc cttgctcact      60
gcaactctct ccaaaagttc ccttccggca atccactaat attcttattc cttttcacaa     120
gagatcctca tttggattta atgcacagca ctgcgtccgt tctcacttaa ggctgagatg     180
gaattgtgtc gggattcatg cctcagctgc agagactcgt ccagatcagc ttccacagga     240
ggaacgcttt gtgtcgagac ttaatgcgga ttatcatcca gctgtctgga aggacgattt     300
catcgactct ctaacatccc ctaattccca cgcgacatcg aaatcaagcg tcgatgagac     360
aatcaataaa agaatccaga cattggtgaa ggaaatccag tgcatgtttc agtccatggg     420
cgacggtgaa acgaatccat ctgcatatga tacagcttgg gtggcaagaa ttccgtcaat     480
tgacggctct ggtgcacccc aatttcccca aacgcttcaa tggattctga acaatcaact     540
gccagatggc tcgtggggtg aggagtgcat ttttctggcg tatgacagag ttttaaacac     600
tctcgcctgc ctcctcactc tcaaaatatg gaataagggc gacattcaag tgcagaaagg     660
ggttgagttt gtgagaaaac acatggaaga aatgaaggac gaagctgaca atcacaggcc     720
aagtggattc gaggtcgtgt ttcctgcaat gttagatgaa gcaaaaagct tgggattgga     780
tcttccttat cacctcccct tcatctccca aatccaccaa aagcgccaga aaaagcttca     840
aaagattccc ctcaatgttc ttcataacca tcagacggcg ttgctctact ctctggaggg     900
tttgcaagat gtggtggact ggcaagagat cacaaatctt caatcaagag acggatcatt     960
tttaagctcc cctgcatcta ctgcttgtgt cttcatgcac actcaaaaca aacgatgcct    1020
ccactttctc aacttcgtgc tcagcaaatt tggcgactac gttccttgcc attacccact    1080
tgatctattt gaacgcctct gggctgtcga tacagttgaa cgcttgggaa tcgatcgcta    1140
tttcaagaaa gaaatcaaag aatctctgga ttacgtttat aggtactggg acgccgaaag    1200
aggcgtggga tggcaagat gcaatcctat tcctgatgtc gatgacactg ccatgggtct    1260
tagaatcctg agacttcatg gatacaatgt atcttcagat gttctggaga atttcagaga    1320
cgagaaagga gacttctttt gctttgccgg tcaaacgcaa attggtgtga ccgataatct    1380
taacctttat agatgttcac aagtatgttt tccgggagaa aagataatgg aagaagctaa    1440
gaccttcact acaaatcatc tccaaaatgc tcttgccaaa acaacgcat  ttgataagtg    1500
ggctgtcaag aaggatcttc ctggagaggt ggagtatgct ataaagtatc cgtggcatag    1560
aagtatgcca agattggagg caagaagtta catagagcaa tttggatcaa atgatgtctg    1620
gctggggaag actgtgtata agatgctata tgtgagcaac gaaaaatatt tggagctggc    1680
```

-continued

```
caaattggac ttcaatatgg tgcaggcctt acaccaaaag gagactcaac acattgtcag    1740
ctggtggaga gaatcgggat tcaatgatct tacattcacc cgccagcggc ctgtggaaat    1800
gtatttctca gtggcggtta gtatgtttga gccagaattc gctgcttgta gaattgccta    1860
tgccaagact tcttgcctcg cagttattct agacgatctt tacgacaccc acggatctct    1920
ggatgatctt aaattgttct ctgaagcggt ccgaagatgg gatatctctg tgctggatag    1980
cgttcgggat aatcagttga aagtttgctt cctagggctg tacaacacag tgaatggatt    2040
tggaaaagat ggactcaagg aacaaggccg tgatgtgctg ggctatcttc gaaaagtatg    2100
ggagggcttg ctcgcatcgt ataccaaaga agccgaatgg tcggcagcaa agtatgtgcc    2160
gacattcaac gaatatgtgg aaaatgccaa agtgtccata gcacttgcga cagtcgtact    2220
aaactcaatc ttttcactg gagaattact tcctgattac attttacagc aagtagacct     2280
tcggtccaaa tttctgcatc ttgtgtcttt gactggacga ctaatcaatg acaccaagac    2340
ttaccaggcc gagagaaacc gtggtgaatt ggtttccagc gtacagtgct acatgaggga    2400
aaatccggag tgcacagagg aagaagctct aagtcatgtt tatggtatca tcgacaacgc    2460
actgaaggaa ttgaattggg agttggccaa cccagcgagc aatgccccat tgtgtgtgag    2520
aagactgctg ttcaacactg caagagtgat gcagctgttt tatatgtaca gagatggctt    2580
tggtatctct gacaaagaga tgaaagacca tgtcagccga actcttttcg atcctgtggc    2640
gtagcatact gatattatat ataatattca tattcaatcc aaaaaaaaaa aaaaaaaaa     2700 aaaaa                                                                2705
```

<210> SEQ ID NO 2
<211> LENGTH: 873
<212> TYPE: PRT
<213> ORGANISM: Ginkgo biloba

<400> SEQUENCE: 2

```
Met Ala Gly Val Leu Phe Ala Asn Leu Pro Cys Ser Leu Gln Leu Ser
1               5                   10                  15

Pro Lys Val Pro Phe Arg Gln Ser Thr Asn Ile Leu Ile Pro Phe His
            20                  25                  30

Lys Arg Ser Ser Phe Gly Phe Asn Ala Gln His Cys Val Arg Ser His
        35                  40                  45

Leu Arg Leu Arg Trp Asn Cys Val Gly Ile His Ala Ser Ala Ala Glu
    50                  55                  60

Thr Arg Pro Asp Gln Leu Pro Gln Glu Glu Arg Phe Val Ser Arg Leu
65                  70                  75                  80

Asn Ala Asp Tyr His Pro Ala Val Trp Lys Asp Asp Phe Ile Asp Ser
                85                  90                  95

Leu Thr Ser Pro Asn Ser His Ala Thr Ser Lys Ser Ser Val Asp Glu
            100                 105                 110

Thr Ile Asn Lys Arg Ile Gln Thr Leu Val Lys Glu Ile Gln Cys Met
        115                 120                 125

Phe Gln Ser Met Gly Asp Gly Glu Thr Asn Pro Ser Ala Tyr Asp Thr
    130                 135                 140

Ala Trp Val Ala Arg Ile Pro Ser Ile Asp Gly Ser Gly Ala Pro Gln
145                 150                 155                 160

Phe Pro Gln Thr Leu Gln Trp Ile Leu Asn Asn Gln Leu Pro Asp Gly
                165                 170                 175

Ser Trp Gly Glu Glu Cys Ile Phe Leu Ala Tyr Asp Arg Val Leu Asn
            180                 185                 190
```

```
Thr Leu Ala Cys Leu Leu Thr Leu Lys Ile Trp Asn Lys Gly Asp Ile
        195                 200                 205

Gln Val Gln Lys Gly Val Glu Phe Val Arg Lys His Met Glu Met
    210                 215                 220

Lys Asp Glu Ala Asp Asn His Arg Pro Ser Gly Phe Glu Val Val Phe
225                 230                 235                 240

Pro Ala Met Leu Asp Glu Ala Lys Ser Leu Gly Leu Asp Leu Pro Tyr
                245                 250                 255

His Leu Pro Phe Ile Ser Gln Ile His Gln Lys Arg Gln Lys Lys Leu
            260                 265                 270

Gln Lys Ile Pro Leu Asn Val Leu His Asn His Gln Thr Ala Leu Leu
        275                 280                 285

Tyr Ser Leu Glu Gly Leu Gln Asp Val Val Asp Trp Gln Glu Ile Thr
    290                 295                 300

Asn Leu Gln Ser Arg Asp Gly Ser Phe Leu Ser Ser Pro Ala Ser Thr
305                 310                 315                 320

Ala Cys Val Phe Met His Thr Gln Asn Lys Arg Cys Leu His Phe Leu
                325                 330                 335

Asn Phe Val Leu Ser Lys Phe Gly Asp Tyr Val Pro Cys His Tyr Pro
            340                 345                 350

Leu Asp Leu Phe Glu Arg Leu Trp Ala Val Asp Thr Val Glu Arg Leu
        355                 360                 365

Gly Ile Asp Arg Tyr Phe Lys Lys Glu Ile Lys Glu Ser Leu Asp Tyr
    370                 375                 380

Val Tyr Arg Tyr Trp Asp Ala Glu Arg Gly Val Gly Trp Ala Arg Cys
385                 390                 395                 400

Asn Pro Ile Pro Asp Val Asp Asp Thr Ala Met Gly Leu Arg Ile Leu
                405                 410                 415

Arg Leu His Gly Tyr Asn Val Ser Ser Asp Val Leu Glu Asn Phe Arg
            420                 425                 430

Asp Glu Lys Gly Asp Phe Phe Cys Phe Ala Gly Gln Thr Gln Ile Gly
        435                 440                 445

Val Thr Asp Asn Leu Asn Leu Tyr Arg Cys Ser Gln Val Cys Phe Pro
    450                 455                 460

Gly Glu Lys Ile Met Glu Glu Ala Lys Thr Phe Thr Thr Asn His Leu
465                 470                 475                 480

Gln Asn Ala Leu Ala Lys Asn Asn Ala Phe Asp Lys Trp Ala Val Lys
                485                 490                 495

Lys Asp Leu Pro Gly Glu Val Glu Tyr Ala Ile Lys Tyr Pro Trp His
            500                 505                 510

Arg Ser Met Pro Arg Leu Glu Ala Arg Ser Tyr Ile Glu Gln Phe Gly
        515                 520                 525

Ser Asn Asp Val Trp Leu Gly Lys Thr Val Tyr Lys Met Leu Tyr Val
    530                 535                 540

Ser Asn Glu Lys Tyr Leu Glu Leu Ala Lys Leu Asp Phe Asn Met Val
545                 550                 555                 560

Gln Ala Leu His Gln Lys Glu Thr Gln His Ile Val Ser Trp Trp Arg
                565                 570                 575

Glu Ser Gly Phe Asn Asp Leu Thr Phe Thr Arg Gln Arg Pro Val Glu
            580                 585                 590

Met Tyr Phe Ser Val Ala Val Ser Met Phe Glu Pro Glu Phe Ala Ala
        595                 600                 605
```

```
Cys Arg Ile Ala Tyr Ala Lys Thr Ser Cys Leu Ala Val Ile Leu Asp
            610                 615                 620

Asp Leu Tyr Asp Thr His Gly Ser Leu Asp Asp Leu Lys Leu Phe Ser
625                 630                 635                 640

Glu Ala Val Arg Arg Trp Asp Ile Ser Val Leu Asp Ser Val Arg Asp
                645                 650                 655

Asn Gln Leu Lys Val Cys Phe Leu Gly Leu Tyr Asn Thr Val Asn Gly
            660                 665                 670

Phe Gly Lys Asp Gly Leu Lys Glu Gln Gly Arg Asp Val Leu Gly Tyr
        675                 680                 685

Leu Arg Lys Val Trp Glu Gly Leu Leu Ala Ser Tyr Thr Lys Glu Ala
        690                 695                 700

Glu Trp Ser Ala Ala Lys Tyr Val Pro Thr Phe Asn Glu Tyr Val Glu
705                 710                 715                 720

Asn Ala Lys Val Ser Ile Ala Leu Ala Thr Val Val Leu Asn Ser Ile
                725                 730                 735

Phe Phe Thr Gly Glu Leu Leu Pro Asp Tyr Ile Leu Gln Gln Val Asp
            740                 745                 750

Leu Arg Ser Lys Phe Leu His Leu Val Ser Leu Thr Gly Arg Leu Ile
        755                 760                 765

Asn Asp Thr Lys Thr Tyr Gln Ala Glu Arg Asn Arg Gly Glu Leu Val
770                 775                 780

Ser Ser Val Gln Cys Tyr Met Arg Glu Asn Pro Glu Cys Thr Glu Glu
785                 790                 795                 800

Glu Ala Leu Ser His Val Tyr Gly Ile Ile Asp Asn Ala Leu Lys Glu
                805                 810                 815

Leu Asn Trp Glu Leu Ala Asn Pro Ala Ser Asn Ala Pro Leu Cys Val
            820                 825                 830

Arg Arg Leu Leu Phe Asn Thr Ala Arg Val Met Gln Leu Phe Tyr Met
        835                 840                 845

Tyr Arg Asp Gly Phe Gly Ile Ser Asp Lys Glu Met Lys Asp His Val
850                 855                 860

Ser Arg Thr Leu Phe Asp Pro Val Ala
865                 870

<210> SEQ ID NO 3
<211> LENGTH: 2861
<212> TYPE: DNA
<213> ORGANISM: Abies grandis

<400> SEQUENCE: 3
agatggccat gccttcctct tcattgtcat cacagattcc cactgctgct catcatctaa      60
ctgctaacgc acaatccatt ccgcatttct ccacgacgct gaatgctgga agcagtgcta     120
gcaaacggag aagcttgtac ctacgatggg gtaaaggttc aaacaagatc attgcctgtg     180
ttggagaagg tggtgcaacc tctgttcctt atcagtctgc tgaaaagaat gattcgcttt     240
cttcttctac attggtgaaa cgagaatttc ctccaggatt ttggaaggat gatcttatcg     300
attctctaac gtcatctcac aaggttgcag catcagacga gaagcgtatc gagacattaa     360
tatccgagat taagaatatg tttagatgta tgggctatgg cgaaacgaat ccctctgcat     420
atgacactgc ttgggtagca aggattccag cagttgatgg ctctgacaac cctcactttc     480
ctgagacggt tgaatggatt ttcaaaaatc agttgaaaga tgggtcttgg ggtgaaggat     540
tctacttctt ggcatatgac agaatactgg ctacacttgc atgtattatt acccttaccc     600
```

-continued

```
tctggcgtac tggggagaca caagtacaga aaggtattga attcttcagg cacaagctg     660 gaaagatgga agatgaagct gatagtcata ggccaagtgg atttgaaata gtatttcctg    720
caatgctaaa ggaagctaaa atcttaggct tggatctgcc ttacgatttg ccattcctga    780
aacaaatcat cgaaaagcgg gaggctaagc ttaaaaggat tcccactgat gttctctatg    840
cccttccaac aacgttattg tattctttgg aaggtttaca agaaatagta gactggcaga    900
aaataatgaa acttcaatcc aaggatggat catttctcag ctctccggca tctacagcgg    960
ctgtattcat gcgtacaggg aacaaaaagt gcttggattt cttgaacttt gtcttgaaga   1020
aattcggaaa ccatgtgcct tgtcactatc cgcttgatct atttgaacgt ttgtgggcgg   1080
ttgatacagt tgagcggcta ggtatcgatc gtcatttcaa agaggagatc aaggaagcat   1140
tggattatgt ttacagccat tgggacgaaa gaggcattgg atgggcgaga gagaatcctg   1200
ttcctgatat tgatgataca gccatgggcc ttcgaatctt gagattacat ggatacaatg   1260
tatcctcaga tgttttaaaa acatttagag atgagaatgg ggagttcttt tgcttcttgg   1320
gtcaaacaca gagaggagtt acagacatgt aaacgtcaa tcgttgttca catgtttcat    1380
ttccgggaga aacgatcatg gaagaagcaa aactctgtac cgaaaggtat ctgaggaatg   1440
ctctggaaaa tgtggatgcc tttgacaaat gggcttttaa aaagaatatt cggggagagg   1500
tagagtatgc actcaaatat ccctggcata agagtatgcc aaggttggag gctagaagct   1560
atattgaaaa ctatgggcca gatgatgtgt ggcttggaaa aactgtatat atgatgccat   1620
acatttcgaa tgaaaagtat ttagaactag cgaaactgga cttcaataag gtgcagtcta   1680
tacaccaaac agagcttcaa gatcttcgaa ggtggtggaa atcatccggt ttcacggatc   1740
tgaatttcac tcgtgagcgt gtgacggaaa tatatttctc accggcatcc tttatctttg   1800
agcccgagtt ttctaagtgc agagaggttt atacaaaaac ttccaatttc actgttattt   1860
tagatgatct ttatgacgcc catggatctt tagacgatct taagttgttc acagaatcag   1920
tcaaaagatg ggatctatca ctagtggacc aaatgccaca acaaatgaaa atatgttttg   1980
tgggtttcta caatactttt aatgatatag caaagaagg acgtgagagg caagggcgcg    2040
atgtgctagg ctacattcaa aatgtttgga aagtccaact tgaagcttac acgaaagaag   2100
cagaatggtc tgaagctaaa tatgtgccat ccttcaatga atacatagag aatgcgagtg   2160
tgtcaatagc attgggaaca gtcgttctca ttagtgctct tttcactggg gaggttctta   2220
cagatgaagt actctccaaa attgatcgcg aatctagatt tcttcaactc atgggcttaa   2280
cagggcgttt ggtgaatgac accaaaactt atcaggcaga gagaggtcaa ggtgaggtgg   2340
cttctgccat acaatgttat atgaaggacc atcctaaaat ctctgaagaa gaagctctac   2400
aacatgtcta tagtgtcatg gaaaatgccc tcgaagagtt gaataggggag tttgtgaata   2460 acaaaatacc ggatatttac aaaagactgg ttttttgaaac tgcaagaata atgcaactct   2520
tttatatgca aggggatggt ttgacactat cacatgatat ggaaattaaa gagcatgtca   2580
aaaattgcct cttccaacca gttgcctaga ttaaattatt cagttaaagg ccctcatggt   2640
attgtgttaa cattataata acagatgctc aaaagctttg agcggtattt gttaaggcta   2700
tctttgtttg tttgtttgtt tactgccaac caaaaagcgt tcctaaacct ttgaagacat   2760
ttccatccaa gagatgggagt ctacattta tttatgagat tgaattattt caagagaata   2820
tactacatat atttaaaagt aaaaaaaaaa aaaaaaaaa a                         2861
```

<210> SEQ ID NO 4
<211> LENGTH: 868
<212> TYPE: PRT
<213> ORGANISM: Abies grandis

<400> SEQUENCE: 4

```
Met Ala Met Pro Ser Ser Leu Ser Ser Gln Ile Pro Thr Ala Ala
1               5                   10                  15

His His Leu Thr Ala Asn Ala Gln Ser Ile Pro His Phe Ser Thr Thr
            20                  25                  30

Leu Asn Ala Gly Ser Ser Ala Ser Lys Arg Arg Ser Leu Tyr Leu Arg
        35                  40                  45

Trp Gly Lys Gly Ser Asn Lys Ile Ile Ala Cys Val Gly Glu Gly Gly
50                  55                  60

Ala Thr Ser Val Pro Tyr Gln Ser Ala Glu Lys Asn Asp Ser Leu Ser
65                  70                  75                  80

Ser Ser Thr Leu Val Lys Arg Glu Phe Pro Pro Gly Phe Trp Lys Asp
                85                  90                  95

Asp Leu Ile Asp Ser Leu Thr Ser Ser His Lys Val Ala Ala Ser Asp
            100                 105                 110

Glu Lys Arg Ile Glu Thr Leu Ile Ser Glu Ile Lys Asn Met Phe Arg
        115                 120                 125

Cys Met Gly Tyr Gly Glu Thr Asn Pro Ser Ala Tyr Asp Thr Ala Trp
130                 135                 140

Val Ala Arg Ile Pro Ala Val Asp Gly Ser Asp Asn Pro His Phe Pro
145                 150                 155                 160

Glu Thr Val Glu Trp Ile Leu Gln Asn Gln Leu Lys Asp Gly Ser Trp
                165                 170                 175

Gly Glu Gly Phe Tyr Phe Leu Ala Tyr Asp Arg Ile Leu Ala Thr Leu
            180                 185                 190

Ala Cys Ile Ile Thr Leu Thr Leu Trp Arg Thr Gly Glu Thr Gln Val
        195                 200                 205

Gln Lys Gly Ile Glu Phe Phe Arg Thr Gln Ala Gly Lys Met Glu Asp
210                 215                 220

Glu Ala Asp Ser His Arg Pro Ser Gly Phe Glu Ile Val Phe Pro Ala
225                 230                 235                 240

Met Leu Lys Glu Ala Lys Ile Leu Gly Leu Asp Leu Pro Tyr Asp Leu
                245                 250                 255

Pro Phe Leu Lys Gln Ile Ile Glu Lys Arg Glu Ala Lys Leu Lys Arg
            260                 265                 270

Ile Pro Thr Asp Val Leu Tyr Ala Leu Pro Thr Thr Leu Leu Tyr Ser
        275                 280                 285

Leu Glu Gly Leu Gln Glu Ile Val Asp Trp Gln Lys Ile Met Lys Leu
290                 295                 300

Gln Ser Lys Asp Gly Ser Phe Leu Ser Ser Pro Ala Ser Thr Ala Ala
305                 310                 315                 320

Val Phe Met Arg Thr Gly Asn Lys Lys Cys Leu Asp Phe Leu Asn Phe
                325                 330                 335

Val Leu Lys Lys Phe Gly Asn His Val Pro Cys His Tyr Pro Leu Asp
            340                 345                 350

Leu Phe Glu Arg Leu Trp Ala Val Asp Thr Val Glu Arg Leu Gly Ile
        355                 360                 365

Asp Arg His Phe Lys Glu Glu Ile Lys Glu Ala Leu Asp Tyr Val Tyr
370                 375                 380
```

-continued

```
Ser His Trp Asp Glu Arg Gly Ile Gly Trp Ala Arg Glu Asn Pro Val
385                 390                 395                 400

Pro Asp Ile Asp Asp Thr Ala Met Gly Leu Arg Ile Leu Arg Leu His
            405                 410                 415

Gly Tyr Asn Val Ser Ser Asp Val Leu Lys Thr Phe Arg Asp Glu Asn
            420                 425                 430

Gly Glu Phe Phe Cys Phe Leu Gly Gln Thr Gln Arg Gly Val Thr Asp
            435                 440                 445

Met Leu Asn Val Asn Arg Cys Ser His Val Ser Phe Pro Gly Glu Thr
    450                 455                 460

Ile Met Glu Glu Ala Lys Leu Cys Thr Glu Arg Tyr Leu Arg Asn Ala
465                 470                 475                 480

Leu Glu Asn Val Asp Ala Phe Asp Lys Trp Ala Phe Lys Lys Asn Ile
            485                 490                 495

Arg Gly Glu Val Glu Tyr Ala Leu Lys Tyr Pro Trp His Lys Ser Met
            500                 505                 510

Pro Arg Leu Glu Ala Arg Ser Tyr Ile Glu Asn Tyr Gly Pro Asp Asp
            515                 520                 525

Val Trp Leu Gly Lys Thr Val Tyr Met Met Pro Tyr Ile Ser Asn Glu
    530                 535                 540

Lys Tyr Leu Glu Leu Ala Lys Leu Asp Phe Asn Lys Val Gln Ser Ile
545                 550                 555                 560

His Gln Thr Glu Leu Gln Asp Leu Arg Arg Trp Trp Lys Ser Ser Gly
            565                 570                 575

Phe Thr Asp Leu Asn Phe Thr Arg Glu Arg Val Thr Glu Ile Tyr Phe
            580                 585                 590

Ser Pro Ala Ser Phe Ile Phe Glu Pro Glu Phe Ser Lys Cys Arg Glu
            595                 600                 605

Val Tyr Thr Lys Thr Ser Asn Phe Thr Val Ile Leu Asp Asp Leu Tyr
    610                 615                 620

Asp Ala His Gly Ser Leu Asp Asp Leu Lys Leu Phe Thr Glu Ser Val
625                 630                 635                 640

Lys Arg Trp Asp Leu Ser Leu Val Asp Gln Met Pro Gln Gln Met Lys
            645                 650                 655

Ile Cys Phe Val Gly Phe Tyr Asn Thr Phe Asn Asp Ile Ala Lys Glu
            660                 665                 670

Gly Arg Glu Arg Gln Gly Arg Asp Val Leu Gly Tyr Ile Gln Asn Val
            675                 680                 685

Trp Lys Val Gln Leu Glu Ala Tyr Thr Lys Glu Ala Glu Trp Ser Glu
    690                 695                 700

Ala Lys Tyr Val Pro Ser Phe Asn Glu Tyr Ile Glu Asn Ala Ser Val
705                 710                 715                 720

Ser Ile Ala Leu Gly Thr Val Val Leu Ile Ser Ala Leu Phe Thr Gly
            725                 730                 735

Glu Val Leu Thr Asp Glu Val Leu Ser Lys Ile Asp Arg Glu Ser Arg
            740                 745                 750

Phe Leu Gln Leu Met Gly Leu Thr Gly Arg Leu Val Asn Asp Thr Lys
            755                 760                 765

Thr Tyr Gln Ala Glu Arg Gly Gln Gly Glu Val Ala Ser Ala Ile Gln
    770                 775                 780

Cys Tyr Met Lys Asp His Pro Lys Ile Ser Glu Glu Ala Leu Gln
785                 790                 795                 800
```

-continued

```
His Val Tyr Ser Val Met Glu Asn Ala Leu Glu Leu Asn Arg Glu
            805                 810                 815

Phe Val Asn Asn Lys Ile Pro Asp Ile Tyr Lys Arg Leu Val Phe Glu
            820                 825                 830

Thr Ala Arg Ile Met Gln Leu Phe Tyr Met Gln Gly Asp Gly Leu Thr
            835                 840                 845

Leu Ser His Asp Met Glu Ile Lys Glu His Val Lys Asn Cys Leu Phe
        850                 855                 860

Gln Pro Val Ala
865

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
atgtggtgga ctggcaagag                                           20

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
taaagatcgt ccagaataac                                           20

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aactgccaga tggctcgtgg                                           20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
ggtggagtat gctataaagt                                           20

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
cagagccgtc aattgacgga attc                                      24
```

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
catcgacgct tgatttcgat gtcg                                    24

<210> SEQ ID NO 11
<211> LENGTH: 56
<212> TYPE: DNA
<213> ORGANISM: Artificial Sequence
<220> FEATURE:
<223> OTHER INFORMATION: Primer

<400> SEQUENCE: 11
ttgcaaagag caccccagcc attttttttg tcgacacccg ggaattccgg accggt    56

<210> SEQ ID NO 12
<211> LENGTH: 56
<212> TYPE: DNA
<213> ORGANISM: Artificial Sequence
<220> FEATURE:
<223> OTHER INFORMATION: Primer

<400> SEQUENCE: 12
tggacgagtc tctgcagctg acattttttt ttgtcgacca attccatctc agcctt    56

<210> SEQ ID NO 13
<211> LENGTH: 2528
<212> TYPE: DNA
<213> ORGANISM: Abies grandis

<400> SEQUENCE: 13
atggctggcg tttctgctgt atcaaaggtt tccagcttgg tttgtgattt gtcgagtacc    60
agcggcttga ttcgaagaac tgccaatcct catcccaatg tctggggtta tgatcttgtg   120
cattctctta aatcacctta tattgattct agttacagag aacgcgcgga ggtccttgtt   180
agcgagatta aagcgatgct taatccagct attacaggag atggagaatc aatgattact   240
ccatctgctt atgacacagc atgggtagcg agggtgcccg ccattgatgg ctctgctcgc   300
ccgcaatttc cccaaacagt tgactggatt ttgaaaaacc agttaaaaga tggttcatgg   360
ggaattcagt cccactttct gctgtccgac cgtcttcttg ccactctttc ttgtgttctt   420
gtgctcctta aatggaacgt tggggatctg caagtagagc agggaattga attcataaag   480
agcaatctgg aactagtaaa ggatgaaacc gatcaagata gcttggtaac agactttgag   540
atcatatttc cttctctgtt aagagaagct caatctctgc gcctcggact tcgctacgac   600
ctgccttata tacatctgtt gcagactaaa cggcaggaaa gattagcaaa actttcaagg   660
gaggaaattt atgcggttcc gtcgccattg ttgtattctt tagagggaat acaagatata   720
gttgaatggg aacgaataat ggaagttcaa agtcaggatg gtctttcttt aagctcacct   780
gcttctactg cctgcgtttt catgcacaca ggagacgcga aatgccttga attcttgaac   840
agtgtgatga tcaagtttgg aaattttgtt cctgcctgt atcctgtgga tctgctggaa   900
cgcctgttga tcgtagataa tattgtacgc cttggaatct atagacactt tgaaaaggaa   960
atcaaggaag ctcttgatta tgtttacagg cattggaacg aaagaggaat tgggtggggc  1020
agactaaatc ccatagcaga tcttgagacc actgctttgg gatttcgatt gcttcggctg  1080

```
cataggtaca atgtatctcc agccattttt gacaacttca aagatgccaa tgggaaattc    1140
atttgctcga ccggtcaatt caacaaagat gtagcaagca tgctgaatct ttatagagct    1200
tcccagctcg catttcccgg agaaaacatt cttgatgaag ctaaaagctt cgctactaaa    1260
tatttgagag aagctcttga gaaaagtgag acttccagtg catggaacaa caaacaaaac    1320
ctgagccaag agatcaaata cgcgctgaag acttcttggc atgccagtgt tccgagagtg    1380
gaagcaaaga gatactgtca agtgtatcgc ccagattatg cacgcatagc aaaatgcgtt    1440
tacaagctac cctacgtgaa caatgaaaag ttttagagc tgggaaaatt agatttcaac     1500
attatccagt ccatccacca agaagaaatg aagaatgtta ccagctggtt tagagattcg    1560
gggttgccac tattcacctt cgctcgggag aggccgctgg aattctactt cttagtagcg    1620
gcggggacct atgaacccca gtatgccaaa tgcaggttcc tctttacaaa agtggcatgc    1680
ttgcagactg ttctggacga tatgtatgac acttatggaa ccctagatga attgaagcta    1740
ttcactgagg ctgtgagaag atgggacctc tcctttacag aaaaccttcc agactatatg    1800
aaactatgtt accaaatcta ttatgacata gttcacgagg tggcttggga ggcagagaag    1860
gaacaggggc gtgaattggt cagcttttc agaaagggat gggaggatta tcttctgggt    1920
tattatgaag aagctgaatg gttagctgct gagtatgtgc ctaccttgga cgagtacata    1980
aagaatggaa tcacatctat cggccaacgt atacttctgt tgagtggagt gttgataatg    2040
gatgggcaac tcctttcgca agaggcatta gagaaagtag attatccagg aagacgtgtt    2100
ctcacagagc tgaatagcct catttcccgc ctggcggatg acacgaagac atataaagct    2160
gagaaggctc gtggagaatt ggcgtccagc attgaatgtt acatgaaaga ccatcctgaa    2220
tgtacagagg aagaggctct cgatcacatc tatagcattc tggagccggc ggtgaaggaa    2280
ctgacaagag agtttctgaa gcccgacgac gtcccattcg cctgcaagaa gatgcttttc    2340
gaggagacaa gagtgacgat ggtgatattc aaggatggag atggattcgg tgtttccaaa    2400
ttagaagtca aagatcatat caaagagtgt ctcattgaac cgctgccact gtaatcaaaa    2460
tagttgcaat aataattgaa ataatctcaa ctatgtttca aaaaaaaaa aaaaaaaaa     2520 aaaaaaaa                                                             2528

<210> SEQ ID NO 14
<211> LENGTH: 2424
<212> TYPE: DNA
<213> ORGANISM: Abies grandis

<400> SEQUENCE: 14
gggttatgat cttgtgcatt ctcttaaatc accttatatt gattctagtt acagagaacg      60
cgcggaggtc cttgttagcg agattaaagt gatgcttaat ccagctatta caggagatgg     120
agaatcaatg attactccat ctgcttatga cacagcatgg gtagcgaggg tgcccgccat     180
tgatggctct gctcgcccgc aatttcccca acagttgac tggattttga aaaccagtt      240 aaaagatggt tcatggggaa ttcagtccca cttctgctg tccgaccgtc ttcttgccac      300
tctttcttgt gttcttgtgc tccttaaatg gaacgttggg gatctgcaag tagagcaggg    360
aattgaattc ataaagagca atctggaact agtaaaggat gaaaccgatc aagatagctt    420
ggtaacagac tttgagatca tatttccttc tctgttaaga aagctcaat ctctgcgcct    480 cggacttccc tacgacctgc cttatataca tctgttgcag actaaacggc aggaaagatt    540
agcaaaactt tcaagggagg aaatttatgc ggttccgtcg ccattgttgt attctttaga    600
gggaatacaa gatatagttg aatgggaacg aataatggaa gttcaaagtc aggatgggtc    660
```

```
tttcttaagc tcacctgctt ctactgcctg cgttttcatg cacacaggag acgcgaaatg      720
ccttgaattc ttgaacagtg tgatgatcaa gtttggaaat tttgttccct gcctgtatcc      780
tgtggatctg ctggaacgcc tgttgatcgt agataatatt gtacgccttg aatctatag      840 acactttgaa aaggaaatca aggaagctct tgattatgtt tacaggcatt ggaacgaaag      900
aggaattggg tggggcagac taaatcccat agcagatctt gagaccactg ctttgggatt      960
tcgattgctt cggctgcata ggtacaatgt atctccagcc attttgaca acttcaaaga     1020 tgccaatggg aaattcattt gctcgaccgg tcaattcaac aaagatgtag caagcatgct     1080
gaatctttat agagcttccc agctcgcatt tcccggagaa acattcttg atgaagctaa      1140 aagcttcgct actaaatatt tgagagaagc tcttgagaaa agtgagactt ccagtgcatg     1200
gaacaacaaa caaaacctga gccaagagat caaatacgcg ctgaagactt cttggcatgc     1260
cagtgttccg agagtggaag caaagagata ctgtcaagtg tatcgcccag attatgcacg     1320
catagcaaaa tgcgtttaca agctacccta cgtgaacaat gaaaagtttt tagagctggg     1380
aaaattagat ttcaacatta tccagtccat ccaccaagaa gaaatgaaga atgttaccag     1440
ctggtttaga gattcggggt tgccactatt caccttcgct cgggagaggc cgctggaatt     1500
ctacttctta gtagcggcgg ggacctatga accccagtat gccaaatgca ggttcctctt     1560
tacaaaagtg gcatgcttgc agactgttct ggacgatatg tatgacactt atggaaccct     1620
agatgaattg aagctattca ctgaggctgt gagaagatgg gacctctcct ttacagaaaa     1680
ccttccagac tatatgaaac tatgttacca aatctattat gacatagttc acgaggtggc     1740
ttgggaggca gagaaggaac agggggcgtga attggtcagc ttttttcagaa agggatggga     1800 ggattatctt ctgggttatt atgaagaagc tgaatggtta gctgctgagt atgtgcctac     1860
cttggacgag tacataaaga atggaatcac atctatcggc caacgtatac ttctgttgag     1920
tggagtgttg ataatggatg gcaactcct ttcgcaagag gcattagaga agtagatta     1980 tccaggaaga cgtgttctca cagagctgaa tagcctcatt tcccgcctgg cggatgacac     2040
gaagacatat aaagctgaga aggctcgtgg agaattggcg tccagcattg aatgttacat     2100
gaaagaccat cctgaatgta cagaggaaga ggctctcgat cacatctata gcattctgga     2160
gccggcggtg aaggaactga caagagagtt tctgaagccc gacgacgtcc cattcgcctg     2220
caagaagatg cttttcgagg agacaagagt gacgatggtg atattcaagg atggagatgg     2280
attcggtgtt tccaaattag aagtcaaaga tcatatcaaa gagtgtctca ttgaaccgct     2340
gccactgtaa tcaaaatagt tgcaataata attgaaataa tgtcaactat gtttcacaaa     2400
aaaaaaaaaa aaaaaaaaaa aaaa                                             2424
```

<210> SEQ ID NO 15
<211> LENGTH: 817
<212> TYPE: PRT
<213> ORGANISM: Abies grandis

<400> SEQUENCE: 15

```
Met Ala Gly Val Ser Ala Val Ser Lys Val Ser Ser Leu Val Cys Asp
1               5                   10                  15

Leu Ser Ser Thr Ser Gly Leu Ile Arg Arg Thr Ala Asn Pro His Pro
            20                  25                  30

Asn Val Trp Gly Tyr Asp Leu Val His Ser Leu Lys Ser Pro Tyr Ile
        35                  40                  45

Asp Ser Ser Tyr Arg Glu Arg Ala Glu Val Leu Val Ser Glu Ile Lys
    50                  55                  60
```

-continued

```
Ala Met Leu Asn Pro Ala Ile Thr Gly Asp Gly Glu Ser Met Ile Thr
 65                  70                  75                  80

Pro Ser Ala Tyr Asp Thr Ala Trp Val Ala Arg Val Pro Ala Ile Asp
             85                  90                  95

Gly Ser Ala Arg Pro Gln Phe Pro Gln Thr Val Asp Trp Ile Leu Lys
            100                 105                 110

Asn Gln Leu Lys Asp Gly Ser Trp Gly Ile Gln Ser His Phe Leu Leu
            115                 120                 125

Ser Asp Arg Leu Leu Ala Thr Leu Ser Cys Val Leu Val Leu Leu Lys
            130                 135                 140

Trp Asn Val Gly Asp Leu Gln Val Glu Gln Gly Ile Glu Phe Ile Lys
145                 150                 155                 160

Ser Asn Leu Glu Leu Val Lys Asp Glu Thr Asp Gln Asp Ser Leu Val
                165                 170                 175

Thr Asp Phe Glu Ile Ile Phe Pro Ser Leu Leu Arg Glu Ala Gln Ser
            180                 185                 190

Leu Arg Leu Gly Leu Pro Tyr Asp Leu Pro Tyr Ile His Leu Leu Gln
            195                 200                 205

Thr Lys Arg Gln Glu Arg Leu Ala Lys Leu Ser Arg Glu Glu Ile Tyr
            210                 215                 220

Ala Val Pro Ser Pro Leu Leu Tyr Ser Leu Glu Gly Ile Gln Asp Ile
225                 230                 235                 240

Val Glu Trp Glu Arg Ile Met Glu Val Gln Ser Gln Asp Gly Ser Phe
                245                 250                 255

Leu Ser Ser Pro Ala Ser Thr Ala Cys Val Phe Met His Thr Gly Asp
            260                 265                 270

Ala Lys Cys Leu Glu Phe Leu Asn Ser Val Met Ile Lys Phe Gly Asn
            275                 280                 285

Phe Val Pro Cys Leu Tyr Pro Val Asp Leu Leu Glu Arg Leu Leu Ile
            290                 295                 300

Val Asp Asn Ile Val Arg Leu Gly Ile Tyr Arg His Phe Glu Lys Glu
305                 310                 315                 320

Ile Lys Glu Ala Leu Asp Tyr Val Tyr Arg His Trp Asn Glu Arg Gly
            325                 330                 335

Ile Gly Trp Gly Arg Leu Asn Pro Ile Ala Asp Leu Glu Thr Thr Ala
            340                 345                 350

Leu Gly Phe Arg Leu Leu Arg Leu His Arg Tyr Asn Val Ser Pro Ala
            355                 360                 365

Ile Phe Asp Asn Phe Lys Asp Ala Asn Gly Lys Phe Ile Cys Ser Thr
            370                 375                 380

Gly Gln Phe Asn Lys Asp Val Ala Ser Met Leu Asn Leu Tyr Arg Ala
385                 390                 395                 400

Ser Gln Leu Ala Phe Pro Gly Glu Asn Ile Leu Asp Glu Ala Lys Ser
            405                 410                 415

Phe Ala Thr Lys Tyr Leu Arg Glu Ala Leu Glu Lys Ser Glu Thr Ser
            420                 425                 430

Ser Ala Trp Asn Asn Lys Gln Asn Leu Ser Gln Glu Ile Lys Tyr Ala
            435                 440                 445

Leu Lys Thr Ser Trp His Ala Ser Val Pro Arg Val Glu Ala Lys Arg
            450                 455                 460

Tyr Cys Gln Val Tyr Arg Pro Asp Tyr Ala Arg Ile Ala Lys Cys Val
465                 470                 475                 480
```

```
Tyr Lys Leu Pro Tyr Val Asn Glu Lys Phe Leu Glu Leu Gly Lys
                485                 490                 495

Leu Asp Phe Asn Ile Ile Gln Ser Ile His Gln Glu Met Lys Asn
            500                 505                 510

Val Thr Ser Trp Phe Arg Asp Ser Gly Leu Pro Leu Phe Thr Phe Ala
        515                 520                 525

Arg Glu Arg Pro Leu Glu Phe Tyr Phe Leu Val Ala Ala Gly Thr Tyr
    530                 535                 540

Glu Pro Gln Tyr Ala Lys Cys Arg Phe Leu Phe Thr Lys Val Ala Cys
545                 550                 555                 560

Leu Gln Thr Val Leu Asp Asp Met Tyr Asp Thr Tyr Gly Thr Leu Asp
                565                 570                 575

Glu Leu Lys Leu Phe Thr Glu Ala Val Arg Arg Trp Asp Leu Ser Phe
            580                 585                 590

Thr Glu Asn Leu Pro Asp Tyr Met Lys Leu Cys Tyr Gln Ile Tyr Tyr
        595                 600                 605

Asp Ile Val His Glu Val Ala Trp Glu Ala Glu Lys Glu Gln Gly Arg
    610                 615                 620

Glu Leu Val Ser Phe Phe Arg Lys Gly Trp Glu Asp Tyr Leu Leu Gly
625                 630                 635                 640

Tyr Tyr Glu Glu Ala Glu Trp Leu Ala Ala Glu Tyr Val Pro Thr Leu
                645                 650                 655

Asp Glu Tyr Ile Lys Asn Gly Ile Thr Ser Ile Gly Gln Arg Ile Leu
            660                 665                 670

Leu Leu Ser Gly Val Leu Ile Met Asp Gly Gln Leu Leu Ser Gln Glu
        675                 680                 685

Ala Leu Glu Lys Val Asp Tyr Pro Gly Arg Arg Val Leu Thr Glu Leu
    690                 695                 700

Asn Ser Leu Ile Ser Arg Leu Ala Asp Asp Thr Lys Thr Tyr Lys Ala
705                 710                 715                 720

Glu Lys Ala Arg Gly Glu Leu Ala Ser Ser Ile Glu Cys Tyr Met Lys
                725                 730                 735

Asp His Pro Glu Cys Thr Glu Glu Ala Leu Asp His Ile Tyr Ser
            740                 745                 750

Ile Leu Glu Pro Ala Val Lys Glu Leu Thr Arg Glu Phe Leu Lys Pro
        755                 760                 765

Asp Asp Val Pro Phe Ala Cys Lys Lys Met Leu Phe Glu Glu Thr Arg
    770                 775                 780

Val Thr Met Val Ile Phe Lys Asp Gly Asp Gly Phe Gly Val Ser Lys
785                 790                 795                 800

Leu Glu Val Lys Asp His Ile Lys Glu Cys Leu Ile Glu Pro Leu Pro
                805                 810                 815

Leu

<210> SEQ ID NO 16
<211> LENGTH: 782
<212> TYPE: PRT
<213> ORGANISM: Abies grandis

<400> SEQUENCE: 16

Gly Tyr Asp Leu Val His Ser Leu Lys Ser Pro Tyr Ile Asp Ser Ser
1               5                   10                  15

Tyr Arg Glu Arg Ala Glu Val Leu Val Ser Glu Ile Lys Val Met Leu
            20                  25                  30
```

-continued

```
Asn Pro Ala Ile Thr Gly Asp Gly Glu Ser Met Ile Thr Pro Ser Ala
         35                  40                  45
Tyr Asp Thr Ala Trp Val Ala Arg Val Pro Ala Ile Asp Gly Ser Ala
     50                  55                  60
Arg Pro Gln Phe Pro Gln Thr Val Asp Trp Ile Leu Lys Asn Gln Leu
 65                  70                  75                  80
Lys Asp Gly Ser Trp Gly Ile Gln Ser His Phe Leu Leu Ser Asp Arg
                 85                  90                  95
Leu Leu Ala Thr Leu Ser Cys Val Leu Val Leu Leu Lys Trp Asn Val
             100                 105                 110
Gly Asp Leu Gln Val Glu Gln Gly Ile Glu Phe Ile Lys Ser Asn Leu
         115                 120                 125
Glu Leu Val Lys Asp Glu Thr Asp Gln Asp Ser Leu Val Thr Asp Phe
130                 135                 140
Glu Ile Ile Phe Pro Ser Leu Leu Arg Glu Ala Gln Ser Leu Arg Leu
145                 150                 155                 160
Gly Leu Pro Tyr Asp Leu Pro Tyr Ile His Leu Leu Gln Thr Lys Arg
                165                 170                 175
Gln Glu Arg Leu Ala Lys Leu Ser Arg Glu Glu Ile Tyr Ala Val Pro
             180                 185                 190
Ser Pro Leu Leu Tyr Ser Leu Glu Gly Ile Gln Asp Ile Val Glu Trp
         195                 200                 205
Glu Arg Ile Met Glu Val Gln Ser Gln Asp Gly Ser Phe Leu Ser Ser
         210                 215                 220
Pro Ala Ser Thr Ala Cys Val Phe Met His Thr Gly Asp Ala Lys Cys
225                 230                 235                 240
Leu Glu Phe Leu Asn Ser Val Met Ile Lys Phe Gly Asn Phe Val Pro
                245                 250                 255
Cys Leu Tyr Pro Val Asp Leu Leu Glu Arg Leu Leu Ile Val Asp Asn
             260                 265                 270
Ile Val Arg Leu Gly Ile Tyr Arg His Phe Glu Lys Glu Ile Lys Glu
         275                 280                 285
Ala Leu Asp Tyr Val Tyr Arg His Trp Asn Glu Arg Gly Ile Gly Trp
         290                 295                 300
Gly Arg Leu Asn Pro Ile Ala Asp Leu Glu Thr Thr Ala Leu Gly Phe
305                 310                 315                 320
Arg Leu Leu Arg Leu His Arg Tyr Asn Val Ser Pro Ala Ile Phe Asp
                325                 330                 335
Asn Phe Lys Asp Ala Asn Gly Lys Phe Ile Cys Ser Thr Gly Gln Phe
             340                 345                 350
Asn Lys Asp Val Ala Ser Met Leu Asn Leu Tyr Arg Ala Ser Gln Leu
         355                 360                 365
Ala Phe Pro Gly Glu Asn Ile Leu Asp Glu Ala Lys Ser Phe Ala Thr
         370                 375                 380
Lys Tyr Leu Arg Glu Ala Leu Glu Lys Ser Glu Thr Ser Ser Ala Trp
385                 390                 395                 400
Asn Asn Lys Gln Asn Leu Ser Gln Glu Ile Lys Tyr Ala Leu Lys Thr
                405                 410                 415
Ser Trp His Ala Ser Val Pro Arg Val Glu Ala Lys Arg Tyr Cys Gln
             420                 425                 430
Val Tyr Arg Pro Asp Tyr Ala Arg Ile Ala Lys Cys Val Tyr Lys Leu
         435                 440                 445
```

-continued

| | | | | | | | | | | | | |
|---|---|---|---|---|---|---|---|---|---|---|---|---|
|Pro|Tyr|Val|Asn|Asn|Glu|Lys|Phe|Leu|Glu|Leu|Gly|Lys|Leu|Asp|Phe|
| |450| | | | |455| | | |460| | | | | |

Pro Tyr Val Asn Asn Glu Lys Phe Leu Glu Leu Gly Lys Leu Asp Phe
    450                 455                 460

Asn Ile Ile Gln Ser Ile His Gln Glu Glu Met Lys Asn Val Thr Ser
465                 470                 475                 480

Trp Phe Arg Asp Ser Gly Leu Pro Leu Phe Thr Phe Ala Arg Glu Arg
                485                 490                 495

Pro Leu Glu Phe Tyr Phe Leu Val Ala Ala Gly Thr Tyr Glu Pro Gln
            500                 505                 510

Tyr Ala Lys Cys Arg Phe Leu Phe Thr Lys Val Ala Cys Leu Gln Thr
        515                 520                 525

Val Leu Asp Asp Met Tyr Asp Thr Tyr Gly Thr Leu Asp Glu Leu Lys
530                 535                 540

Leu Phe Thr Glu Ala Val Arg Arg Trp Asp Leu Ser Phe Thr Glu Asn
545                 550                 555                 560

Leu Pro Asp Tyr Met Lys Leu Cys Tyr Gln Ile Tyr Tyr Asp Ile Val
                565                 570                 575

His Glu Val Ala Trp Glu Ala Glu Lys Glu Gln Gly Arg Glu Leu Val
            580                 585                 590

Ser Phe Phe Arg Lys Gly Trp Glu Asp Tyr Leu Leu Gly Tyr Tyr Glu
        595                 600                 605

Glu Ala Glu Trp Leu Ala Ala Glu Tyr Val Pro Thr Leu Asp Glu Tyr
610                 615                 620

Ile Lys Asn Gly Ile Thr Ser Ile Gly Gln Arg Ile Leu Leu Leu Ser
625                 630                 635                 640

Gly Val Leu Ile Met Asp Gly Gln Leu Leu Ser Gln Glu Ala Leu Glu
                645                 650                 655

Lys Val Asp Tyr Pro Gly Arg Arg Val Leu Thr Glu Leu Asn Ser Leu
            660                 665                 670

Ile Ser Arg Leu Ala Asp Asp Thr Lys Thr Tyr Lys Ala Glu Lys Ala
        675                 680                 685

Arg Gly Glu Leu Ala Ser Ser Ile Glu Cys Tyr Met Lys Asp His Pro
690                 695                 700

Glu Cys Thr Glu Glu Glu Ala Leu Asp His Ile Tyr Ser Ile Leu Glu
705                 710                 715                 720

Pro Ala Val Lys Glu Leu Thr Arg Glu Phe Leu Lys Pro Asp Asp Val
                725                 730                 735

Pro Phe Ala Cys Lys Lys Met Leu Phe Glu Glu Thr Arg Val Thr Met
            740                 745                 750

Val Ile Phe Lys Asp Gly Asp Gly Phe Gly Val Ser Lys Leu Glu Val
        755                 760                 765

Lys Asp His Ile Lys Glu Cys Leu Ile Glu Pro Leu Pro Leu
770                 775                 780

<210> SEQ ID NO 17
<211> LENGTH: 1865
<212> TYPE: DNA
<213> ORGANISM: Abies grandis

<400> SEQUENCE: 17

```
atggctgaga tttctgaatc ttccatccct cgacgcacag ggaatcatca cggaaatgtg      60
tgggacgatg acctcataca ctctctcaac tcgccctatg ggcacctgc atattatgag      120
ctccttcaaa agcttattca ggagatcaag catttacttt tgactgaaat ggaaatggat      180
gatggcgatc atgatttaat caaacgtctt cagatcgttg acactttgga atgcctggga      240
```

-continued

```
atcgatagac attttgaaca cgaaatacaa acagctgctt tagattacgt ttacagatgg      300
tggaacgaaa aagtatcgg ggagggatca agagattcct tcagcaaaga tctgaacgct      360
acggctttag gatttcgcgc tctccgactg catcgatata acgtatcgtc aggtgtgttg      420
aagaatttca aggatgaaaa cgggaagttc ttctgcaact ttactggtga agaaggaaga      480
ggagataaac aagtgagaag catgttgtcg ttacttcgag cttcagagat ttcgtttccc      540
ggagaaaaag tgatggaaga ggccaaggca ttcacaagag aatatctaaa ccaagtttta      600
gctggacacg gggatgtgac tgacgtggat caaagccttt tgagagaggt gaagtacgca      660
ttggagtttc catggcattg cagtgtgccg agatgggagg caaggagctt tctcgaaata      720
tatggcacac accattcgtg gctcaagtcg aatatcaacc aaaaaatgtt gaagttagcc      780
aaattggact tcaatattct gcaatgcaaa catcacaagg agatacagtt tattacaagg      840
tggtggagag actcgggtat atcgcagctg aatttctatc gaaagcgaca cgtggaatat      900
tattcttggg ttgttatgtg catttttgag ccagagttct ctgaaagtag aattgccttc      960
gccaaaactg ctatcctgtg tactgttcta gatgacctct atgatacgca cgcaacattg     1020
catgaaatca aaatcatgac agagggagtg agacgatggg atctttcgtt gacagatgac     1080
ctcccagact acattaaaat tgcattccag ttcttcttca atacagtgaa tgaattgata     1140
gttgaaatcg tgaaacggca agggcgggat atgacaacca tagttaaaga ttgctggaag     1200
cgatacattg agtcttatct gcaagaagcg gaatggatag caactggaca tattcccact     1260
tttaacgaat acataaagaa cggcatggct agctcaggga tgtgtattct aaatttgaat     1320
ccacttctct tgttggataa acttctcccc gacaacattc tggagcaaat acattctcca     1380
tccaagatcc tggacctctt agaattgacg ggcagaatcg ccgatgactt aaaagatttc     1440
gaggacgaga aggaacgcgg ggagatggct tcatctttac agtgttatat gaaagaaaat     1500
cctgaatcta cagtggaaaa tgctttaaat cacataaaag gcatccttaa tcgttccctt     1560
gaggaattta attgggagtt tatgaagcag gatagtgtcc caatgtgttg caagaaattc     1620
actttcaata taggtcgagg acttcaattc atctacaaat acagagacgg cttatacatt     1680
tctgacaagg aagtaaagga ccagatattc aaaattctag tccaccaagt tccaatggag     1740
gaatagtgat ggtcttggtt gtagttgtct attatggtat attgcattga catttatgct     1800
taaaggtgtt tcttaaacgt ttagggcgga ccgttaaata agttggcaat aattaatatc     1860
tcgag                                                                 1865
```

<210> SEQ ID NO 18
<211> LENGTH: 581
<212> TYPE: PRT
<213> ORGANISM: Abies grandis

<400> SEQUENCE: 18

```
Met Ala Glu Ile Ser Glu Ser Ser Ile Pro Arg Arg Thr Gly Asn His
 1               5                  10                  15

His Gly Asn Val Trp Asp Asp Leu Ile His Ser Leu Asn Ser Pro
            20                  25                  30

Tyr Gly Ala Pro Ala Tyr Tyr Glu Leu Leu Gln Lys Leu Ile Gln Glu
        35                  40                  45

Ile Lys His Leu Leu Leu Thr Glu Met Glu Met Asp Asp Gly Asp His
    50                  55                  60

Asp Leu Ile Lys Arg Leu Gln Ile Val Asp Thr Leu Glu Cys Leu Gly
65                  70                  75                  80
```

-continued

```
Ile Asp Arg His Phe Glu His Glu Ile Gln Thr Ala Ala Leu Asp Tyr
                 85                  90                  95

Val Tyr Arg Trp Trp Asn Glu Lys Gly Ile Gly Gly Ser Arg Asp
            100                 105                 110

Ser Phe Ser Lys Asp Leu Asn Ala Thr Ala Leu Gly Phe Arg Ala Leu
            115                 120                 125

Arg Leu His Arg Tyr Asn Val Ser Ser Gly Val Leu Lys Asn Phe Lys
130                 135                 140

Asp Glu Asn Gly Lys Phe Phe Cys Asn Phe Thr Gly Glu Glu Gly Arg
145                 150                 155                 160

Gly Asp Lys Gln Val Arg Ser Met Leu Ser Leu Leu Arg Ala Ser Glu
                165                 170                 175

Ile Ser Phe Pro Gly Glu Lys Val Met Glu Glu Ala Lys Ala Phe Thr
            180                 185                 190

Arg Glu Tyr Leu Asn Gln Val Leu Ala Gly His Gly Asp Val Thr Asp
            195                 200                 205

Val Asp Gln Ser Leu Leu Arg Glu Val Lys Tyr Ala Leu Glu Phe Pro
210                 215                 220

Trp His Cys Ser Val Pro Arg Trp Glu Ala Arg Ser Phe Leu Glu Ile
225                 230                 235                 240

Tyr Gly His Asn His Ser Trp Leu Lys Ser Asn Ile Asn Gln Lys Met
                245                 250                 255

Leu Lys Leu Ala Lys Leu Asp Phe Asn Ile Leu Gln Cys Lys His His
            260                 265                 270

Lys Glu Ile Gln Phe Ile Thr Arg Trp Trp Arg Asp Ser Gly Ile Ser
            275                 280                 285

Gln Leu Asn Phe Tyr Arg Lys Arg His Val Glu Tyr Tyr Ser Trp Val
    290                 295                 300

Val Met Cys Ile Phe Glu Pro Glu Phe Ser Glu Ser Arg Ile Ala Phe
305                 310                 315                 320

Ala Lys Thr Ala Ile Leu Cys Thr Val Leu Asp Asp Leu Tyr Asp Thr
                325                 330                 335

His Ala Thr Leu His Glu Ile Lys Ile Met Thr Glu Gly Val Arg Arg
            340                 345                 350

Trp Asp Leu Ser Leu Thr Asp Asp Leu Pro Asp Tyr Ile Lys Ile Ala
            355                 360                 365

Phe Gln Phe Phe Asn Thr Val Asn Glu Leu Ile Val Glu Ile Val
    370                 375                 380

Lys Arg Gln Gly Arg Asp Met Thr Thr Ile Val Lys Asp Cys Trp Lys
385                 390                 395                 400

Arg Tyr Ile Glu Ser Tyr Leu Gln Glu Ala Glu Trp Ile Ala Thr Gly
                405                 410                 415

His Ile Pro Thr Phe Asn Glu Tyr Ile Lys Asn Gly Met Ala Ser Ser
            420                 425                 430

Gly Met Cys Ile Leu Asn Leu Asn Pro Leu Leu Leu Asp Lys Leu
            435                 440                 445

Leu Pro Asp Asn Ile Leu Glu Gln Ile His Ser Pro Ser Lys Ile Leu
    450                 455                 460

Asp Leu Leu Glu Leu Thr Gly Arg Ile Ala Asp Asp Leu Lys Asp Phe
465                 470                 475                 480

Glu Asp Glu Lys Glu Arg Gly Glu Met Ala Ser Ser Leu Gln Cys Tyr
                485                 490                 495
```

```
Met Lys Glu Asn Pro Glu Ser Thr Val Glu Asn Ala Leu Asn His Ile
            500                 505                 510
Lys Gly Ile Leu Asn Arg Ser Leu Glu Glu Phe Asn Trp Glu Phe Met
        515                 520                 525
Lys Gln Asp Ser Val Pro Met Cys Cys Lys Lys Phe Thr Phe Asn Ile
    530                 535                 540
Gly Arg Gly Leu Gln Phe Ile Tyr Lys Tyr Arg Asp Gly Leu Tyr Ile
545                 550                 555                 560
Ser Asp Lys Glu Val Lys Asp Gln Ile Phe Lys Ile Leu Val His Gln
                565                 570                 575
Val Pro Met Glu Glu
            580

<210> SEQ ID NO 19
<211> LENGTH: 1785
<212> TYPE: DNA
<213> ORGANISM: Abies grandis

<400> SEQUENCE: 19
tccatggctc agatttctga atctgtatca ccctctaccg atttgaagag caccgaatct      60
tccattacct ctaatcgaca tggaaatatg tgggaggacg atcgcataca gtctctcaac     120
tcacctatg gggcacctgc atatcaagaa cgcagcgaaa agcttattga agagatcaaa      180
cttttatttt tgagtgacat ggacgatagc tgcaatgata gcgatcgtga tttaatcaaa     240
cgtcttgaga tcgttgatac tgtcgagtgt ctgggaattg atcgacattt tcaacctgag     300
ataaaattag ctctggatta cgtttacaga tgttggaacg aaagaggcat cggagaggga     360
tcaagagatt ccctcaagaa agatctgaac gctacagctt tgggattccg ggctctccga     420
ctccatcgat ataacgtatc ctcaggtgtc ttggagaatt cagagatga taacgggcag     480
ttcttctgcg gttctacagt tgaagaagaa ggagcagaag catataataa acacgtaaga     540
tgcatgctgt cattatcgcg agcttcaaac attttatttc cgggcgaaaa agtgatggaa     600
gaggcgaagg cattcacaac aaattatcta agaaagtttt agcaggacg ggaggctacc      660
cacgtcgatg aaagcctttt gggagaggtg aagtacgcat ggagtttcc atggcattgc      720
agtgtgcaga gatgggaggc aaggagcttt atcgaaatat ttggacaaat tgattcagag     780
cttaagtcga atttgagcaa aaaaatgtta gagttggcga aattggactt caatattctg     840
caatgcacac atcagaaaga actgcagatt atctcaaggt ggttcgcaga ctcaagtata     900
gcatccctga atttctatcg gaaatgttac gtcgaatttt acttttggat ggctgcagcc     960
atctccgagc cggagttttc tggaagcaga gttgccttca caaaaattgc tatactgatg    1020
acaatgctag atgacctgta cgatactcac ggaaccttgg accaactcaa atctttaca     1080
gagggagtga cgatggga tgtttcgttg gtagagggcc tcccagactt catgaaaatt      1140
gcattcgagt tctggttaaa gacatctaat gaattgattg ctgaagctgt taagcgcaa     1200
gggcaagata tggcggccta cataagaaaa aatgcatggg agcgatacct gaagcttat     1260
ctgcaagatg cggaatggat agccactgga catgtcccca cctttgatga gtacttgaat    1320
aatggcacac caaacactgg gatgtgtgta ttgaatttga ttccgcttct gttaatgggt    1380
gaacatttac caatcgacat tctggagcaa atattcttgc cctccaggtt ccaccatctc    1440
attgaattgg cttccaggct cgtcgatgac gcgagagatt tccaggcgga aaggatcat    1500
ggggatttat cgtgtattga gtgttattta aagatcatc ctgagtctac agtagaagat     1560
gcttttaaatc atgttaatgg cctccttggc aattgccttc tggaaatgaa ttggaagttc    1620
```

-continued

```
ttaaagaagc aggacagtgt gccactctcg tgtaagaagt acagcttcca tgtattggca    1680
cgaagcatcc aattcatgta caatcaaggc gatggcttct ccatttcgaa caaagtgatc    1740
aaggatcaag tgcagaaagt tcttattgtc cccgtgccta tttga                   1785
```

<210> SEQ ID NO 20
<211> LENGTH: 593
<212> TYPE: PRT
<213> ORGANISM: Abies grandis

<400> SEQUENCE: 20

```
Met Ala Gln Ile Ser Glu Ser Val Ser Pro Ser Thr Asp Leu Lys Ser
 1               5                  10                  15

Thr Glu Ser Ser Ile Thr Ser Asn Arg His Gly Asn Met Trp Glu Asp
                20                  25                  30

Asp Arg Ile Gln Ser Leu Asn Ser Pro Tyr Gly Ala Pro Ala Tyr Gln
            35                  40                  45

Glu Arg Ser Glu Lys Leu Ile Glu Glu Ile Lys Leu Leu Phe Leu Ser
    50                  55                  60

Asp Met Asp Asp Ser Cys Asn Asp Ser Asp Arg Asp Leu Ile Lys Arg
65                  70                  75                  80

Leu Glu Ile Val Asp Thr Val Glu Cys Leu Gly Ile Asp Arg His Phe
                85                  90                  95

Gln Pro Glu Ile Lys Leu Ala Leu Asp Tyr Val Tyr Arg Cys Trp Asn
            100                 105                 110

Glu Arg Gly Ile Gly Glu Gly Ser Arg Asp Ser Leu Lys Lys Asp Leu
        115                 120                 125

Asn Ala Thr Ala Leu Gly Phe Arg Ala Leu Arg Leu His Arg Tyr Asn
    130                 135                 140

Val Ser Ser Gly Val Leu Glu Asn Phe Arg Asp Asp Asn Gly Gln Phe
145                 150                 155                 160

Phe Cys Gly Ser Thr Val Glu Glu Gly Ala Glu Ala Tyr Asn Lys
                165                 170                 175

His Val Arg Cys Met Leu Ser Leu Ser Arg Ala Ser Asn Ile Leu Phe
            180                 185                 190

Pro Gly Glu Lys Val Met Glu Glu Ala Lys Ala Phe Thr Thr Asn Tyr
        195                 200                 205

Leu Lys Lys Val Leu Ala Gly Arg Glu Ala Thr His Val Asp Glu Ser
    210                 215                 220

Leu Leu Gly Glu Val Lys Tyr Ala Leu Glu Phe Pro Trp His Cys Ser
225                 230                 235                 240

Val Gln Arg Trp Glu Ala Arg Ser Phe Ile Glu Ile Phe Gly Gln Ile
                245                 250                 255

Asp Ser Glu Leu Lys Ser Asn Leu Ser Lys Lys Met Leu Glu Leu Ala
            260                 265                 270

Lys Leu Asp Phe Asn Ile Leu Gln Cys Thr His Gln Lys Glu Leu Gln
        275                 280                 285

Ile Ile Ser Arg Trp Phe Ala Asp Ser Ser Ile Ala Ser Leu Asn Phe
    290                 295                 300

Tyr Arg Lys Cys Tyr Val Glu Phe Tyr Phe Trp Met Ala Ala Ala Ile
305                 310                 315                 320

Ser Glu Pro Glu Phe Ser Gly Ser Arg Val Ala Phe Thr Lys Ile Ala
                325                 330                 335

Ile Leu Met Thr Met Leu Asp Asp Leu Tyr Asp Thr His Gly Thr Leu
            340                 345                 350
```

-continued

| | | | | | | | | | | |
|---|---|---|---|---|---|---|---|---|---|---|
| Asp | Gln | Leu | Lys | Ile | Phe | Thr | Glu | Gly | Val | Arg | Arg | Trp | Asp | Val | Ser |
| | | 355 | | | | 360 | | | | 365 | | | |

Asp Gln Leu Lys Ile Phe Thr Glu Gly Val Arg Arg Trp Asp Val Ser
        355                 360                 365

Leu Val Glu Gly Leu Pro Asp Phe Met Lys Ile Ala Phe Glu Phe Trp
370                 375                 380

Leu Lys Thr Ser Asn Glu Leu Ile Ala Glu Ala Val Lys Ala Gln Gly
385                 390                 395                 400

Gln Asp Met Ala Ala Tyr Ile Arg Lys Asn Ala Trp Glu Arg Tyr Leu
                405                 410                 415

Glu Ala Tyr Leu Gln Asp Ala Glu Trp Ile Ala Thr Gly His Val Pro
            420                 425                 430

Thr Phe Asp Glu Tyr Leu Asn Asn Gly Thr Pro Asn Thr Gly Met Cys
        435                 440                 445

Val Leu Asn Leu Ile Pro Leu Leu Leu Met Gly Glu His Leu Pro Ile
450                 455                 460

Asp Ile Leu Glu Gln Ile Phe Leu Pro Ser Arg Phe His His Leu Ile
465                 470                 475                 480

Glu Leu Ala Ser Arg Leu Val Asp Asp Ala Arg Asp Phe Gln Ala Glu
                485                 490                 495

Lys Asp His Gly Asp Leu Ser Cys Ile Glu Cys Tyr Leu Lys Asp His
            500                 505                 510

Pro Glu Ser Thr Val Glu Asp Ala Leu Asn His Val Asn Gly Leu Leu
        515                 520                 525

Gly Asn Cys Leu Leu Glu Met Asn Trp Lys Phe Leu Lys Lys Gln Asp
    530                 535                 540

Ser Val Pro Leu Ser Cys Lys Lys Tyr Ser Phe His Val Leu Ala Arg
545                 550                 555                 560

Ser Ile Gln Phe Met Tyr Asn Gln Gly Asp Gly Phe Ser Ile Ser Asn
                565                 570                 575

Lys Val Ile Lys Asp Gln Val Gln Lys Val Leu Ile Val Pro Val Pro
            580                 585                 590

Ile

<210> SEQ ID NO 21
<211> LENGTH: 2018
<212> TYPE: DNA
<213> ORGANISM: Abies grandis

<400> SEQUENCE: 21
cagcaatggc tctagtttct accgcaccgt tggcttccaa atcatgcctg cacaaatcgt    60
tgatcagttc tacccatgag cttaaggctc tctctagaac aattccagct ctaggaatga   120
gtaggcgagg gaaatctatc actccttcca tcagcatgag ctctaccacc gttgtaaccg   180
atgatggtgt acgaagacgc atgggcgatt ccattccaa cctctgggac gatgatgtca    240
tacagtcttt accaacggct tatgaggaaa atcgtacct ggagcgtgct gagaaactga    300
tcggggaagt aaagaacatg ttcaattcga tgtcattaga agatggagag ttaatgagtc   360
cgctcaatga tctcattcaa cgcctttgga ttgtcgacag ccttgaacgt ttggggatcc    420
atagacattt caaagatgag ataaaatcgg cgcttgatta tgtttacagt tattggggcg    480
aaaatggcat cggatgcggg agggagagtg ttgttactga tctgaactca actgcgttgg   540
ggcttcgaac cctacgacta cacggatacc cggtgtcttc agatgttttc aaagctttca   600
aaggccaaaa tggcagtttt tcctgctctg aaaatattca gacagatgaa gagatcagag   660
gcgttctgaa tttattccgg gcctccctca ttgcctttcc aggggagaaa attatggatg    720

-continued

```
aggctgaaat cttctctacc aaatatttaa aagaagccct gcaaaagatt ccggtctcca      780
gtctttcgcg agagatcggg gacgttttgg aatatggttg gcacacatat ttgccgcgat      840
tggaagcaag gaattacatc caagtctttg gacaggacac tgagaacacg aagtcatatg      900
tgaagagcaa aaacttttta gaactcgcaa aattggagtt caacatcttt caatccttac      960
aaaagaggga gttagaaagt ctggtcagat ggtggaaaga atcgggtttt cctgagatga     1020
ccttctgccg acatcgtcac gtggaatact acactttggc ttcctgcatt gcgttcgagc     1080
ctcaacattc tggattcaga ctcggctttg ccaagacgtg tcatcttatc acggttcttg     1140
acgatatgta cgacaccttc ggcacagtag acgagctgga actcttcaca gcgacaatga     1200
agagatggga tccgtcctcg atagattgcc ttccagaata tatgaaagga gtgtacatag     1260
cggtttacga caccgtaaat gaaatggctc gagaggcaga ggaggctcaa ggccgagata     1320
cgctcacata tgctcgggaa gcttgggagg cttatattga ttcgtatatg caagaagcaa     1380
ggtggatcgc cactggttac ctgccctcct ttgatgagta ctacgagaat gggaaagtta     1440
gctgtggtca tcgcatatcc gcattgcaac ccattctgac aatggacatc cccttttcctg    1500
atcatatcct caaggaagtt gacttcccat caaagcttaa cgacttggca tgtgccatcc     1560
ttcgattacg aggtgatacg cggtgctaca aggcggacag ggctcgtgga agaagcttt      1620
cctctatatc atgttatatg aaagacaatc ctggagtatc agaggaagat gctctcgatc     1680
atatcaacgc catgatcagt gacgtaatca aaggattaaa ttgggaactt ctcaaaccag     1740
acatcaatgt tcccatctcg gcgaagaaac atgcttttga catcgccaga gctttccatt     1800
acggctacaa ataccgagac ggctacagcg ttgccaacgt tgaaacgaag agtttggtca     1860
cgagaaccct ccttgaatct gtgccttttgt agcaacagct caaatctatg ccctatgcta    1920
tgtcgggtta aaatatatgt ggaaggtagc cgttggatgt agaggataag tttgttataa     1980
tttaataaag ttgtaatttta aaaaaaaaaa aaaaaaaa                            2018
```

<210> SEQ ID NO 22
<211> LENGTH: 628
<212> TYPE: PRT
<213> ORGANISM: Abies grandis

<400> SEQUENCE: 22

```
Met Ala Leu Val Ser Thr Ala Pro Leu Ala Ser Lys Ser Cys Leu His
 1               5                  10                  15

Lys Ser Leu Ile Ser Ser Thr His Glu Leu Lys Ala Leu Ser Arg Thr
            20                  25                  30

Ile Pro Ala Leu Gly Met Ser Arg Arg Gly Lys Ser Ile Thr Pro Ser
        35                  40                  45

Ile Ser Met Ser Ser Thr Thr Val Val Thr Asp Asp Gly Val Arg Arg
    50                  55                  60

Arg Met Gly Asp Phe His Ser Asn Leu Trp Asp Asp Val Ile Gln
 65                  70                  75                  80

Ser Leu Pro Thr Ala Tyr Glu Glu Lys Ser Tyr Leu Glu Arg Ala Glu
                85                  90                  95

Lys Leu Ile Gly Glu Val Lys Asn Met Phe Asn Ser Met Ser Leu Glu
            100                 105                 110

Asp Gly Glu Leu Met Ser Pro Leu Asn Asp Leu Ile Gln Arg Leu Trp
        115                 120                 125

Ile Val Asp Ser Leu Glu Arg Leu Gly Ile His Arg His Phe Lys Asp
    130                 135                 140
```

```
Glu Ile Lys Ser Ala Leu Asp Tyr Val Tyr Ser Tyr Trp Gly Glu Asn
145                 150                 155                 160

Gly Ile Gly Cys Gly Arg Glu Ser Val Thr Asp Leu Asn Ser Thr
            165                 170                 175

Ala Leu Gly Leu Arg Thr Leu Arg Leu His Gly Tyr Pro Val Ser Ser
            180                 185                 190

Asp Val Phe Lys Ala Phe Lys Gly Gln Asn Gly Gln Phe Ser Cys Ser
            195                 200                 205

Glu Asn Ile Gln Thr Asp Glu Ile Arg Gly Val Leu Asn Leu Phe
            210                 215                 220

Arg Ala Ser Leu Ile Ala Phe Pro Gly Glu Lys Ile Met Asp Glu Ala
225                 230                 235                 240

Glu Ile Phe Ser Thr Lys Tyr Leu Lys Glu Ala Leu Gln Lys Ile Pro
            245                 250                 255

Val Ser Ser Leu Ser Arg Glu Ile Gly Asp Val Leu Glu Tyr Gly Trp
            260                 265                 270

His Thr Tyr Leu Pro Arg Leu Glu Ala Arg Asn Tyr Ile Gln Val Phe
        275                 280                 285

Gly Gln Asp Thr Glu Asn Thr Lys Ser Tyr Val Lys Ser Lys Lys Leu
        290                 295                 300

Leu Glu Leu Ala Lys Leu Glu Phe Asn Ile Phe Gln Ser Leu Gln Lys
305                 310                 315                 320

Arg Glu Leu Glu Ser Leu Val Arg Trp Trp Lys Glu Ser Gly Phe Pro
            325                 330                 335

Glu Met Thr Phe Cys Arg His Arg Val Glu Tyr Tyr Thr Leu Ala
            340                 345                 350

Ser Cys Ile Ala Phe Glu Pro Gln His Ser Gly Phe Arg Leu Gly Phe
        355                 360                 365

Ala Lys Thr Cys His Leu Ile Thr Val Leu Asp Asp Met Tyr Asp Thr
        370                 375                 380

Phe Gly Thr Val Asp Glu Leu Glu Leu Phe Thr Ala Thr Met Lys Arg
385                 390                 395                 400

Trp Asp Pro Ser Ser Ile Asp Cys Leu Pro Glu Tyr Met Lys Gly Val
            405                 410                 415

Tyr Ile Ala Val Tyr Asp Thr Val Asn Glu Met Ala Arg Glu Ala Glu
            420                 425                 430

Glu Ala Gln Gly Arg Asp Thr Leu Thr Tyr Ala Arg Glu Ala Trp Glu
        435                 440                 445

Ala Tyr Ile Asp Ser Tyr Met Gln Glu Ala Arg Trp Ile Ala Thr Gly
        450                 455                 460

Tyr Leu Pro Ser Phe Asp Glu Tyr Tyr Glu Asn Gly Lys Val Ser Cys
465                 470                 475                 480

Gly His Arg Ile Ser Ala Leu Gln Pro Ile Leu Thr Met Asp Ile Pro
            485                 490                 495

Phe Pro Asp His Ile Leu Lys Glu Val Asp Phe Pro Ser Lys Leu Asn
            500                 505                 510

Asp Leu Ala Cys Ala Ile Leu Arg Leu Arg Gly Asp Thr Arg Cys Tyr
            515                 520                 525

Lys Ala Asp Arg Ala Arg Gly Glu Glu Ala Ser Ser Ile Ser Cys Tyr
        530                 535                 540

Met Lys Asp Asn Pro Gly Val Ser Glu Glu Asp Ala Leu Asp His Ile
545                 550                 555                 560
```

-continued

```
Asn Ala Met Ile Ser Asp Val Ile Lys Gly Leu Asn Trp Glu Leu Leu
                565                 570                 575

Lys Pro Asp Ile Asn Val Pro Ile Ser Ala Lys Lys His Ala Phe Asp
            580                 585                 590

Ile Ala Arg Ala Phe His Tyr Gly Tyr Lys Tyr Arg Asp Gly Tyr Ser
        595                 600                 605

Val Ala Asn Val Glu Thr Lys Ser Leu Val Thr Arg Thr Leu Leu Glu
    610                 615                 620

Ser Val Pro Leu
625
```

<210> SEQ ID NO 23
<211> LENGTH: 2089
<212> TYPE: DNA
<213> ORGANISM: Abies grandis

<400> SEQUENCE: 23

| | | | | | |
|---|---|---|---|---|---|
| tgccgtttaa | tcggtttaaa | gaagctacca | tagttcggtt | taaagaagct | accatagttt | 60 |
| aggcaggaat | ccatggctct | cctttctatc | gtatctttgc | aggttcccaa | atcctgcggg | 120 |
| ctgaaatcgt | tgatcagttc | cagcaatgtg | cagaaggctc | tctgtatctc | tacagcagtc | 180 |
| ccaacactca | gaatgcgtag | gcgacagaaa | gctctggtca | tcaacatgaa | attgaccact | 240 |
| gtatcccatc | gtgatgataa | tggtggtggt | gtactgcaaa | gacgcatagc | cgatcatcat | 300 |
| cccaacctgt | gggaagatga | tttcatacaa | tcattgtcct | caccttatgg | gggatcttcg | 360 |
| tacagtgaac | gtgctgagac | agtcgttgag | gaagtaaaag | agatgttcaa | ttcaatacca | 420 |
| aataatagag | aattatttgg | ttcccaaaat | gatctcctta | cacgcctttg | gatggtggat | 480 |
| agcattgaac | gtctggggat | agatagacat | tccaaaatg | agataagagt | agccctcgat | 540 |
| tatgtttaca | gttattggaa | ggaaaaggaa | ggcattgggt | gtggcagaga | ttctactttt | 600 |
| cctgatctca | actcgactgc | cttggcgctt | cgaactcttc | gactgcacgg | atacaatgtg | 660 |
| tcttcagatg | tgctggaata | cttcaaagat | gaaaaggggc | attttgcctg | ccctgcaatc | 720 |
| ctaaccgagg | gacagatcac | tagaagtgtt | ctaaatttat | atcgggcttc | cctggtcgcc | 780 |
| tttcccgggg | agaaagttat | ggaagaggct | gaaatcttct | cggcatctta | tttgaaaaaa | 840 |
| gtcttacaaa | agattccggt | ctccaatctt | tcaggagaga | tagaatatgt | tttgaatat | 900 |
| ggttggcaca | cgaatttgcc | gagattggaa | gcaagaaatt | atatcgaggt | ctacgagcag | 960 |
| agcggctatg | aaagcttaaa | cgagatgcca | tatatgaaca | tgaagaagct | tttacaactt | 1020 |
| gcaaaattgg | agttcaatat | ctttcactct | ttgcaactaa | gagagttaca | atctatctcc | 1080 |
| agatggtgga | agaatcagg | ttcgtctcaa | ctgacttta | cacggcatcg | tcacgtggaa | 1140 |
| tactacacta | tggcatcttg | catttctatg | ttgccaaaac | attcagcttt | cagaatggag | 1200 |
| tttgtcaaag | tgtgtcatct | tgtaacagtt | ctcgatgata | tatatgacac | ttttggaaca | 1260 |
| atgaacgaac | tccaactttt | tacggatgca | attaagagat | gggatttgtc | aacgacaagg | 1320 |
| tggcttccag | aatatatgaa | aggagtgtac | atggacttgt | atcaatgcat | taatgaaatg | 1380 |
| gtggaagagg | ctgagaagac | tcaaggccga | gatatgctca | actatattca | aaatgcttgg | 1440 |
| gaagccctat | ttgatacctt | tatgcaagaa | gcaaagtgga | tctccagcag | ttatctccca | 1500 |
| acgtttgagg | agtacttgaa | gaatgcaaaa | gttagttctg | gttctcgcat | agccacatta | 1560 |
| caacccattc | tcactttgga | tgtaccactt | cctgattaca | tactgcaaga | aattgattat | 1620 |
| ccatccagat | tcaatgagtt | agcttcgtcc | atccttcgac | tacgaggtga | cacgcgctgc | 1680 |

-continued

```
tacaaggcgg atagggcccg tggagaagaa gcttcagcta tatcgtgtta tatgaaagac    1740
catcctggat caatagagga agatgctctc aatcatatca acgccatgat cagtgatgca    1800
atcagagaat taaattggga gcttctcaga ccggatagca aaagtcccat ctcttccaag    1860
aaacatgctt ttgacatcac cagagctttc catcatgtct acaaatatcg agatggttac    1920 actgttttcca acaacgaaac aaagaatttg gtgatgaaaa ccgttcttga acctctcgct    1980
ttgtaaaaac atatagaatg cattaaaatg tgggaagtct ataatctaga ctattctcta    2040
tctttcataa tgtagatctg gatgtgtatt gaactctaaa aaaaaaaaa                2089
```

<210> SEQ ID NO 24
<211> LENGTH: 637
<212> TYPE: PRT
<213> ORGANISM: Abies grandis

<400> SEQUENCE: 24

```
Met Ala Leu Leu Ser Ile Val Ser Leu Gln Val Pro Lys Ser Cys Gly
1               5                   10                  15

Leu Lys Ser Leu Ile Ser Ser Ser Asn Val Gln Lys Ala Leu Cys Ile
            20                  25                  30

Ser Thr Ala Val Pro Thr Leu Arg Met Arg Arg Gln Lys Ala Leu
        35                  40                  45

Val Ile Asn Met Lys Leu Thr Thr Val Ser His Arg Asp Asp Asn Gly
50                  55                  60

Gly Gly Val Leu Gln Arg Arg Ile Ala Asp His His Pro Asn Leu Trp
65                  70                  75                  80

Glu Asp Asp Phe Ile Gln Ser Leu Ser Ser Pro Tyr Gly Gly Ser Ser
                85                  90                  95

Tyr Ser Glu Arg Ala Glu Thr Val Val Glu Val Lys Glu Met Phe
            100                 105                 110

Asn Ser Ile Pro Asn Asn Arg Glu Leu Phe Gly Ser Gln Asn Asp Leu
        115                 120                 125

Leu Thr Arg Leu Trp Met Val Asp Ser Ile Glu Arg Leu Gly Ile Asp
130                 135                 140

Arg His Phe Gln Asn Glu Ile Arg Val Ala Leu Asp Tyr Val Tyr Ser
145                 150                 155                 160

Tyr Trp Lys Glu Lys Glu Gly Ile Gly Cys Gly Arg Asp Ser Thr Phe
                165                 170                 175

Pro Asp Leu Asn Ser Thr Ala Leu Ala Leu Arg Thr Leu Arg Leu His
            180                 185                 190

Gly Tyr Asn Val Ser Ser Asp Val Leu Glu Tyr Phe Lys Asp Glu Lys
        195                 200                 205

Gly His Phe Ala Cys Pro Ala Ile Leu Thr Glu Gly Gln Ile Thr Arg
    210                 215                 220

Ser Val Leu Asn Leu Tyr Arg Ala Ser Leu Val Ala Phe Pro Gly Glu
225                 230                 235                 240

Lys Val Met Glu Glu Ala Glu Ile Phe Ser Ala Ser Tyr Leu Lys Lys
                245                 250                 255

Val Leu Gln Lys Ile Pro Val Ser Asn Leu Ser Gly Glu Ile Glu Tyr
            260                 265                 270

Val Leu Glu Tyr Gly Trp His Thr Asn Leu Pro Arg Leu Glu Ala Arg
        275                 280                 285

Asn Tyr Ile Glu Val Tyr Glu Gln Ser Gly Tyr Glu Ser Leu Asn Glu
    290                 295                 300
```

```
Met Pro Tyr Met Asn Met Lys Lys Leu Leu Gln Leu Ala Lys Leu Glu
305                 310                 315                 320

Phe Asn Ile Phe His Ser Leu Gln Leu Arg Glu Leu Gln Ser Ile Ser
            325                 330                 335

Arg Trp Trp Lys Glu Ser Gly Ser Ser Gln Leu Thr Phe Thr Arg His
            340                 345                 350

Arg His Val Glu Tyr Tyr Thr Met Ala Ser Cys Ile Ser Met Leu Pro
            355                 360                 365

Lys His Ser Ala Phe Arg Met Glu Phe Val Lys Val Cys His Leu Val
            370                 375                 380

Thr Val Leu Asp Asp Ile Tyr Asp Thr Phe Gly Thr Met Asn Glu Leu
385                 390                 395                 400

Gln Leu Phe Thr Asp Ala Ile Lys Arg Trp Asp Leu Ser Thr Thr Arg
            405                 410                 415

Trp Leu Pro Glu Tyr Met Lys Gly Val Tyr Met Asp Leu Tyr Gln Cys
            420                 425                 430

Ile Asn Glu Met Val Glu Glu Ala Glu Lys Thr Gln Gly Arg Asp Met
            435                 440                 445

Leu Asn Tyr Ile Gln Asn Ala Trp Glu Ala Leu Phe Asp Thr Phe Met
450                 455                 460

Gln Glu Ala Lys Trp Ile Ser Ser Tyr Leu Pro Thr Phe Glu Glu
465                 470                 475                 480

Tyr Leu Lys Asn Ala Lys Val Ser Ser Gly Ser Arg Ile Ala Thr Leu
            485                 490                 495

Gln Pro Ile Leu Thr Leu Asp Val Pro Leu Pro Asp Tyr Ile Leu Gln
            500                 505                 510

Glu Ile Asp Tyr Pro Ser Arg Phe Asn Glu Leu Ala Ser Ser Ile Leu
            515                 520                 525

Arg Leu Arg Gly Asp Thr Arg Cys Tyr Lys Ala Asp Arg Ala Arg Gly
530                 535                 540

Glu Glu Ala Ser Ala Ile Ser Cys Tyr Met Lys Asp His Pro Gly Ser
545                 550                 555                 560

Ile Glu Glu Asp Ala Leu Asn His Ile Asn Ala Met Ile Ser Asp Ala
                565                 570                 575

Ile Arg Glu Leu Asn Trp Glu Leu Leu Arg Pro Asp Ser Lys Ser Pro
            580                 585                 590

Ile Ser Ser Lys Lys His Ala Phe Asp Ile Thr Arg Ala Phe His His
            595                 600                 605

Val Tyr Lys Tyr Arg Asp Gly Tyr Thr Val Ser Asn Asn Glu Thr Lys
            610                 615                 620

Asn Leu Val Met Lys Thr Val Leu Glu Pro Leu Ala Leu
625                 630                 635
```

<210> SEQ ID NO 25
<211> LENGTH: 2196
<212> TYPE: DNA
<213> ORGANISM: Abies grandis

<400> SEQUENCE: 25

| | | | | |
|---|---|---|---|---|
| tgccggcacg aggttatctt gagcttcctc catataggcc aacacatatc atatcaaagg | 60 |
| gagcaagaat ggctctggtt tctatctcac cgttggcttc gaaatcttgc ctgcgcaagt | 120 |
| cgttgatcag ttcaattcat gaacataagc ctccctatag aacaatccca aatcttggaa | 180 |
| tgcgtaggcg agggaaatct gtcacgcctt ccatgagcat cagtttggcc accgctgcac | 240 |

-continued

```
ctgatgatgg tgtacaaaga cgcataggtg actaccattc caatatctgg gacgatgatt      300
tcatacagtc tctatcaacg ccttatgggg aaccctctta ccaggaacgt gctgagagat      360
taattgtgga ggtaaagaag atattcaatt caatgtacct ggatgatgga agattaatga      420
gttcctttaa tgatctcatg caacgccttt ggatagtcga tagcgttgaa cgtttgggga      480
tagctagaca tttcaagaac gagataacat cagctctgga ttatgttttc cgttactggg      540
aggaaaacgg cattggatgt gggagagaca gtattgttac tgatctcaac tcaactgcgt      600
tggggtttcg aactcttcga ttacacgggt acactgtatc tccagaggtt ttaaaagctt      660
ttcaagatca aaatggacag tttgtatgct cccccggtca gacagagggt gagatcagaa      720
gcgttcttaa cttatatcgg gcttccctca ttgccttccc tggtgagaaa gttatggaag      780
aagctgaaat cttctccaca agatatttga agaagctct acaaaagatt ccagtctccg      840
ctctttcaca agagataaag tttgttatgg aatatggctg gcacacaaat ttgccaagat      900
tggaagcaag aaattacata gacacacttg agaaagacac cagtgcatgg ctcaataaaa      960
atgctgggaa gaagctttta gaacttgcaa aattggagtt caatatattt aactccttac     1020
aacaaaagga attacaatat cttttgagat ggtggaaaga gtcggatttg cctaaattga     1080
catttgctcg gcatcgtcat gtggaattct acactttggc ctcttgtatt gccattgacc     1140
caaaacattc tgcattcaga ctaggcttcg ccaaaatgtg tcatcttgtc acagttttgg     1200
acgatattta cgacactttt ggaacgattg acgagcttga actcttcaca tctgcaatta     1260
agagatggaa ttcatcagag atagaacacc ttccagaata tatgaaatgt gtgtacatgg     1320
tcgtgtttga aactgtaaat gaactgacac gagaggcgga gaagactcaa gggagaaaca     1380
ctctcaacta tgttcgaaag gcttgggagg cttattttga ttcatatatg gaagaagcaa     1440
aatggatctc taatggttat ctgccaatgt ttgaagagta ccatgagaat gggaaagtga     1500
gctctgcata tcgcgtagca acattgcaac ccatcctcac tttgaatgca tggcttcctg     1560
attacatctt gaagggaatt gattttccat ccaggttcaa tgatttggca tcgtccttcc     1620
ttcggctacg aggtgacaca cgctgctaca aggccgatag ggatcgtggt gaagaagctt     1680
cgtgtatatc atgttatatg aaagacaatc ctggatcaac cgaagaagat gccctcaatc     1740
atatcaatgc catggtcaat gacataatca agaattaaa ttgggaactt ctaagatcca     1800
acgacaatat tccaatgctg gccaagaaac atgcttttga cataacaaga gctctccacc     1860
atctctacat atatcgagat ggctttagtg ttgccaacaa ggaaacaaaa aaattggtta     1920
tggaaacact ccttgaatct atgcttttt aactataacc atatccataa taataagctc     1980
ataatgctaa attattggcc ttatgacata gtttatgtat gtacttgtgt gaattcaatc     2040
atatcgtgtg gtatgattaa aaagctaga gcttactagg ttagtaacat ggtgataaaa     2100
gttataaaat gtgagttata gagataccca tgttgaataa tgaattacaa aaagagaaat     2160
ttatgtagaa taagattgga agcttttcaa ttgttt                                2196
```

<210> SEQ ID NO 26
<211> LENGTH: 627
<212> TYPE: PRT
<213> ORGANISM: Abies grandis

<400> SEQUENCE: 26

```
Met Ala Leu Val Ser Ile Ser Pro Leu Ala Ser Lys Ser Cys Leu Arg
 1               5                  10                  15

Lys Ser Leu Ile Ser Ser Ile His Glu His Lys Pro Pro Tyr Arg Thr
             20                  25                  30
```

-continued

```
Ile Pro Asn Leu Gly Met Arg Arg Gly Lys Ser Val Thr Pro Ser
        35                  40                  45

Met Ser Ile Ser Leu Ala Thr Ala Ala Pro Asp Asp Gly Val Gln Arg
    50                  55                  60

Arg Ile Gly Asp Tyr His Ser Asn Ile Trp Asp Asp Phe Ile Gln
65                  70                  75                  80

Ser Leu Ser Thr Pro Tyr Gly Glu Pro Ser Tyr Gln Glu Arg Ala Glu
                85                  90                  95

Arg Leu Ile Val Glu Val Lys Lys Ile Phe Asn Ser Met Tyr Leu Asp
                100                 105                 110

Asp Gly Arg Leu Met Ser Ser Phe Asn Asp Leu Met Gln Arg Leu Trp
            115                 120                 125

Ile Val Asp Ser Val Glu Arg Leu Gly Ile Ala Arg His Phe Lys Asn
130                 135                 140

Glu Ile Thr Ser Ala Leu Asp Tyr Val Phe Arg Tyr Trp Glu Glu Asn
145                 150                 155                 160

Gly Ile Gly Cys Gly Arg Asp Ser Ile Val Thr Asp Leu Asn Ser Thr
                165                 170                 175

Ala Leu Gly Phe Arg Thr Leu Arg Leu His Gly Tyr Thr Val Ser Pro
            180                 185                 190

Glu Val Leu Lys Ala Phe Gln Asp Gln Asn Gly Gln Phe Val Cys Ser
            195                 200                 205

Pro Gly Gln Thr Glu Gly Glu Ile Arg Ser Val Leu Asn Leu Tyr Arg
    210                 215                 220

Ala Ser Leu Ile Ala Phe Pro Gly Glu Lys Val Met Glu Glu Ala Glu
225                 230                 235                 240

Ile Phe Ser Thr Arg Tyr Leu Lys Glu Ala Leu Gln Lys Ile Pro Val
                245                 250                 255

Ser Ala Leu Ser Gln Glu Ile Lys Phe Val Met Glu Tyr Gly Trp His
            260                 265                 270

Thr Asn Leu Pro Arg Leu Glu Ala Arg Asn Tyr Ile Asp Thr Leu Glu
    275                 280                 285

Lys Asp Thr Ser Ala Trp Leu Asn Lys Asn Ala Gly Lys Lys Leu Leu
290                 295                 300

Glu Leu Ala Lys Leu Glu Phe Asn Ile Phe Asn Ser Leu Gln Gln Lys
305                 310                 315                 320

Glu Leu Gln Tyr Leu Leu Arg Trp Trp Lys Glu Ser Asp Leu Pro Lys
                325                 330                 335

Leu Thr Phe Ala Arg His Arg His Val Glu Phe Tyr Thr Leu Ala Ser
            340                 345                 350

Cys Ile Ala Ile Asp Pro Lys His Ser Ala Phe Arg Leu Gly Phe Ala
            355                 360                 365

Lys Met Cys His Leu Val Thr Val Leu Asp Asp Ile Tyr Asp Thr Phe
    370                 375                 380

Gly Thr Ile Asp Glu Leu Glu Leu Phe Thr Ser Ala Ile Lys Arg Trp
385                 390                 395                 400

Asn Ser Ser Glu Ile Glu His Leu Pro Glu Tyr Met Lys Cys Val Tyr
                405                 410                 415

Met Val Val Phe Glu Thr Val Asn Glu Leu Thr Arg Glu Ala Glu Lys
            420                 425                 430

Thr Gln Gly Arg Asn Thr Leu Asn Tyr Val Arg Lys Ala Trp Glu Ala
            435                 440                 445
```

```
Tyr Phe Asp Ser Tyr Met Glu Glu Ala Lys Trp Ile Ser Asn Gly Tyr
    450                 455                 460

Leu Pro Met Phe Glu Glu Tyr His Glu Asn Gly Lys Val Ser Ser Ala
465                 470                 475                 480

Tyr Arg Val Ala Thr Leu Gln Pro Ile Leu Thr Leu Asn Ala Trp Leu
                485                 490                 495

Pro Asp Tyr Ile Leu Lys Gly Ile Asp Phe Pro Ser Arg Phe Asn Asp
            500                 505                 510

Leu Ala Ser Ser Phe Leu Arg Leu Arg Gly Asp Thr Arg Cys Tyr Lys
            515                 520                 525

Ala Asp Arg Asp Arg Gly Glu Ala Ser Cys Ile Ser Cys Tyr Met
    530                 535                 540

Lys Asp Asn Pro Gly Ser Thr Glu Glu Asp Ala Leu Asn His Ile Asn
545                 550                 555                 560

Ala Met Val Asn Asp Ile Ile Lys Glu Leu Asn Trp Glu Leu Leu Arg
                565                 570                 575

Ser Asn Asp Asn Ile Pro Met Leu Ala Lys Lys His Ala Phe Asp Ile
            580                 585                 590

Thr Arg Ala Leu His His Leu Tyr Ile Tyr Arg Asp Gly Phe Ser Val
    595                 600                 605

Ala Asn Lys Glu Thr Lys Lys Leu Val Met Glu Thr Leu Leu Glu Ser
610                 615                 620

Met Leu Phe
625

<210> SEQ ID NO 27
<211> LENGTH: 2429
<212> TYPE: DNA
<213> ORGANISM: Abies grandis

<400> SEQUENCE: 27
attaaagaag ctaccatagt ttaggcagga atgcatggct ctcctttcta tcgtatcttt       60
gcaggttccc aaatcctgcg ggctgaaatc gttgatcagt tccagcaatg tgcagaaggc      120
tctctgtatc tctacagcag tcccaactct cagaatgcgt aggcgacaga aagctctggt      180
catcaacatg aaattgacca ctgtatccca tcgtgatgat aatggtggtg gtgtactgca      240
aagacgcata gccgatcatc atcccaacct gtgggaagat gatttcatac aatcattgtc      300
ctcaccttat gggggatctt cgtacagtga acgtgctgtg acagtggttg aggaagtaaa      360
agagatgttc aattcaatac caaataatag agaattattt ggttcccaaa atgatctcct      420
tacacgcctt tggatggtgg atagcattga acgtctgggg atagatagac atttccaaaa      480
tgagataaga gtagccctcg attatgttta cagttattgg aaggaaaagg aaggcattgg      540
gtgtggcaga gattctactt ttcctgatct caactcgact gctctggcgc ttcgaactct      600
tcgactgcac ggatacaatg tgtcttcaga gtgctggaa tacttcaaag atcaaagggg      660
gcattttgcc tgccctgcaa tcctaaccga gggacagatc actagaagtg ttctaaattt      720
atatcgggct tccctggtcg cctttccggg ggagaaagtt atggaagagg ctgaaatctt      780
ctcggcatct tatttgaaag aagtcttaca aaagattcca gtctccagtt tttcacgaga      840
gatagaatac gttttggaat atggttggca cacaaatttg ccaagattgg aagcaagaaa      900
ttatatcgac gtctacgggc aggacagcta tgaaagttca acgagatgc catatgtgaa      960 tacgcagaag ctttttaaaac ttgcaaaatt ggagtttaat atctttcact ctttgcaaca     1020
gaaagagttg caatatatct ctagatggtg gaaagattcg tgttcatctc atctgacttt     1080
```

```
tactcgacac cgtcacgtgg aatactacac aatggcatct tgcatttcta tggagccgaa    1140
acactccgct ttcagattgg ggtttgtcaa aacatgtcat cttctaacag ttctggatga    1200
tatgtatgac acttttggaa cactggacga actccaactt tttacgactg cctttaagag    1260
atgggatttg tcagagacaa agtgtcttcc agaatatatg aaagcagtgt acatggactt    1320
gtatcaatgt cttaatgaat tggcgcaaga ggctgagaag actcaaggca gagatacgct    1380
caactatatt cgcaatgctt atgagtctca ttttgattcg tttatgcacg aagcaaaatg    1440
gatctcaagt ggttatctcc caacgtttga ggagtacttg aagaatggga agttagttc    1500 cggttctcgc acagccactt tacaacccat actcaccttg gatgtaccac ttcctaatta    1560
catactgcaa gaaattgatt atccatctag gttcaatgac ttggcttcgt ccctccttcg    1620
gctacgtggt gacacgcgct gctacaaggc ggatagggct cgtggagaag aagcttcagc    1680
tatatcgtgt tatatgaaag accatcctgg atcaacagag gaagatgctc tcaatcatat    1740
caacgtcatg atcagtgatg caatcagaga attaaattgg gagcttctca gaccagatag    1800
caaaagtccc atctcttcca agaaacatgc ttttgacatc accagagctt ccatcacct    1860 ctacaagtac cgagatggtt acactgttgc gagtagtgaa acaaagaatt tggtgatgaa    1920
aacagttctt gaacctgtgg cattgtaaaa aaatatcaac cgcatcaaaa tgcacggagt    1980
ttgtaattta atgcacttct cttataatac acttctcttt agacctgtag tgaagccgat    2040
gcaccattac agtgtatatg ggagccagtc tagtctcaaa aagtttgtaa atgttattct    2100
atgatatact ctttagacca aaagctagat gcccatgaaa agcaagtgtt ttagaattgc    2160
ttctggattt gcttaaattt tctccatgat tctttagaaa tgttgcatcc ccaaacttca    2220
ctgccatata agataacggg agtgacaagg attttaaaga ggatttttt ttatgtcccg    2280 catcacaagg tttgtcgatt tacagttgtt ttcaagactg aagtaggatt tccaccctcc    2340
attaatcctc ttctcgatgt tatagtttca cttgagcttg tgatggaagt caattcctag    2400
atatttataa gaaaaaaaaa aaaaaaaaa                                       2429
```

<210> SEQ ID NO 28
<211> LENGTH: 637
<212> TYPE: PRT
<213> ORGANISM: Abies grandis

<400> SEQUENCE: 28

```
Met Ala Leu Leu Ser Ile Val Ser Leu Gln Val Pro Lys Ser Cys Gly
1               5                   10                  15

Leu Lys Ser Leu Ile Ser Ser Ser Asn Val Gln Lys Ala Leu Cys Ile
            20                  25                  30

Ser Thr Ala Val Pro Thr Leu Arg Met Arg Arg Gln Lys Ala Leu
        35                  40                  45

Val Ile Asn Met Lys Leu Thr Thr Val Ser His Arg Asp Asp Asn Gly
    50                  55                  60

Gly Gly Val Leu Gln Arg Arg Ile Ala Asp His His Pro Asn Leu Trp
65                  70                  75                  80

Glu Asp Asp Phe Ile Gln Ser Leu Ser Ser Pro Tyr Gly Gly Ser Ser
                85                  90                  95

Tyr Ser Glu Arg Ala Val Thr Val Val Glu Glu Val Lys Glu Met Phe
            100                 105                 110

Asn Ser Ile Pro Asn Asn Arg Glu Leu Phe Gly Ser Gln Asn Asp Leu
        115                 120                 125
```

-continued

```
Leu Thr Arg Leu Trp Met Val Asp Ser Ile Glu Arg Leu Gly Ile Asp
130                 135                 140

Arg His Phe Gln Asn Glu Ile Arg Val Ala Leu Asp Tyr Val Tyr Ser
145                 150                 155                 160

Tyr Trp Lys Glu Lys Glu Gly Ile Gly Cys Gly Arg Asp Ser Thr Phe
                165                 170                 175

Pro Asp Leu Asn Ser Thr Ala Leu Ala Leu Arg Thr Leu Arg Leu His
                180                 185                 190

Gly Tyr Asn Val Ser Ser Asp Val Leu Glu Tyr Phe Lys Asp Gln Lys
                195                 200                 205

Gly His Phe Ala Cys Pro Ala Ile Leu Thr Glu Gly Gln Ile Thr Arg
210                 215                 220

Ser Val Leu Asn Leu Tyr Arg Ala Ser Leu Val Ala Phe Pro Gly Glu
225                 230                 235                 240

Lys Val Met Glu Glu Ala Glu Ile Phe Ser Ala Ser Tyr Leu Lys Glu
                245                 250                 255

Val Leu Gln Lys Ile Pro Val Ser Ser Phe Ser Arg Glu Ile Glu Tyr
                260                 265                 270

Val Leu Glu Tyr Gly Trp His Thr Asn Leu Pro Arg Leu Glu Ala Arg
                275                 280                 285

Asn Tyr Ile Asp Val Tyr Gly Gln Asp Ser Tyr Glu Ser Ser Asn Glu
290                 295                 300

Met Pro Tyr Val Asn Thr Gln Lys Leu Leu Lys Leu Ala Lys Leu Glu
305                 310                 315                 320

Phe Asn Ile Phe His Ser Leu Gln Gln Lys Glu Leu Gln Tyr Ile Ser
                325                 330                 335

Arg Trp Trp Lys Asp Ser Cys Ser Ser His Leu Thr Phe Thr Arg His
                340                 345                 350

Arg His Val Glu Tyr Tyr Thr Met Ala Ser Cys Ile Ser Met Glu Pro
                355                 360                 365

Lys His Ser Ala Phe Arg Leu Gly Phe Val Lys Thr Cys His Leu Leu
                370                 375                 380

Thr Val Leu Asp Asp Met Tyr Asp Thr Phe Gly Thr Leu Asp Glu Leu
385                 390                 395                 400

Gln Leu Phe Thr Thr Ala Phe Lys Arg Trp Asp Leu Ser Glu Thr Lys
                405                 410                 415

Cys Leu Pro Glu Tyr Met Lys Ala Val Tyr Met Asp Leu Tyr Gln Cys
                420                 425                 430

Leu Asn Glu Leu Ala Gln Glu Ala Lys Thr Gln Gly Arg Asp Thr
                435                 440                 445

Leu Asn Tyr Ile Arg Asn Ala Tyr Glu Ser His Phe Asp Ser Phe Met
                450                 455                 460

His Glu Ala Lys Trp Ile Ser Ser Gly Tyr Leu Pro Thr Phe Glu Glu
465                 470                 475                 480

Tyr Leu Lys Asn Gly Lys Val Ser Ser Gly Ser Arg Thr Ala Thr Leu
                485                 490                 495

Gln Pro Ile Leu Thr Leu Asp Val Pro Leu Pro Asn Tyr Ile Leu Gln
                500                 505                 510

Glu Ile Asp Tyr Pro Ser Arg Phe Asn Asp Leu Ala Ser Ser Leu Leu
                515                 520                 525

Arg Leu Arg Gly Asp Thr Arg Cys Tyr Lys Ala Asp Arg Ala Arg Gly
530                 535                 540
```

-continued

```
Glu Ala Ser Ala Ile Ser Cys Tyr Met Lys Asp His Pro Gly Ser
545                 550                 555                 560

Thr Glu Glu Asp Ala Leu Asn His Ile Asn Val Met Ile Ser Asp Ala
            565                 570                 575

Ile Arg Glu Leu Asn Trp Glu Leu Leu Arg Pro Asp Ser Lys Ser Pro
        580                 585                 590

Ile Ser Ser Lys Lys His Ala Phe Asp Ile Thr Arg Ala Phe His His
    595                 600                 605

Leu Tyr Lys Tyr Arg Asp Gly Tyr Thr Val Ala Ser Ser Glu Thr Lys
610                 615                 620

Asn Leu Val Met Lys Thr Val Leu Glu Pro Val Ala Leu
625                 630                 635
```

<210> SEQ ID NO 29
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: n equals unknown

<400> SEQUENCE: 29
gcntaygaya cngcntgggt                                          20

<210> SEQ ID NO 30
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(20)
<223> OTHER INFORMATION: n equals unknown

<400> SEQUENCE: 30
gcytkrtang tyttngtrtc                                          20

<210> SEQ ID NO 31
<211> LENGTH: 52
<212> TYPE: DNA
<213> ORGANISM: Artificial Sequence
<220> FEATURE:
<223> OTHER INFORMATION: Primer

<400> SEQUENCE: 31
tgataatccg cattaagcat ttttttttgtc gactcctcct gtggaagctg at      52

<210> SEQ ID NO 32
<211> LENGTH: 2622
<212> TYPE: DNA
<213> ORGANISM: Ginkgo biloba

<400> SEQUENCE: 32
atggctgggg tgctctttgc aaatctgcct tgctcactgc aactctctcc aaaagttccc    60
ttccggcaat ccactaatat tcttattcct tttcacaaga gatcctcatt tggatttaat   120
gcacagcact gcgtccgttc tcacttaagg ctgagatgga attgtgtcgg gattcatgcc   180
tcagctgcag agactcgtcc agatcagctt ccacaggagg aacgctttgt gtcgagactt   240
aatgcggatt atcatccagc tgtctggaag gacgatttca tcgactctct aacatcccct   300
```

-continued

```
aattcccacg cgacatcgaa atcaagcgtc gatgagacaa tcaataaaag aatccagaca    360
ttggtgaagg aaatccagtg catgtttcag tccatgggcg acggtgaaac gaatccatct    420
gcatatgata cagcttgggt ggcaagaatt ccgtcaattg acggctctgg tgcaccccaa    480
tttccccaaa cgcttcaatg gattctgaac aatcaactgc cagatggctc gtggggtgag    540
gagtgcattt ttctggcgta tgacagagtt ttaaacactc tcgcctgcct cctcactctc    600
aaaatatgga ataagggcga cattcaagtg cagaaagggg ttgagtttgt gagaaaacac    660
atggaagaaa tgaaggacga agctgacaat cacaggccaa gtggattcga ggtcgtgttt    720
cctgcaatgt tagatgaagc aaaaagcttg ggattggatc ttccttatca cctccctttc    780
atctcccaaa tccaccaaaa gcgccagaaa aagcttcaaa agattcccct caatgttctt    840
cataaccatc agacggcgtt gctctactct ctggagggtt tgcaagatgt ggtggactgg    900
caagagatca caaatcttca atcaagagac ggatcatttt taagctcccc tgcatctact    960
gcttgtgtct tcatgcacac tcaaaacaaa cgatgcctcc actttctcaa cttcgtgctc   1020
agcaaatttg gcgactacgt tccttgccat tacccacttg atctatttga acgcctctgg   1080
gctgtcgata cagttgaacg cttgggaatc gatcgctatt tcaagaaaga aatcaaagaa   1140
tctctggatt acgtttatag gtactgggac gccgaaagag gcgtgggatg gcaagatgc   1200 aatcctattc ctgatgtcga tgacactgcc atgggtctta gaatcctgag acttcatgga   1260
tacaatgtat cttcagatgt tctggagaat ttcagagacg agaaaggaga cttcttttgc   1320
tttgccggtc aaacgcaaat tggtgtgacc gataatctta acctttatag atgttcacaa   1380
gtatgttttc cgggagaaaa gataatggaa gaagctaaga ccttcactac aaatcatctc   1440
caaaatgctc ttgccaaaaa caacgcattt gataagtggg ctgtcaagaa ggatcttcct   1500
ggagaggtgg agtatgctat aaagtatccg tggcatagaa gtatgccaag attggaggca   1560
agaagttaca tagagcaatt tggatcaaat gatgtctggc tggggaagac tgtgtataag   1620
atgctatatg tgagcaacga aaaatatttg gagctggcca aattggactt caatatggtg   1680
caggccttac accaaaagga gactcaacac attgtcagct ggtggagaga atcgggattc   1740
aatgatctta cattcacccg ccagcggcct gtggaaatgt atttctcagt ggcggttagt   1800
atgtttgagc cagaattcgc tgcttgtaga attgcctatg ccaagacttc ttgcctcgca   1860
gttattctag acgatcttta cgacacccac ggatctctgg atgatcttaa attgttctct   1920
gaagcggtcc gaagatggga tatctctgtg ctggatagcg ttcgggataa tcagttgaaa   1980
gttttgcttc ctagggctgta caacacagtg aatggatttg gaaagatgg actcaaggaa   2040 caaggccgtg atgtgctggg ctatcttcga aaagtatggg agggcttgct cgcatcgtat   2100
accaaagaag ccgaatggtc ggcagcaaag tatgtgccga cattcaacga atatgtggaa   2160
aatgccaaag tgtccatagc acttgcgaca gtcgtactaa actcaatctt tttcactgga   2220
gaattacttc ctgattacat tttacagcaa gtagaccttg gtccaaatt tctgcatctt   2280 gtgtctttga ctggacgact aatcaatgac accaagactt accaggccga gagaaaccgt   2340
ggtgaattgg tttccagcgt acagtgctac atgagggaaa atccggagtg cacagaggaa   2400
gaagctctaa gtcatgttta tggtatcatc gacaacgcac tgaaggaatt gaattgggag   2460
ttggccaacc cagcgagcaa tgccccattg tgtgtgagaa gactgctgtt caacactgca   2520
agagtgatgc agctgtttta tatgtacaga gatggctttg gtatctctga caagagatg   2580 aaagaccatg tcagccgaac tcttttcgat cctgtggcgt ag                      2622
```

<210> SEQ ID NO 33
<211> LENGTH: 873
<212> TYPE: PRT
<213> ORGANISM: Ginkgo biloba

<400> SEQUENCE: 33

| Met | Ala | Gly | Val | Leu | Phe | Ala | Asn | Leu | Pro | Cys | Ser | Leu | Gln | Leu | Ser |
|---|---|---|---|---|---|---|---|---|---|---|---|---|---|---|---|
| 1 | | | | 5 | | | | | 10 | | | | | 15 | |

| Pro | Lys | Val | Pro | Phe | Arg | Gln | Ser | Thr | Asn | Ile | Leu | Ile | Pro | Phe | His |
| | | | 20 | | | | | 25 | | | | | 30 | | |

| Lys | Arg | Ser | Ser | Phe | Gly | Phe | Asn | Ala | Gln | His | Cys | Val | Arg | Ser | His |
| | | | 35 | | | | | 40 | | | | | 45 | | |

| Leu | Arg | Leu | Arg | Trp | Asn | Cys | Val | Gly | Ile | His | Ala | Ser | Ala | Ala | Glu |
| | | 50 | | | | | 55 | | | | | 60 | | | |

| Thr | Arg | Pro | Asp | Gln | Leu | Pro | Gln | Glu | Glu | Arg | Phe | Val | Ser | Arg | Leu |
| 65 | | | | | 70 | | | | | 75 | | | | | 80 |

| Asn | Ala | Asp | Tyr | His | Pro | Ala | Val | Trp | Lys | Asp | Asp | Phe | Ile | Asp | Ser |
| | | | | 85 | | | | | 90 | | | | | 95 | |

| Leu | Thr | Ser | Pro | Asn | Ser | His | Ala | Thr | Ser | Lys | Ser | Ser | Val | Asp | Glu |
| | | | 100 | | | | | 105 | | | | | 110 | | |

| Thr | Ile | Asn | Lys | Arg | Ile | Gln | Thr | Leu | Val | Lys | Glu | Ile | Gln | Cys | Met |
| | | | 115 | | | | | 120 | | | | | 125 | | |

| Phe | Gln | Ser | Met | Gly | Asp | Gly | Glu | Thr | Asn | Pro | Ser | Ala | Tyr | Asp | Thr |
| | | | 130 | | | | | 135 | | | | | 140 | | |

| Ala | Trp | Val | Ala | Arg | Ile | Pro | Ser | Ile | Asp | Gly | Ser | Gly | Ala | Pro | Gln |
| 145 | | | | | 150 | | | | | 155 | | | | | 160 |

| Phe | Pro | Gln | Thr | Leu | Gln | Trp | Ile | Leu | Asn | Asn | Gln | Leu | Pro | Asp | Gly |
| | | | | 165 | | | | | 170 | | | | | 175 | |

| Ser | Trp | Gly | Glu | Glu | Cys | Ile | Phe | Leu | Ala | Tyr | Asp | Arg | Val | Leu | Asn |
| | | | 180 | | | | | 185 | | | | | 190 | | |

| Thr | Leu | Ala | Cys | Leu | Leu | Thr | Leu | Lys | Ile | Trp | Asn | Lys | Gly | Asp | Ile |
| | | | 195 | | | | | 200 | | | | | 205 | | |

| Gln | Val | Gln | Lys | Gly | Val | Glu | Phe | Val | Arg | Lys | His | Met | Glu | Glu | Met |
| | | | 210 | | | | | 215 | | | | | 220 | | |

| Lys | Asp | Glu | Ala | Asp | Asn | His | Arg | Pro | Ser | Gly | Phe | Glu | Val | Val | Phe |
| 225 | | | | | 230 | | | | | 235 | | | | | 240 |

| Pro | Ala | Met | Leu | Asp | Glu | Ala | Lys | Ser | Leu | Gly | Leu | Asp | Leu | Pro | Tyr |
| | | | | 245 | | | | | 250 | | | | | 255 | |

| His | Leu | Pro | Phe | Ile | Ser | Gln | Ile | His | Gln | Lys | Arg | Gln | Lys | Lys | Leu |
| | | | 260 | | | | | 265 | | | | | 270 | | |

| Gln | Lys | Ile | Pro | Leu | Asn | Val | Leu | His | Asn | His | Gln | Thr | Ala | Leu | Leu |
| | | | 275 | | | | | 280 | | | | | 285 | | |

| Tyr | Ser | Leu | Glu | Gly | Leu | Gln | Asp | Val | Val | Asp | Trp | Gln | Glu | Ile | Thr |
| | | 290 | | | | | 295 | | | | | 300 | | | |

| Asn | Leu | Gln | Ser | Arg | Asp | Gly | Ser | Phe | Leu | Ser | Ser | Pro | Ala | Ser | Thr |
| 305 | | | | | 310 | | | | | 315 | | | | | 320 |

| Ala | Cys | Val | Phe | Met | His | Thr | Gln | Asn | Lys | Arg | Cys | Leu | His | Phe | Leu |
| | | | | 325 | | | | | 330 | | | | | 335 | |

| Asn | Phe | Val | Leu | Ser | Lys | Phe | Gly | Asp | Tyr | Val | Pro | Cys | His | Tyr | Pro |
| | | | 340 | | | | | 345 | | | | | 350 | | |

| Leu | Asp | Leu | Phe | Glu | Arg | Leu | Trp | Ala | Val | Asp | Thr | Val | Glu | Arg | Leu |
| | | | 355 | | | | | 360 | | | | | 365 | | |

| Gly | Ile | Asp | Arg | Tyr | Phe | Lys | Lys | Glu | Ile | Lys | Glu | Ser | Leu | Asp | Tyr |
| | | 370 | | | | | 375 | | | | | 380 | | | |

-continued

```
Val Tyr Arg Tyr Trp Asp Ala Glu Arg Gly Val Gly Trp Ala Arg Cys
385                 390                 395                 400

Asn Pro Ile Pro Asp Val Asp Asp Thr Ala Met Gly Leu Arg Ile Leu
                405                 410                 415

Arg Leu His Gly Tyr Asn Val Ser Ser Asp Val Leu Glu Asn Phe Arg
            420                 425                 430

Asp Glu Lys Gly Asp Phe Phe Cys Phe Ala Gly Gln Thr Gln Ile Gly
        435                 440                 445

Val Thr Asp Asn Leu Asn Leu Tyr Arg Cys Ser Gln Val Cys Phe Pro
    450                 455                 460

Gly Glu Lys Ile Met Glu Ala Lys Thr Phe Thr Thr Asn His Leu
465                 470                 475                 480

Gln Asn Ala Leu Ala Lys Asn Ala Phe Asp Lys Trp Ala Val Lys
                485                 490                 495

Lys Asp Leu Pro Gly Glu Val Glu Tyr Ala Ile Lys Tyr Pro Trp His
            500                 505                 510

Arg Ser Met Pro Arg Leu Glu Ala Arg Ser Tyr Ile Glu Gln Phe Gly
        515                 520                 525

Ser Asn Asp Val Trp Leu Gly Lys Thr Val Tyr Lys Met Leu Tyr Val
    530                 535                 540

Ser Asn Glu Lys Tyr Leu Glu Leu Ala Lys Leu Asp Phe Asn Met Val
545                 550                 555                 560

Gln Ala Leu His Gln Lys Glu Thr Gln His Ile Val Ser Trp Trp Arg
                565                 570                 575

Glu Ser Gly Phe Asn Asp Leu Thr Phe Thr Arg Gln Arg Pro Val Glu
            580                 585                 590

Met Tyr Phe Ser Val Ala Val Ser Met Phe Glu Pro Glu Phe Ala Ala
        595                 600                 605

Cys Arg Ile Ala Tyr Ala Lys Thr Ser Cys Leu Ala Val Ile Leu Asp
    610                 615                 620

Asp Leu Tyr Asp Thr His Gly Ser Leu Asp Asp Leu Lys Leu Phe Ser
625                 630                 635                 640

Glu Ala Val Arg Arg Trp Asp Ile Ser Val Leu Asp Ser Val Arg Asp
                645                 650                 655

Asn Gln Leu Lys Val Cys Phe Leu Gly Leu Tyr Asn Thr Val Asn Gly
            660                 665                 670

Phe Gly Lys Asp Gly Leu Lys Glu Gln Gly Arg Asp Val Leu Gly Tyr
        675                 680                 685

Leu Arg Lys Val Trp Glu Gly Leu Leu Ala Ser Tyr Thr Lys Glu Ala
    690                 695                 700

Glu Trp Ser Ala Ala Lys Tyr Val Pro Thr Phe Asn Glu Tyr Val Glu
705                 710                 715                 720

Asn Ala Lys Val Ser Ile Ala Leu Ala Thr Val Val Leu Asn Ser Ile
                725                 730                 735

Phe Phe Thr Gly Glu Leu Leu Pro Asp Tyr Ile Leu Gln Gln Val Asp
            740                 745                 750

Leu Arg Ser Lys Phe Leu His Leu Val Ser Leu Thr Gly Arg Leu Ile
        755                 760                 765

Asn Asp Thr Lys Thr Tyr Gln Ala Glu Arg Asn Arg Gly Glu Leu Val
    770                 775                 780

Ser Ser Val Gln Cys Tyr Met Arg Glu Asn Pro Glu Cys Thr Glu Glu
785                 790                 795                 800
```

```
Glu Ala Leu Ser His Val Tyr Gly Ile Ile Asp Asn Ala Leu Lys Glu
            805                 810                 815
Leu Asn Trp Glu Leu Ala Asn Pro Ala Ser Asn Ala Pro Leu Cys Val
        820                 825                 830
Arg Arg Leu Leu Phe Asn Thr Ala Arg Val Met Gln Leu Phe Tyr Met
            835                 840                 845
Tyr Arg Asp Gly Phe Gly Ile Ser Asp Lys Glu Met Lys Asp His Val
    850                 855                 860
Ser Arg Thr Leu Phe Asp Pro Val Ala
865                 870
```

<210> SEQ ID NO 34
<211> LENGTH: 2445
<212> TYPE: DNA
<213> ORGANISM: Ginkgo biloba

<400> SEQUENCE: 34

| | |
|---|---|
| atgtcagctg cagagactcg tccagatcag cttccacagg aggaacgctt tgtgtcgaga | 60 |
| cttaatgcgg attatcatcc agctgtctgg aaggacgatt tcatcgactc tctaacatcc | 120 |
| cctaattccc acgcgacatc gaaatcaagc gtcgatgaga caatcaataa agaatccag | 180 |
| acattggtga aggaaatcca gtgcatgttt cagtccatgg cgacggtga acgaatcca | 240 |
| tctgcatatg atacagcttg ggtggcaaga attccgtcaa ttgacggctc tggtgcaccc | 300 |
| caatttcccc aaacgcttca atggattctg aacaatcaac tgccagatgg ctcgtggggt | 360 |
| gaggagtgca tttttctggc gtatgacaga gttttaaaca ctctcgcctg cctcctcact | 420 |
| ctcaaaatat ggaataaggg cgacattcaa gtgcagaaag gggttgagtt tgtgagaaaa | 480 |
| cacatggaag aaatgaagga cgaagctgac aatcacaggc caagtggatt cgaggtcgtg | 540 |
| tttcctgcaa tgttagatga agcaaaaagc ttgggattgg atcttcctta tcacctccct | 600 |
| ttcatctccc aaatccacca aaagcgccag aaaaagcttc aaaagattcc cctcaatgtt | 660 |
| cttcataacc atcagacggc gttgctctac tctctggagg gtttgcaaga tgtggtggac | 720 |
| tggcaagaga tcacaaatct tcaatcaaga gacggatcat ttttaagctc ccctgcatct | 780 |
| actgcttgtg tcttcatgca cactcaaaac aaacgatgcc tccactttct caacttcgtg | 840 |
| ctcagcaaat ttggcgacta cgttccttgc cattacccac ttgatctatt tgaacgcctc | 900 |
| tgggctgtcg atacagttga acgcttggga atcgatcgct atttcaagaa agaaatcaaa | 960 |
| gaatctctgg attacgttta taggtactgg gacgccgaaa gaggcgtggg atgggcaaga | 1020 |
| tgcaatccta ttcctgatgt cgatgacact gccatgggtc ttagaatcct gagacttcat | 1080 |
| ggatacaatg tatcttcaga tgttctggag aatttcagag acgagaaagg agacttcttt | 1140 |
| tgctttgccg gtcaaacgca aattggtgtg accgataatc ttaacctta tagatgttca | 1200 |
| caagtatgtt ttccgggaga aaagataatg gaagaagcta agaccttcac tacaaatcat | 1260 |
| ctccaaaatg ctcttgccaa aaacaacgca tttgataagt gggctgtcaa gaaggatctt | 1320 |
| cctggagagg tggagtatgc tataaagtat ccgtggcata agtatgcc aagattggag | 1380 |
| gcaagaagtt acatagagca atttggatca aatgatgtct ggctggggaa gactgtgtat | 1440 |
| aagatgctat atgtgagcaa cgaaaaatat tggagctgg ccaaattgga cttcaatatg | 1500 |
| gtgcaggcct acaccaaaaa ggagactcaa cacattgtca gctggtggag agaatcggga | 1560 |
| ttcaatgatc ttacattcac ccgccagcgg cctgtggaaa tgtatttctc agtggcggtt | 1620 |
| agtatgtttg agccagaatt cgctgcttgt agaattgcct atgccaagac ttcttgcctc | 1680 |

-continued

```
gcagttattc tagacgatct ttacgacacc cacggatctc tgatgatct taaattgttc    1740 tctgaagcgg tccgaagatg ggatatctct gtgctggata gcgttcggga taatcagttg    1800
aaagtttgct tcctagggct gtacaacaca gtgaatggat ttggaaaaga tggactcaag    1860
gaacaaggcc gtgatgtgct gggctatctt cgaaaagtat gggagggctt gctcgcatcg    1920
tataccaaag aagccgaatg gtcggcagca agtatgtgc cgacattcaa cgaatatgtg    1980
gaaaatgcca aagtgtccat agcacttgcg acagtcgtac taaactcaat cttttcact    2040 ggagaattac ttcctgatta cattttacag caagtagacc ttcggtccaa atttctgcat    2100
cttgtgtctt tgactggacg actaatcaat gacaccaaga cttaccaggc cgagagaaac    2160
cgtggtgaat tggtttccag cgtacagtgc tacatgaggg aaaatccgga gtgcacagag    2220
gaagaagctc taagtcatgt ttatggtatc atcgacaacg cactgaagga attgaattgg    2280
gagttggcca acccagcgag caatgcccca ttgtgtgtga aagactgct gttcaacact    2340 gcaagagtga tgcagctgtt ttatatgtac agagatggct ttggtatctc tgacaaagag    2400
atgaaagacc atgtcagccg aactctttc gatcctgtgg cgtag            2445
```

```
<210> SEQ ID NO 35
<211> LENGTH: 814
<212> TYPE: PRT
<213> ORGANISM: Ginkgo biloba

<400> SEQUENCE: 35
```

Met Ser Ala Ala Glu Thr Arg Pro Asp Gln Leu Pro Gln Glu Glu Arg
1               5                   10                  15

Phe Val Ser Arg Leu Asn Ala Asp Tyr His Pro Ala Val Trp Lys Asp
                20                  25                  30

Asp Phe Ile Asp Ser Leu Thr Ser Pro Asn Ser His Ala Thr Ser Lys
            35                  40                  45

Ser Ser Val Asp Glu Thr Ile Asn Lys Arg Ile Gln Thr Leu Val Lys
        50                  55                  60

Glu Ile Gln Cys Met Phe Gln Ser Met Gly Asp Gly Glu Thr Asn Pro
65                  70                  75                  80

Ser Ala Tyr Asp Thr Ala Trp Val Ala Arg Ile Pro Ser Ile Asp Gly
                85                  90                  95

Ser Gly Ala Pro Gln Phe Pro Gln Thr Leu Gln Trp Ile Leu Asn Asn
            100                 105                 110

Gln Leu Pro Asp Gly Ser Trp Gly Glu Glu Cys Ile Phe Leu Ala Tyr
        115                 120                 125

Asp Arg Val Leu Asn Thr Leu Ala Cys Leu Leu Thr Leu Lys Ile Trp
    130                 135                 140

Asn Lys Gly Asp Ile Gln Val Gln Lys Gly Val Glu Phe Val Arg Lys
145                 150                 155                 160

His Met Glu Glu Met Lys Asp Glu Ala Asp Asn His Arg Pro Ser Gly
                165                 170                 175

Phe Glu Val Val Phe Pro Ala Met Leu Asp Glu Ala Lys Ser Leu Gly
            180                 185                 190

Leu Asp Leu Pro Tyr His Leu Pro Phe Ile Ser Gln Ile His Gln Lys
        195                 200                 205

Arg Gln Lys Lys Leu Gln Lys Ile Pro Leu Asn Val Leu His Asn His
    210                 215                 220

Gln Thr Ala Leu Leu Tyr Ser Leu Glu Gly Leu Gln Asp Val Val Asp
225                 230                 235                 240

```
Trp Gln Glu Ile Thr Asn Leu Gln Ser Arg Asp Gly Ser Phe Leu Ser
            245                 250                 255

Ser Pro Ala Ser Thr Ala Cys Val Phe Met His Thr Gln Asn Lys Arg
            260                 265                 270

Cys Leu His Phe Leu Asn Phe Val Leu Ser Lys Phe Gly Asp Tyr Val
            275                 280                 285

Pro Cys His Tyr Pro Leu Asp Leu Phe Glu Arg Leu Trp Ala Val Asp
            290                 295                 300

Thr Val Glu Arg Leu Gly Ile Asp Arg Tyr Phe Lys Lys Glu Ile Lys
305                 310                 315                 320

Glu Ser Leu Asp Tyr Val Tyr Arg Tyr Trp Asp Ala Glu Arg Gly Val
            325                 330                 335

Gly Trp Ala Arg Cys Asn Pro Ile Pro Asp Val Asp Asp Thr Ala Met
            340                 345                 350

Gly Leu Arg Ile Leu Arg Leu His Gly Tyr Asn Val Ser Ser Asp Val
            355                 360                 365

Leu Glu Asn Phe Arg Asp Glu Lys Gly Asp Phe Phe Cys Phe Ala Gly
            370                 375                 380

Gln Thr Gln Ile Gly Val Thr Asp Asn Leu Asn Leu Tyr Arg Cys Ser
385                 390                 395                 400

Gln Val Cys Phe Pro Gly Glu Lys Ile Met Glu Glu Ala Lys Thr Phe
            405                 410                 415

Thr Thr Asn His Leu Gln Asn Ala Leu Ala Lys Asn Asn Ala Phe Asp
            420                 425                 430

Lys Trp Ala Val Lys Lys Asp Leu Pro Gly Glu Val Glu Tyr Ala Ile
            435                 440                 445

Lys Tyr Pro Trp His Arg Ser Met Pro Arg Leu Glu Ala Arg Ser Tyr
            450                 455                 460

Ile Glu Gln Phe Gly Ser Asn Asp Val Trp Leu Gly Lys Thr Val Tyr
465                 470                 475                 480

Lys Met Leu Tyr Val Ser Asn Glu Lys Tyr Leu Glu Leu Ala Lys Leu
            485                 490                 495

Asp Phe Asn Met Val Gln Ala Leu His Gln Lys Glu Thr Gln His Ile
            500                 505                 510

Val Ser Trp Trp Arg Glu Ser Gly Phe Asn Asp Leu Thr Phe Thr Arg
            515                 520                 525

Gln Arg Pro Val Glu Met Tyr Phe Ser Val Ala Val Ser Met Phe Glu
            530                 535                 540

Pro Glu Phe Ala Ala Cys Arg Ile Ala Tyr Ala Lys Thr Ser Cys Leu
545                 550                 555                 560

Ala Val Ile Leu Asp Asp Leu Tyr Asp Thr His Gly Ser Leu Asp Asp
            565                 570                 575

Leu Lys Leu Phe Ser Glu Ala Val Arg Arg Trp Asp Ile Ser Val Leu
            580                 585                 590

Asp Ser Val Arg Asp Asn Gln Leu Lys Val Cys Phe Leu Gly Leu Tyr
            595                 600                 605

Asn Thr Val Asn Gly Phe Gly Lys Asp Gly Leu Lys Glu Gln Gly Arg
            610                 615                 620

Asp Val Leu Gly Tyr Leu Arg Lys Val Trp Glu Gly Leu Leu Ala Ser
625                 630                 635                 640

Tyr Thr Lys Glu Ala Glu Trp Ser Ala Ala Lys Tyr Val Pro Thr Phe
            645                 650                 655
```

-continued

```
Asn Glu Tyr Val Glu Asn Ala Lys Val Ser Ile Ala Leu Ala Thr Val
            660                 665                 670
Val Leu Asn Ser Ile Phe Phe Thr Gly Glu Leu Leu Pro Asp Tyr Ile
        675                 680                 685
Leu Gln Gln Val Asp Leu Arg Ser Lys Phe Leu His Leu Val Ser Leu
    690                 695                 700
Thr Gly Arg Leu Ile Asn Asp Thr Lys Thr Tyr Gln Ala Glu Arg Asn
705                 710                 715                 720
Arg Gly Glu Leu Val Ser Ser Val Gln Cys Tyr Met Arg Glu Asn Pro
                725                 730                 735
Glu Cys Thr Glu Glu Ala Leu Ser His Val Tyr Gly Ile Ile Asp
            740                 745                 750
Asn Ala Leu Lys Glu Leu Asn Trp Glu Leu Ala Asn Pro Ala Ser Asn
        755                 760                 765
Ala Pro Leu Cys Val Arg Arg Leu Leu Phe Asn Thr Ala Arg Val Met
    770                 775                 780
Gln Leu Phe Tyr Met Tyr Arg Asp Gly Phe Gly Ile Ser Asp Lys Glu
785                 790                 795                 800
Met Lys Asp His Val Ser Arg Thr Leu Phe Asp Pro Val Ala
                805                 810
```

<210> SEQ ID NO 36
<211> LENGTH: 2388
<212> TYPE: DNA
<213> ORGANISM: Ginkgo biloba

<400> SEQUENCE: 36

```
atgcttaatg cggattatca tccagctgtc tggaaggacg atttcatcga ctctctaaca      60
tcccctaatt cccacgcgac atcgaaatca agcgtcgatg agacaatcaa taaaagaatc     120
cagacattgg tgaaggaaat ccagtgcatg tttcagtcca tgggcgacgg tgaaacgaat     180
ccatctgcat atgatacagc ttgggtggca agaattccgt caattgacgg ctctggtgca     240
ccccaatttc cccaaacgct tcaatggatt ctgaacaatc aactgccaga tggctcgtgg     300
ggtgaggagt gcatttttct ggcgtatgac agagttttaa acactctcgc ctgcctcctc     360
actctcaaaa tatggaataa gggcgacatt caagtgcaga aagggggttga gtttgtgaga     420
aaacacatgg aagaaatgaa ggacgaagct gacaatcaca ggccaagtgg attcgaggtc     480
gtgtttcctg caatgttaga tgaagcaaaa agcttgggat tggatcttcc ttatcacctc     540
cctttcatct cccaaatcca ccaaaagcgc cagaaaaagc ttcaaaagat tcccctcaat     600
gttcttcata accatcagac ggcgttgctc tactctctgg agggtttgca agatgtggtg     660
gactggcaag agatcacaaa tcttcaatca agagacggat catttttaag ctcccctgca     720
tctactgctt tgtgtcttca tgcacactca aacaaacgat gcctccactt tctcaacttc     780
gtgctcagca aatttggcga ctacgttcct tgccattacc cacttgatct atttgaacgc     840
ctctgggctg tcgatacagt tgaacgcttg ggaatcgatc gctatttcaa gaaagaaatc     900
aaagaatctc tggattacgt ttataggtac tgggacgccg aaagaggcgt gggatgggca     960
agatgcaatc ctattcctga tgtcgatgac actgccatgg gtcttagaat cctgagactt    1020
catggataca atgtatcttc agatgttctg gagaatttca gagacgagaa aggagacttc    1080
ttttgctttg ccggtcaaac gcaaattggt gtgaccgata atcttaacct ttatagatgt    1140
tcacaagtat gttttccggg agaaaagata atggaagaag ctaagacctt cactacaaat    1200
catctccaaa atgctcttgc caaaaacaac gcatttgata agtgggctgt caagaaggat    1260
```

-continued

```
cttcctggag aggtggagta tgctataaag tatccgtggc atagaagtat gccaagattg   1320
gaggcaagaa gttacataga gcaatttgga tcaaatgatg tctggctggg aagactgtg    1380
tataagatgc tatatgtgag caacgaaaaa tatttggagc tggccaaatt ggacttcaat   1440
atggtgcagg ccttacacca aaaggagact caacacattg tcagctggtg gagagaatcg   1500
ggattcaatg atcttacatt cacccgccag cggcctgtgg aaatgtattt ctcagtggcg   1560
gttagtatgt ttgagccaga attcgctgct tgtagaattc cctatgccaa gacttcttgc   1620
ctcgcagtta ttctagacga tctttacgac acccacggat ctctggatga tcttaaattg   1680
ttctctgaag cggtccgaag atgggatatc tctgtgctgg atagcgttcg ggataatcag   1740
ttgaaagttt gcttcctagg gctgtacaac acagtgaatg gatttggaaa agatggactc   1800
aaggaacaag gccgtgatgt gctgggctat cttcgaaaag tatgggaggg cttgctcgca   1860
tcgtatacca agaagccga atggtcggca gcaaagtatg tgccgacatt caacgaatat    1920
gtggaaaatg ccaaagtgtc catagcactt gcgacagtcg tactaaactc aatctttttc   1980
actggagaat tacttcctga ttacatttta cagcaagtag accttcggtc caaatttctg   2040
catcttgtgt ctttgactgg acgactaatc aatgacacca agacttacca ggccgagaga   2100
aaccgtggtg aattggtttc cagcgtacag tgctacatga gggaaaatcc ggagtgcaca   2160
gaggaagaag ctctaagtca tgtttatggt atcatcgaca acgcactgaa ggaattgaat   2220
tgggagttgg ccaacccagc gagcaatgcc ccattgtgtg tgagaagact gctgttcaac   2280
actgcaagag tgatgcagct gttttatatg tacagagatg gctttggtat ctctgacaaa   2340
gagatgaaag accatgtcag ccgaactctt ttcgatcctg tggcgtag               2388
```

<210> SEQ ID NO 37
<211> LENGTH: 795
<212> TYPE: PRT
<213> ORGANISM: Ginkgo biloba

<400> SEQUENCE: 37

```
Met Leu Asn Ala Asp Tyr His Pro Ala Val Trp Lys Asp Asp Phe Ile
1               5                  10                  15

Asp Ser Leu Thr Ser Pro Asn Ser His Ala Thr Ser Lys Ser Ser Val
            20                  25                  30

Asp Glu Thr Ile Asn Lys Arg Ile Gln Thr Leu Val Lys Glu Ile Gln
        35                  40                  45

Cys Met Phe Gln Ser Met Gly Asp Gly Glu Thr Asn Pro Ser Ala Tyr
    50                  55                  60

Asp Thr Ala Trp Val Ala Arg Ile Pro Ser Ile Asp Gly Ser Gly Ala
65                  70                  75                  80

Pro Gln Phe Pro Gln Thr Leu Gln Trp Ile Leu Asn Asn Gln Leu Pro
                85                  90                  95

Asp Gly Ser Trp Gly Glu Glu Cys Ile Phe Leu Ala Tyr Asp Arg Val
            100                 105                 110

Leu Asn Thr Leu Ala Cys Leu Leu Thr Leu Lys Ile Trp Asn Lys Gly
        115                 120                 125

Asp Ile Gln Val Gln Lys Gly Val Glu Phe Val Arg Lys His Met Glu
    130                 135                 140

Glu Met Lys Asp Glu Ala Asp Asn His Arg Pro Ser Gly Phe Glu Val
145                 150                 155                 160

Val Phe Pro Ala Met Leu Asp Glu Ala Lys Ser Leu Gly Leu Asp Leu
                165                 170                 175
```

```
Pro Tyr His Leu Pro Phe Ile Ser Gln Ile His Gln Lys Arg Gln Lys
        180                 185                 190

Lys Leu Gln Lys Ile Pro Leu Asn Val Leu His Asn His Gln Thr Ala
        195                 200                 205

Leu Leu Tyr Ser Leu Glu Gly Leu Gln Asp Val Val Asp Trp Gln Glu
    210                 215                 220

Ile Thr Asn Leu Gln Ser Arg Asp Gly Ser Phe Leu Ser Ser Pro Ala
225                 230                 235                 240

Ser Thr Ala Cys Val Phe Met His Thr Gln Asn Lys Arg Cys Leu His
            245                 250                 255

Phe Leu Asn Phe Val Leu Ser Lys Phe Gly Asp Tyr Val Pro Cys His
            260                 265                 270

Tyr Pro Leu Asp Leu Phe Glu Arg Leu Trp Ala Val Asp Thr Val Glu
        275                 280                 285

Arg Leu Gly Ile Asp Arg Tyr Phe Lys Lys Glu Ile Lys Glu Ser Leu
    290                 295                 300

Asp Tyr Val Tyr Arg Tyr Trp Asp Ala Glu Arg Gly Val Gly Trp Ala
305                 310                 315                 320

Arg Cys Asn Pro Ile Pro Asp Val Asp Asp Thr Ala Met Gly Leu Arg
                325                 330                 335

Ile Leu Arg Leu His Gly Tyr Asn Val Ser Ser Asp Val Leu Glu Asn
        340                 345                 350

Phe Arg Asp Glu Lys Gly Asp Phe Phe Cys Phe Ala Gly Gln Thr Gln
        355                 360                 365

Ile Gly Val Thr Asp Asn Leu Asn Leu Tyr Arg Cys Ser Gln Val Cys
    370                 375                 380

Phe Pro Gly Glu Lys Ile Met Glu Glu Ala Lys Thr Phe Thr Thr Asn
385                 390                 395                 400

His Leu Gln Asn Ala Leu Ala Lys Asn Asn Ala Phe Asp Lys Trp Ala
                405                 410                 415

Val Lys Lys Asp Leu Pro Gly Glu Val Glu Tyr Ala Ile Lys Tyr Pro
            420                 425                 430

Trp His Arg Ser Met Pro Arg Leu Glu Ala Arg Ser Tyr Ile Glu Gln
        435                 440                 445

Phe Gly Ser Asn Asp Val Trp Leu Gly Lys Thr Val Tyr Lys Met Leu
    450                 455                 460

Tyr Val Ser Asn Glu Lys Tyr Leu Glu Leu Ala Lys Leu Asp Phe Asn
465                 470                 475                 480

Met Val Gln Ala Leu His Gln Lys Glu Thr Gln His Ile Val Ser Trp
            485                 490                 495

Trp Arg Glu Ser Gly Phe Asn Asp Leu Thr Phe Thr Arg Gln Arg Pro
                500                 505                 510

Val Glu Met Tyr Phe Ser Val Ala Val Ser Met Phe Glu Pro Glu Phe
        515                 520                 525

Ala Ala Cys Arg Ile Ala Tyr Ala Lys Thr Ser Cys Leu Ala Val Ile
    530                 535                 540

Leu Asp Asp Leu Tyr Asp Thr His Gly Ser Leu Asp Asp Leu Lys Leu
545                 550                 555                 560

Phe Ser Glu Ala Val Arg Arg Trp Asp Ile Ser Val Leu Asp Ser Val
            565                 570                 575

Arg Asp Asn Gln Leu Lys Val Cys Phe Leu Gly Leu Tyr Asn Thr Val
            580                 585                 590
```

-continued

```
Asn Gly Phe Gly Lys Asp Gly Leu Lys Glu Gln Gly Arg Asp Val Leu
            595                 600                 605
Gly Tyr Leu Arg Lys Val Trp Glu Gly Leu Leu Ala Ser Tyr Thr Lys
        610                 615                 620
Glu Ala Glu Trp Ser Ala Ala Lys Tyr Val Pro Thr Phe Asn Glu Tyr
625                 630                 635                 640
Val Glu Asn Ala Lys Val Ser Ile Ala Leu Ala Thr Val Val Leu Asn
                645                 650                 655
Ser Ile Phe Phe Thr Gly Glu Leu Leu Pro Asp Tyr Ile Leu Gln Gln
            660                 665                 670
Val Asp Leu Arg Ser Lys Phe Leu His Leu Val Ser Leu Thr Gly Arg
        675                 680                 685
Leu Ile Asn Asp Thr Lys Thr Tyr Gln Ala Glu Arg Asn Arg Gly Glu
690                 695                 700
Leu Val Ser Ser Val Gln Cys Tyr Met Arg Glu Asn Pro Glu Cys Thr
705                 710                 715                 720
Glu Glu Glu Ala Leu Ser His Val Tyr Gly Ile Ile Asp Asn Ala Leu
                725                 730                 735
Lys Glu Leu Asn Trp Glu Leu Ala Asn Pro Ala Ser Asn Ala Pro Leu
            740                 745                 750
Cys Val Arg Arg Leu Leu Phe Asn Thr Ala Arg Val Met Gln Leu Phe
        755                 760                 765
Tyr Met Tyr Arg Asp Gly Phe Gly Ile Ser Asp Lys Glu Met Lys Asp
770                 775                 780
His Val Ser Arg Thr Leu Phe Asp Pro Val Ala
785                 790                 795
```

<210> SEQ ID NO 38
<211> LENGTH: 2241
<212> TYPE: DNA
<213> ORGANISM: Ginkgo biloba

<400> SEQUENCE: 38

```
atgtttcagt ccatgggcga cggtgaaacg aatccatctg catatgatac agcttgggtg      60
gcaagaattc cgtcaattga cggctctggt gcaccccaat ttccccaaac gcttcaatgg     120
attctgaaca tcaactgcc agatggctcg tgggtgagg agtgcatttt tctggcgtat      180
gacagagttt taaacactct cgcctgcctc ctcactctca aaatatggaa taagggcgac     240
attcaagtgc agaaggggt tgagtttgtg agaaaacaca tggaagaaat gaaggacgaa     300
gctgacaatc acaggccaag tggattcgag gtcgtgtttc ctgcaatgtt agatgaagca     360
aaaagcttgg gattggatct tccttatcac ctccctttca tctcccaaat ccaccaaaag     420
cgccagaaaa agcttcaaaa gattcccctc aatgttcttc ataaccatca gacggcgttg     480
ctctactctc tggagggttt gcaagatgtg gtggactggc aagagatcac aaatcttcaa     540
tcaagagacg gatcattttt aagctcccct gcatctactg cttgtgtctt catgcacact     600
caaaacaaac gatgcctcca ctttctcaac ttcgtgctca gcaaatttgg cgactacgtt     660
ccttgccatt acccacttga tctatttgaa cgcctctggg ctgtcgatac agttgaacgc     720
ttgggaatcg atcgctattt caagaaagaa atcaaagaat ctctggatta cgtttatagg     780
tactgggacg ccgaaagagg cgtgggatgg caagatgca atcctattcc tgatgtcgat     840
gacactgcca tggtcttag aatcctgaga cttcatggat acaatgtatc ttcagatgtt     900
ctggagaatt tcagagacga gaaggagac ttcttttgct ttgccggtca aacgcaaatt    960
```

-continued

```
ggtgtgaccg ataatcttaa cctttataga tgttcacaag tatgttttcc gggagaaaag    1020
ataatggaag aagctaagac cttcactaca aatcatctcc aaaatgctct tgccaaaaac    1080
aacgcatttg ataagtgggc tgtcaagaag gatcttcctg agaggtgga gtatgctata     1140 aagtatccgt ggcatagaag tatgccaaga ttggaggcaa aagttacat agagcaattt     1200 ggatcaaatg atgtctggct ggggaagact gtgtataaga tgctatatgt gagcaacgaa    1260
aaatatttgg agctggccaa attggacttc aatatggtgc aggccttaca ccaaaaggag    1320
actcaacaca ttgtcagctg gtggagagaa tcgggattca atgatcttac attcacccgc    1380
cagcggcctg tggaaatgta tttctcagtg gcggttagta tgtttgagcc agaattcgct    1440
gcttgtagaa ttgcctatgc caagacttct tgcctcgcag ttattctaga cgatctttac    1500
gacacccacg gatctctgga tgatcttaaa ttgttctctg aagcggtccg aagatgggat    1560
atctctgtgc tggatagcgt tcgggataat cagttgaaag tttgcttcct agggctgtac    1620
aacacagtga atggatttgg aaaagatgga ctcaaggaac aaggccgtga tgtgctgggc    1680
tatcttcgaa aagtatggga gggcttgctc gcatcgtata ccaaagaagc cgaatggtcg    1740
gcagcaaagt atgtgccgac attcaacgaa tatgtgaaa atgccaaagt gtccatagca    1800
cttgcgacag tcgtactaaa ctcaatcttt ttcactggag aattacttcc tgattacatt    1860
ttacagcaag tagaccttcg gtccaaattt ctgcatcttg tgtctttgac tggacgacta    1920
atcaatgaca ccaagactta ccaggccgag agaaaccgtg gtgaattggt ttccagcgta    1980
cagtgctaca tgagggaaaa tccggagtgc acagaggaag aagctctaag tcatgtttat    2040
ggtatcatcg acaacgcact gaaggaattg aattgggagt tggccaaccc agcgagcaat    2100
gccccattgt gtgtgagaag actgctgttc aacactgcaa gagtgatgca gctgtttat     2160 atgtacagag atggctttgg tatctctgac aaagagatga agaccatgt cagccgaact     2220 cttttcgatc ctgtggcgta g                                              2241
```

<210> SEQ ID NO 39
<211> LENGTH: 746
<212> TYPE: PRT
<213> ORGANISM: Ginkgo biloba

<400> SEQUENCE: 39

```
Met Phe Gln Ser Met Gly Asp Gly Glu Thr Asn Pro Ser Ala Tyr Asp
 1               5                  10                  15

Thr Ala Trp Val Ala Arg Ile Pro Ser Ile Asp Gly Ser Gly Ala Pro
                20                  25                  30

Gln Phe Pro Gln Thr Leu Gln Trp Ile Leu Asn Asn Gln Leu Pro Asp
            35                  40                  45

Gly Ser Trp Gly Glu Glu Cys Ile Phe Leu Ala Tyr Asp Arg Val Leu
        50                  55                  60

Asn Thr Leu Ala Cys Leu Leu Thr Leu Lys Ile Trp Asn Lys Gly Asp
    65                  70                  75                  80

Ile Gln Val Gln Lys Gly Val Glu Phe Val Arg Lys His Met Glu Glu
                85                  90                  95

Met Lys Asp Glu Ala Asp Asn His Arg Pro Ser Gly Phe Glu Val Val
            100                 105                 110

Phe Pro Ala Met Leu Asp Glu Ala Lys Ser Leu Gly Leu Asp Leu Pro
        115                 120                 125

Tyr His Leu Pro Phe Ile Ser Gln Ile His Gln Lys Arg Gln Lys Lys
    130                 135                 140
```

-continued

```
Leu Gln Lys Ile Pro Leu Asn Val Leu His Asn His Gln Thr Ala Leu
145                 150                 155                 160

Leu Tyr Ser Leu Glu Gly Leu Gln Asp Val Val Asp Trp Gln Glu Ile
            165                 170                 175

Thr Asn Leu Gln Ser Arg Asp Gly Ser Phe Leu Ser Ser Pro Ala Ser
        180                 185                 190

Thr Ala Cys Val Phe Met His Thr Gln Asn Lys Arg Cys Leu His Phe
    195                 200                 205

Leu Asn Phe Val Leu Ser Lys Phe Gly Asp Tyr Val Pro Cys His Tyr
210                 215                 220

Pro Leu Asp Leu Phe Glu Arg Leu Trp Ala Val Asp Thr Val Glu Arg
225                 230                 235                 240

Leu Gly Ile Asp Arg Tyr Phe Lys Lys Glu Ile Lys Glu Ser Leu Asp
                245                 250                 255

Tyr Val Tyr Arg Tyr Trp Asp Ala Glu Arg Gly Val Gly Trp Ala Arg
            260                 265                 270

Cys Asn Pro Ile Pro Asp Val Asp Asp Thr Ala Met Gly Leu Arg Ile
        275                 280                 285

Leu Arg Leu His Gly Tyr Asn Val Ser Ser Asp Val Leu Glu Asn Phe
290                 295                 300

Arg Asp Glu Lys Gly Asp Phe Phe Cys Phe Ala Gly Gln Thr Gln Ile
305                 310                 315                 320

Gly Val Thr Asp Asn Leu Asn Leu Tyr Arg Cys Ser Gln Val Cys Phe
                325                 330                 335

Pro Gly Glu Lys Ile Met Glu Glu Ala Lys Thr Phe Thr Thr Asn His
            340                 345                 350

Leu Gln Asn Ala Leu Ala Lys Asn Asn Ala Phe Asp Lys Trp Ala Val
        355                 360                 365

Lys Lys Asp Leu Pro Gly Glu Val Glu Tyr Ala Ile Lys Tyr Pro Trp
370                 375                 380

His Arg Ser Met Pro Arg Leu Glu Ala Arg Ser Tyr Ile Glu Gln Phe
385                 390                 395                 400

Gly Ser Asn Asp Val Trp Leu Gly Lys Thr Val Tyr Lys Met Leu Tyr
                405                 410                 415

Val Ser Asn Glu Lys Tyr Leu Glu Leu Ala Lys Leu Asp Phe Asn Met
            420                 425                 430

Val Gln Ala Leu His Gln Lys Glu Thr Gln His Ile Val Ser Trp Trp
        435                 440                 445

Arg Glu Ser Gly Phe Asn Asp Leu Thr Phe Thr Arg Gln Arg Pro Val
450                 455                 460

Glu Met Tyr Phe Ser Val Ala Val Ser Met Phe Glu Pro Glu Phe Ala
465                 470                 475                 480

Ala Cys Arg Ile Ala Tyr Ala Lys Thr Ser Cys Leu Ala Val Ile Leu
                485                 490                 495

Asp Asp Leu Tyr Asp Thr His Gly Ser Leu Asp Asp Leu Lys Leu Phe
            500                 505                 510

Ser Glu Ala Val Arg Arg Trp Asp Ile Ser Val Leu Asp Ser Val Arg
        515                 520                 525

Asp Asn Gln Leu Lys Val Cys Phe Leu Gly Leu Tyr Asn Thr Val Asn
530                 535                 540

Gly Phe Gly Lys Asp Gly Leu Lys Glu Gln Gly Arg Asp Val Leu Gly
545                 550                 555                 560
```

-continued

```
Tyr Leu Arg Lys Val Trp Glu Gly Leu Leu Ala Ser Tyr Thr Lys Glu
                565                 570                 575

Ala Glu Trp Ser Ala Ala Lys Tyr Val Pro Thr Phe Asn Glu Tyr Val
            580                 585                 590

Glu Asn Ala Lys Val Ser Ile Ala Leu Ala Thr Val Val Leu Asn Ser
        595                 600                 605

Ile Phe Phe Thr Gly Glu Leu Leu Pro Asp Tyr Ile Leu Gln Gln Val
    610                 615                 620

Asp Leu Arg Ser Lys Phe Leu His Leu Val Ser Leu Thr Gly Arg Leu
625                 630                 635                 640

Ile Asn Asp Thr Lys Thr Tyr Gln Ala Glu Arg Asn Arg Gly Glu Leu
                645                 650                 655

Val Ser Ser Val Gln Cys Tyr Met Arg Glu Asn Pro Glu Cys Thr Glu
            660                 665                 670

Glu Glu Ala Leu Ser His Val Tyr Gly Ile Ile Asp Asn Ala Leu Lys
        675                 680                 685

Glu Leu Asn Trp Glu Leu Ala Asn Pro Ala Ser Asn Ala Pro Leu Cys
    690                 695                 700

Val Arg Arg Leu Leu Phe Asn Thr Ala Arg Val Met Gln Leu Phe Tyr
705                 710                 715                 720

Met Tyr Arg Asp Gly Phe Gly Ile Ser Asp Lys Glu Met Lys Asp His
                725                 730                 735

Val Ser Arg Thr Leu Phe Asp Pro Val Ala
            740                 745
```

<210> SEQ ID NO 40
<211> LENGTH: 53
<212> TYPE: DNA
<213> ORGANISM: Artificial Sequence
<220> FEATURE:
<223> OTHER INFORMATION: Primer

<400> SEQUENCE: 40
tcgcccatgg actgaaacat ttttttgtc gacttcacca atgtctggat tct         53

<210> SEQ ID NO 41
<211> LENGTH: 862
<212> TYPE: PRT
<213> ORGANISM: Taxus brevifolia

<400> SEQUENCE: 41

```
Met Ala Gln Leu Ser Phe Asn Ala Ala Leu Lys Met Asn Ala Leu Gly
1               5                   10                  15

Asn Lys Ala Ile His Asp Pro Thr Asn Cys Arg Ala Lys Ser Glu Arg
            20                  25                  30

Gln Met Met Trp Val Cys Ser Arg Ser Gly Arg Thr Arg Val Lys Met
        35                  40                  45

Ser Arg Gly Ser Gly Gly Pro Gly Pro Val Val Met Ser Ser Ser
    50                  55                  60

Thr Gly Thr Ser Lys Val Val Ser Glu Thr Ser Ser Thr Ile Val Asp
65                  70                  75                  80

Asp Ile Pro Arg Leu Ser Ala Asn Tyr His Gly Asp Leu Trp His His
                85                  90                  95

Asn Val Ile Gln Thr Leu Glu Thr Pro Phe Arg Glu Ser Ser Thr Tyr
            100                 105                 110

Gln Glu Arg Ala Asp Glu Leu Val Val Lys Ile Lys Asp Met Phe Asn
        115                 120                 125
```

-continued

```
Ala Leu Gly Asp Gly Asp Ile Ser Pro Ser Ala Tyr Asp Thr Ala Trp
    130                 135                 140

Val Ala Arg Leu Ala Thr Ile Ser Ser Asp Gly Ser Glu Lys Pro Arg
145                 150                 155                 160

Phe Pro Gln Ala Leu Asn Trp Val Phe Asn Asn Gln Leu Gln Asp Gly
                165                 170                 175

Ser Trp Gly Ile Glu Ser His Phe Ser Leu Cys Asp Arg Leu Leu Asn
            180                 185                 190

Thr Thr Asn Ser Val Ile Ala Leu Ser Val Trp Lys Thr Gly His Ser
        195                 200                 205

Gln Val Gln Gln Gly Ala Glu Phe Ile Ala Glu Asn Leu Arg Leu Leu
    210                 215                 220

Asn Glu Glu Asp Glu Leu Ser Pro Asp Phe Gln Ile Ile Phe Pro Ala
225                 230                 235                 240

Leu Leu Gln Lys Ala Lys Ala Leu Gly Ile Asn Leu Pro Tyr Asp Leu
                245                 250                 255

Pro Phe Ile Lys Tyr Leu Ser Thr Thr Arg Glu Ala Arg Leu Thr Asp
                260                 265                 270

Val Ser Ala Ala Ala Asp Asn Ile Pro Ala Asn Met Leu Asn Ala Leu
        275                 280                 285

Glu Gly Leu Glu Glu Val Ile Asp Trp Asn Lys Ile Met Arg Phe Gln
    290                 295                 300

Ser Lys Asp Gly Ser Phe Leu Ser Ser Pro Ala Ser Thr Ala Cys Val
305                 310                 315                 320

Leu Met Asn Thr Gly Asp Glu Lys Cys Phe Thr Phe Leu Asn Asn Leu
                325                 330                 335

Leu Asp Lys Phe Gly Gly Cys Val Pro Cys Met Tyr Ser Ile Asp Leu
                340                 345                 350

Leu Glu Arg Leu Ser Leu Val Asp Asn Ile Glu His Leu Gly Ile Gly
        355                 360                 365

Arg His Phe Lys Gln Glu Ile Lys Gly Ala Leu Asp Tyr Val Tyr Arg
    370                 375                 380

His Trp Ser Glu Arg Gly Ile Gly Trp Gly Arg Asp Ser Leu Val Pro
385                 390                 395                 400

Asp Leu Asn Thr Thr Ala Leu Gly Leu Arg Thr Leu Arg Met His Gly
                405                 410                 415

Tyr Asn Val Ser Ser Asp Val Leu Asn Asn Phe Lys Asp Glu Asn Gly
                420                 425                 430

Arg Phe Phe Ser Ser Ala Gly Gln Thr His Val Glu Leu Arg Ser Val
            435                 440                 445

Val Asn Leu Phe Arg Ala Ser Asp Leu Ala Phe Pro Asp Glu Arg Ala
        450                 455                 460

Met Asp Asp Ala Arg Lys Phe Ala Glu Pro Tyr Leu Arg Glu Ala Leu
465                 470                 475                 480

Ala Thr Lys Ile Ser Thr Asn Thr Lys Leu Phe Lys Glu Ile Glu Tyr
                485                 490                 495

Val Val Glu Tyr Pro Trp His Met Ser Ile Pro Arg Leu Glu Ala Arg
            500                 505                 510

Ser Tyr Ile Asp Ser Tyr Asp Asp Asn Tyr Val Trp Gln Arg Lys Thr
        515                 520                 525

Leu Tyr Arg Met Pro Ser Leu Ser Asn Ser Lys Cys Leu Glu Leu Ala
530                 535                 540
```

-continued

```
Lys Leu Asp Phe Asn Ile Val Gln Ser Leu His Gln Glu Glu Leu Lys
545             550                 555                 560

Leu Leu Thr Arg Trp Trp Lys Glu Ser Gly Met Ala Asp Ile Asn Phe
                565             570                 575

Thr Arg His Arg Val Ala Glu Val Tyr Phe Ser Ser Ala Thr Phe Glu
            580             585                 590

Pro Glu Tyr Ser Ala Thr Arg Ile Ala Phe Thr Lys Ile Gly Cys Leu
            595             600                 605

Gln Val Leu Phe Asp Asp Met Ala Asp Ile Phe Ala Thr Leu Asp Glu
            610             615                 620

Leu Lys Ser Phe Thr Glu Gly Val Lys Arg Trp Asp Thr Ser Leu Leu
625             630                 635                 640

His Glu Ile Pro Glu Cys Met Gln Thr Cys Phe Lys Val Trp Phe Lys
                645             650                 655

Leu Met Glu Glu Val Asn Asn Asp Val Val Lys Val Gln Gly Arg Asp
                660             665                 670

Met Leu Ala His Ile Arg Lys Pro Trp Glu Leu Tyr Phe Asn Cys Tyr
            675             680                 685

Val Gln Glu Arg Glu Trp Leu Glu Ala Gly Tyr Ile Pro Thr Phe Glu
            690             695                 700

Glu Tyr Leu Lys Thr Tyr Ala Ile Ser Val Gly Leu Gly Pro Cys Thr
705             710                 715                 720

Leu Gln Pro Ile Leu Leu Met Gly Glu Leu Val Lys Asp Asp Val Val
                725             730                 735

Glu Lys Val His Tyr Pro Ser Asn Met Phe Glu Leu Val Ser Leu Ser
            740             745                 750

Trp Arg Leu Thr Asn Asp Thr Lys Thr Tyr Gln Ala Glu Lys Ala Arg
            755             760                 765

Gly Gln Gln Ala Ser Gly Ile Ala Cys Tyr Met Lys Asp Asn Pro Gly
770             775                 780

Ala Thr Glu Glu Asp Ala Ile Lys His Ile Cys Arg Val Val Asp Arg
785             790                 795                 800

Ala Leu Lys Glu Ala Ser Phe Glu Tyr Phe Lys Pro Ser Asn Asp Ile
            805             810                 815

Pro Met Gly Cys Lys Ser Phe Ile Phe Asn Leu Arg Leu Cys Val Gln
            820             825                 830

Ile Phe Tyr Lys Phe Ile Asp Gly Tyr Gly Ile Ala Asn Glu Glu Ile
            835             840                 845

Lys Asp Tyr Ile Arg Lys Val Tyr Ile Asp Pro Ile Gln Val
850             855                 860
```